US007247450B2

(12) United States Patent
Ferrari et al.

(10) Patent No.: US 7,247,450 B2
(45) Date of Patent: Jul. 24, 2007

(54) **SECRETION, TRANSCRIPTION AND SPORULATION GENES IN *BACILLUS CLAUSII***

(75) Inventors: Eugenio Ferrari, Palo Alto, CA (US); Anita Van Kimmenade, Palo Alto, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 10/502,667

(22) PCT Filed: Feb. 6, 2003

(86) PCT No.: PCT/US03/03534

§ 371 (c)(1), (2), (4) Date: Apr. 7, 2005

(87) PCT Pub. No.: WO03/066818

PCT Pub. Date: Aug. 14, 2003

(65) Prior Publication Data

US 2005/0209448 A1 Sep. 22, 2005

Related U.S. Application Data

(60) Provisional application No. 60/355,258, filed on Feb. 8, 2002.

(51) Int. Cl.
*C12P 21/06* (2006.01)

(52) U.S. Cl. ...................... 435/69.1; 435/6; 435/320.1; 435/325; 536/23.1; 530/350

(58) Field of Classification Search ..................... None
See application file for complete search history.

(56) References Cited

U.S. PATENT DOCUMENTS

| | | | |
|---|---|---|---|
| 5,264,366 A | 11/1993 | Ferrari et al. | 435/252.31 |
| 5,322,770 A | 6/1994 | Gelfand | 435/6 |
| 2002/0146721 A1 | 10/2002 | Berka et al. | 435/6 |

OTHER PUBLICATIONS

International Search Report for International Application No. PCT/US03/03534 filed Aug. 20, 2004.

Altschul et al., "Basic Local Alignment Search Tool" (1990) *J. Mol. Biol.* 215, 403-410.

Altschul et al., "Local Alignment Statistics" (1996) *Methods in Enzymology*, vol. 266, pp. 460-480.

Bakhiet, Nouna et al., "Studies of Transfection and Transformation of Protoplasts of *Bacillus larvae, Bacillus subtillis*, and *Bacillus popilliae*," Appl. Environ. Microbiol., vol. 49, No. 3, pp. 577-581, 1985.

Bron, Sierd, "Plasmids," Molecular Biological Methods for *Bacillus*, ed. Harwood & Cutting, John Wiley & Sons, chapter 3, 1990.

Chang, Shing et al. "High Frequency Transformation of *Bacillus subtilis* Protoplasts by Plasmid DNA," Mol. Gen. Genet. 168:111-115, 1979.

Contente, Sara et al., "Marker Rescue Transformation by Linear Plasmid DNA in *Bacillus subtilis*," Plasmid, 2:555-571, 1979.

Devereux et al., "A Comprehensive set of sequence analysis programs for the VAX," Nucl. Acids Res., 12(1):387-395, 1984.

Feng et al., "Progressive Sequence Alignment as a Prerequisite to Correct Phylogenetic Tress" *J. Mol Evol.*, 25:351-360, 1987.

Fisher et al., "Introduction of plasmid pC194 into *Bacillus thuringiensis* by protoplast transformation and plasmid transfer," *Archives of Microbiology*, 139:213-217, 1984.

Haima, Peter et al., "Novel plasmid marker rescue transformation system for molecular cloning in *Bacillus subtilis* enabling direct selection of recombinants," *Mol. Gen. Genet.*, 223:185-191, 1990.

Hale & Marham, The Harper Collins Dictionary of Biology, Harper Perennial, NY (1991).

Higgins et al., "Fast and sensitive multiple sequence alignments on microcomputer," *Cabios Communications*, 5:(2):151-153, 1989.

Holubova, I. et al. "Transfer of Liposome-Encapsulated Plasmid DNA to *Bacillus subtilis* Protoplasts and Calcium-Treated *Escherichia coli* Cells," *Folia Microbiol.*, 30:97-100, 1985.

Karlin, S. et al., "Applications and statistics for multiple high-scoring segments in molecular sequences," *Proc. Natl. Acad. Sci. USA*, 90(12):5873-5788, 1993.

Mann, Stephen P. et al., "Transformation of *Bacillus* spp.: an Examination of the Transformation of *Bacillus* Protoplasts by Plasmids pUB110 and pHV33," *Current Microbiol.*, 13:191-195, 1986.

McDonald, Karen Orzech et al., "Plasmid Transformation of *Bacillus sphaericus* 1593," *Journal of General Microbiology*, 130:203-208, 1984.

Mewes, H. W. et al., "The Yeast Genome Directory," *Nature*, vol. 387, Supp., p. 5, 1997.

Mewes, H. W. et al., "Overview of the yeast genome," *Nature*, vol. 387, Supp., pp. 7-65, 1997.

Msadek, T. et al., (1993) "*Two component regulatory systems*" In A. L. Sonenshein, J. A. Hoch, and R. Losick (Ed.), *Bacillus subtillis* and other gram-positive bacteria. American Society for Microbiology, Washington, D. C., pp. 729-745.

Needleman, S. et al., "A General Method Applicable to the Search for Similarities in the Amino Acid Sequence of Two Proteins," *J. Mol. Biol.*,48:443-453, 1970.

Pearson, William R. et al., "Improved tools for biological sequence comparison," *Proc. Natl. Acad. Sci. USA*, 85:2444-2448, 1988.

Smith, Michael D. et al. "Protoplast Transformation in Coryneform Bacteria and Introduction of an α-Amylase Gene from *Bacillus amyloliquefaciens* into *Brevibacterium lactofermentum*," *Applied and Environmental Microbiology*, 51(3):634-639, 1986.

(Continued)

*Primary Examiner*—Hope Robinson

(57) ABSTRACT

The present invention relates to cells that have been genetically manipulated to have an altered capacity to produce expressed proteins. In particular, the present invention relates to Gram-positive microorganisms having exogenous nucleic acid sequences introduced therein and methods for producing proteins in such host cells, such as members of the genus *Bacillus*. More specifically, the present invention relates to the expression, production and secretion of a polypeptide of interest and to cells that have been genetically manipulated to have an altered capacity to produce expressed proteins. In particular, the present invention provides for the enhanced expression of a selected polypeptide by a microorganism.

9 Claims, 22 Drawing Sheets

OTHER PUBLICATIONS

Smith, Temple F. et al.,"Comparison of Biosequences," *Adv. Appl. Math.*, 2:482-489, 1981.

Takamatsu, Hiromu et al., "In Vivo and In Vitro Characterization of the *secA* Gene Product of *Bacillus subtilis*," *Journal of Bacteriology*, 174(13):4308-4316, 1992.

Takami, Hideto et al., "Complete genome sequence of the alkaliphilic bacterium *Bacillus halodurans* and genomic sequence comparison with *Bacillus subtilis*," *Nucleic Acids Research*, 28(21):4317-4331, 2000.

Vorobjeva, I. P. et al., "Transformation of *Bacillus megaterium* Protoplasts by Plasmid DNA," *FEMS Microbiology Letters*, 7:261-263, 1980.

Weinrauch, Y. et al., "Plasmid Marker Rescue Transformation in *Bacillus subtilis*," *Journal of Bacteriology*, 154(3):1077-1087, 1983.

Weinrauch, Y. et al., "Plasmid Marker Rescue Transformation Proceeds by Breakage-Reunion in *Bacillus subtilis*," *Journal of Bacteriology*, 169(3):1205-1211, 1987.

Duedahl-Olesen et al., "Purification and characterisation of a malto-oligosaccharide-forming amylase active at high pH from *Bacillus clausii* BT-21," *Carbohydrate Research*, 329:97-107 (2000).

Nielsen et al., "Phenetic diversity of alkaliphilic *Bacillus* strains: proposal for nine new species," *Microbiology*, 141:1745-1761 (1995).

Van Wely et al., "The carboxyl terminus of the *Bacillus subtilis* SecA is dispensable for protein secretion and viability," *Microbiology*, 146:2573-2581 (2000).

Widner et al.,"Development of marker-free strains of *Bacillus subtilis* capable of secreting high levels of industrial enzymes," *Journal of Industrial Microbiology & Biotechnology*, 25:204-212 (2000).

*B. clausii* spoIIE aa sequence

```
MISKVIKTSE EMGTAKVAEK LNGIWTKCAS SGQALKSGAK TVLYDWGIFI AILGFLLGRA MILSELTPFI LPFLAAVFLL RRSQSLIAAA  90
SLLAGAVFSF HGQLIFAIAG IGFFLILYKC MKMFMKYPAK SLPYLVFSAS IATRLSLVFL TEGGLSQYAM MMATVEAALS FILTMIFIQS 180
IPLVTGKRGG QALRNEEIIC LIILLASVMT GTVGWTINEA VLQHSFASYL VLVFAFVGGA AIGSTVGVVT GLILSLASLA SLYQMSLLAF 270
AGLLGGLLKE GKRIGVSLGL LVGTLLIGMY GQGGGLGASV SESAIAITLF LLTPKSWLTK VARYIPGTVE HSQEQQQYLR KVRDATAGKV 360
ERFSSLFQTL SNSFHTPSKN EEEEHDHEVD VLLSRVTEKT CQTCMLKEKC WVQNFNATYD SMKQMVQESE VHGTVVDPKL QRQWRSHCRK 450
PDQVMAALNA EVNHYRANKE LKRQVLESQR LVADQLLGVS RVMGDFAKEI QKEKQPHVIQ EEHMVDALRN AGLEVGHIDI YSMESGSIEI 540
EMSVLCSHEN GEAEKIIAPM LSDLVKETIV LMREEPGFYS NGYSHISFGS AKPFAVETGI AKVAKGGEWL SGDNYAMIKL NSEKFAVAIS 630
DGMGNGEKAH LESSETLKLL QKVLQSGIEE TVAIKSVNSI LSLRNTEEMF STLDLAMIDM QDAGAKFLKI GSTPSFIKRK DHVIKIEAGN 720
LPMGILHEFE VDVVSEQLKP GDLLIMCSDG VFDAKRQIEN KEQWMKRMIK EIETDDPQEV ADVLLEKVIR SEKGIVIEDD MTIVVTQLKH 810
NTPKWSSIPI HPKTTKNKKT APFYKQATGT                                                                840
```

Figure 1

*B. clausii spoIIE* DNA sequence

```
ATGATCAGTA AAGTGATAAA GACGTCAGAA GAAATGGGTA CAGCGAAAGT AGCCGAAAAG CTAAACGGCA TATGGACCAA ATGTGCAAGC   90
AGTGGACAAG CCCTTAAAAG CGGAGCCAAA ACGGTGCTTT ATGATTGGGG CATATTCATT GCCATTCTTG GTTTTCTGCT AGGAAGGGCT  180
ATGATTTTAT CAGAGTTGAC GCCATTTATC TTGCCATTCT TGGCGGCCGT GTTCTTGTTA AGACGCTCTC AATCACTCAT TGCTGCAGCT  270
TCATTATTAG CAGGTGCTGT GTTCAGTTTC CATGGTCAGT TGATTTTTGC GATTGCAGGG ATCGGGTTTT TTCTTATTCT GTACAAATGT  360
ATGAAAATGT TCATGAAGTA CCCTGCTAAA TCGCTCCCTT ATCTTGTGTT TTCAGCTAGT ATCGCCACGA GGCTGTCACT CGTATTTTTG  450
ACAGAAGGTG GATTAAGCCA ATATGCGATG ATGATGGCTA CAGTCGAAGC GGCGCTTAGC TTTATCCTGA CAATGATCTT TATCCAAAGC  540
ATACCGCTTG TGACAGGAAA AAGAGGCGGA CAAGCACTCC GGAATGAAGA AATTATTTGT TTAATTATTT TGCTTGCCTC TGTAATGACA  630
GGAACAGTCG GTTGGACGAT AAATGAAGCT GTGCTTCAGC ATAGCTTTGC AAGTTATCTC GTTTTAGTGT TTGCTTTTGT TGGCGGGGCT  720
GCAATAGGCT CGACTGTCGG AGTGGTGACA GGCTTGATTT TAAGCTTGGC CAGTTTAGCA AGTCTTTATC AGATGAGTCT GCTTGCCTTT  810
GCAGGCTTGT TAGGAGGGTT GTTAAAGGAA GGGAAACGGA TCGGCGTGTC ACTTGGCTTA CTTGTAGGAA CGCTTTTAAT TGGCATGTAT  900
GGCCAAGGGG GCGGGCTTGG GGCAAGTGTG TCAGAGTCTG CCATTGCGAT CACGCTATTT TTATTGACGC CAAAGAGCTG GCTGACGAAA  990
GTAGCACGCT ATATTCCTGG GACAGTTGAG CATTCCCAGG AACAGCAGCA GTATTTACGG AAAGTCCGGG ACGCGACAGC GGGAAAGGTT 1080
GAACGGTTTT CGTCTTTATT CCAAACACTA TCGAACAGCT TTCATACACC TTCTAAAAAT GAGGAAGAAG AGCATGACCA TGAGGTCGAT 1170
GTCCTCCTTA GCCGCGTGAC GGAAAAAACA TGCCAAACGT GCATGTTGAA AGAAAAGTGC TGGGTGCAAA ACTTTAATGC TACCTATGAT 1260
TCAATGAAGC AAATGGTCCA GGAAAGTGAG GTGCATGGAA CAGTTGTCGA TCCAAAATTA CAAAGGCAAT GGCGCAGCCA TTGCCGCAAG 1350
CCTGACCAAG TCATGGCTGC CCTTAATGCT GAAGTGAACC ATTATCGGGC AAACAAGGAA TTGAAGAGGC AAGTGTTAGA GAGCCAACGG 1440
CTAGTCGCCG ACCAATTGCT TGGCGTTTCC CGGGTAATGG GTGATTTCGC CAAAGAAATC CAAAAAGAAA AGCAACCTCA TGTCATCCAA 1530
GAAGAACATA TGGTGGATGC TTTGAGAAAC GCCGGCCTTG AGGTTGGGCA TATAGACATT TACAGCATGG AGAGTGGTAG CATTGAAATT 1620
GAAATGAGTG TTTTATGCAG CCACGAAAAT GGCGAGGCGG AAAAAATCAT CGCGCCCATG CTTTCTGATT TAGTCAAGGA AACGATTGTG 1710
TTGATGCGGG AAGAACCAGG CTTTTATTCA AATGGATATA GCCATATTTC ATTTGGGTCA GCAAAGCCTT TTGCTGTTGA AACAGGCATT 1800
GCCAAAGTCG CCAAAGGCGG CGAATGGCTG TCTGGAGACA ATTACGCCAT GATCAAATTA AATAGCGAAA AGTTCGCAGT TGCGATAAGC 1890
GACGGCATGG GCAACGGCGA AAAAGCCCAT TTGGAAAGCA GTGAAACGTT GAAATTGCTG CAAAAAGTGC TGCAATCAGG AATTGAAGAA 1980
ACAGTGGCAA TCAAATCAGT CAATTCCATC TTGTCATTGC GCAACACTGA AGAAATGTTC TCCACCCTCG ATCTGGCGAT GATCGATATG 2070
CAAGATGCAG GAGCGAAATT CCTGAAAATT GGATCAACAC CAAGCTTTAT TAAGCGGAAA GATCACGTCA TAAAAATTGA AGCAGGCAAC 2160
TTGCCAATGG GCATTCTCCA CGAATTTGAA GTAGACGTTG TTAGCGAGCA GCTTAAGCCA GGTGACTTGC TGATTATGTG CAGCGATGGG 2250
GTGTTTGATG CGAAAAGGCA AATTGAAAAC AAAGAGCAGT GGATGAAACG TATGATTAAG GAAATTGAAA CCGATGACCC CCAAGAAGTG 2340
GCCGATGTGC TATTAGAGAA AGTCATTCGT TCGGAAAAAG GGATTGTGAT TGAGGATGAC ATGACGATCG TTGTTACTCA GTTGAAACAT 2430
AATACGCCGA AATGGTCTTC GATTCCGATC CATCCGAAAA CGACTAAAAA CAAGAAAACC GCGCCGTTCT ATAAACAGGC AACAGGCACG 2520
```

Figure 2

*B. clausii* DegU

```
MITQETQEIR IVIIDDHPLF KEGVKRILSM EENFNVVADG EDGSEVIDLV    50
RQHQPDVILM DINMPKTNGV EATKDLIKAF PKVKVIILSI HDDESYVSHV   100
LRTGASGYLL KEMDAESLVE AVKVVASGGA YIHPKVTSNL IKEYRRLARQ   150
DEQYQDSIGF REVEYRKPLH ILTRRECEVL QLMTDGQNNR AIGESLYISE   200
KTVKNHVSNI LQKMNVNDRT QAVVESIKKG YVIVR                   235
```

Figure 3A

*B. clausii* DegS

```
MKKRGVFMTDVTMLDHIITQTLDSVGTSREKIFEIGERSRNEYEYLKKELDQVKVKLTHV
INDVDETVLKTKHARNRLAKVSKEFNRYTSEEVRTAYEQASDFQVQLAVLQQEEIQLRIR
RDDIDRRLKNLQDTINRAEQLSVQMSVVFDFLSSDLKQVGEYIKDANEKQAFGLKIIEAQ
EEERRRLSREIHDGPAQMMANVMLHSELIERIYQERGIEEALKEIRGLRRMVRSSLAEVR
RIIYDLRPMALDDLGLVPTLRKYLENIEERHGLKVTFKHFGVEKRLAQQFEIALFRLVQE
AVQNATKHAEPTEIIVKIELKPKNVTLVIRDDGKGFDLSERKESSFGLIGMKERVNMLNG
KMTIHSKPQEGTNILIQLPVSTN
```

Figure 3B

*B. clausii DegU*

```
ATGATTACTC AAGAAACACA AGAAATTCGC ATTGTCATTA TAGACGACCA    50
TCCATTGTTT AAAGAAGGGG TAAAGCGGAT TTTATCGATG GAGGAAAATT   100
TTAATGTTGT TGCAGATGGG GAAGACGGAT CGGAAGTTAT CGATTTGGTT   150
CGCCAACATC AGCCAGATGT CATTTTAATG GATATTAATA TGCCAAAAAC   200
GAATGGCGTC GAAGCAACAA AAGACTTGAT CAAGGCATTT CCAAAAGTGA   250
AAGTAATTAT TCTTTCAATT CATGATGATG AGTCTTATGT TTCCCATGTG   300
TTACGTACAG GAGCCTCAGG TTACTTATTA AAAGAAATGG ATGCGGAATC   350
ATTGGTTGAA GCTGTAAAAG TGGTGGCATC CGGCGGCGCT TATATTCATC   400
CAAAAGTGAC ATCAAATTTG ATTAAAGAAT ACCGTCGCCT TGCCCGCCAA   450
GATGAGCAAT ACCAAGACTC GATCGGTTTC CGTGAAGTCG AGTATAGAAA   500
GCCGCTTCAT ATTTTAACTA GGAGAGAGTG TGAAGTGCTT CAGCTTATGA   550
CGGATGGACA AAACAACCGG GCAATCGGCG AGTCGCTTTA CATAAGCGAG   600
AAGACAGTGA AAAACCATGT TAGCAACATT TTGCAAAAAA TGAACGTGAA   650
CGACCGAACG CAAGCAGTGG TAGAGTCCAT AAAAAAAGGA TATGTCATCG   700
TTCGC                                                    705
```

Figure 4A

*B.claussi DegS*

```
TTGAAAAAGCGAGGAGTATTCATGACAGACGTAACGATGCTTGATCATATAATTACGCAA
ACGCTTGACTCAGTTGGGACGAGTCGCGAAAAAATCTTTGAAATCGGTGAACGCTCCCGC
AATGAGTATGAATACTTGAAAAAGGAATTAGATCAAGTCAAAGTTAAATTAACACACGTT
ATTAATGATGTCGACGAAACCGTGTTAAAAACAAAACACGCACGAAACCGGTTAGCCAAA
GTAAGCAAGGAATTCAATCGGTACACAAGTGAGGAAGTCCGTACAGCGTACGAACAAGCC
AGCGATTTCCAAGTACAGCTGGCCGTGCTTCAACAAGAAGAGATCCAATTGCGGATTAGG
CGGGATGATATTGATCGCCGCTTGAAAAATCTTCAGGATACGATTAATCGGGCTGAACAG
CTTTCTGTACAGATGTCCGTGGTGTTTGACTTTTTATCAAGTGACCTTAAGCAAGTCGGC
GAATACATTAAAGACGCCAATGAAAAGCAAGCGTTCGGCTTAAAAATAATCGAGGCACAG
GAAGAAGAGCGTCGCCGTCTTTCCCGGGAAATCCATGACGGGCCAGCTCAGATGATGGCA
AACGTTATGCTTCATTCAGAATTGATTGAACGGATTTACCAGGAACGGGGCATTGAGGAA
GCGCTTAAAGAAATTCGCGGGTTGCGCCGTATGGTTCGTTCTTCATTGGCAGAGGTAAGA
AGAATCATTTATGATTTGCGCCCGATGGCGTTGGATGATTTAGGGCTAGTGCCTACATTG
AGAAAGTATTTGGAGAATATTGAAGAGCGTCATGGCTTAAAAGTCACTTTTAAACACTTT
GGCGTTGAAAAGAGGCTTGCCCAACAATTTGAAATTGCGTTATTTCGCCTTGTGCAGGAA
GCGGTGCAAAATGCGACTAAGCACGCAGAACCGACTGAAATTATCGTGAAGATTGAATTG
AAACCAAAAAATGTAACGCTAGTCATTAGAGATGACGGCAAAGGATTTGACCTTTCTGAA
AGAAAGGAATCTTCGTTTGGGTTAATAGGCATGAAAGAAAGGGTTAACATGCTAAATGGC
AAAATGACGATTCATTCCAAACCGCAAGAAGGAACAAATATTTTGATTCAACTCCCTGTC
TCTACGAATTAA
```

Figure 4B

*B. clausii* FtsY
VSFFKKLREKMAQQTNEVADKFKHGLEKTRTSFSGKINELVARYRKIDEDFFEDLEEILI
GADVGVSTVMELVDELKEEVRLRNLKDTEEIQPVISEKLASLLEKDDKDTTLQLQEGLSV
ILVVGVNGVGKTTSIGKLAHYLKGQGKSVVLAAGDTFRAGAIDQLDVWGERVGVPVIKQQ
EGSDPAAVMYDAIAWARSRKADVLICDTAGRLQNKVNLMNELAKVKRVNEREVPGAPHEV
LLVVDATTGQNALSQAKAFAASTDVSGLVLTKLDGTAKGGIVIAIRQELDLPVKFIGLGE
QKDDLQPFDAEQFVYGLFKDAIDAEKNDQ

Figure 5

*B. clausii* ftsY DNA sequence
GTGAGCTTTTTTAAAAAATTGAGAGAAAAAATGGCGCAGCAAACGAATGAAGTAGCGGAC
AAATTTAAACATGGATTAGAAAAAACACGGACAAGCTTTtCGGGCAAAATCAATGAGCTT
GTCGCCCGCTACCGTAAAATCGACGAAGATTTCTTTGAAGACTTGGAGGAAATCCTGATT
GGCGCCGATGTCGGTGTTTCAACAGTAATGGAACTTGTTGACGAATTAAAGGAAGAAGTG
CGTTTGCGCAACTTAAAGGACACCGAAGAGATACAGCCTGTCATTTCCGAAAAACTAGCT
AGTCTCTTAGAAAAAGACGATAAAGACACAACGCTCCAATTACAAGAAGGGTTGAGCGTC
ATTCTTGTTGTTGGCGTAAATGGCGTCGGCAAAACGACGTCCATTGGCAAGCTCGCCCAT
TATTTAAAAGGGCAAGGAAAATCTGTCGTGCTCGCCGCTGGCGATACATTCCGAGCGGGT
GCGATTGACCAGCTTGACGTTTGGGGAGAACGTGTTGGCGTTCCAGTTATTAAACAGCAA
GAAGGCTCTGACCCGGCGGCGGTCATGTATGATGCGATTGCTTGGGCACGTTCCCGCAAA
GCCGATGTGCTTATTTGCGATACAGCGGGGCGCCTGCAAAACAAAGTCAATTTAATGAAT
GAGCTGGCAAAAGTAAAACGCGTCAATGAAAGGGAAGTGCCAGGAGCTCCCCACGAAGTA
CTGCTTGTCGTCGATGCGACAACAGGCCAAAATGCTTTGTCGCAAGCGAAAGCATTTGCA
GCTTCAACTGACGTGAGCGGCCTTGTCCTCACGAAACTTGATGGCACGGCCAAAGGAGGC
ATTGTCATTGCCATTCGCCAAGAGCTTGATTTGCCAGTTAAGTTTATCGGGCTAGGTGAA
CAGAAAGACGATTTGCAGCCATTTGACGCTGAGCAATTTGTGTATGGGCTGTTTAAGGAC
GCGATCGATGCCGAAAAGAATGACCAGTGA

Figure 6

*B. clausii* Ffh aa sequence

```
MAFEGLAARL QDTLTKIRGK GKVSEQDIKE MMREVRLALL EADVNFKVVK    50
QFIANVKEKA LGQEVMKSLT PGQQVIKVVN EELTALMGAE QSKIAVAQKP   100
PTVVMMVGLQ GAGKTTTTAK LANHLRKKHN RKPLLVACDV YRPAAIQQLE   150
TLGKQLNMPV FSKGTDANPV DIAKEAVATA KAEHHDYVLI DTAGRLHVDE   200
TLMAELQDMK AAVTPDEILL VVDSMTGQDA VNVAESFNNQ LDVTGAVLTK   250
LDGDTRGGAA ISIKAVTNTP IKFAGMGEKI DQLEPFHPDR MASRILGMGD   300
VLSLIEKAQA NVDEEKAKEL EKKLRKMDFT FDDFLEQLDQ VKSMGPLEDL   350
LGMMPGMNKA KGMKNLKVDE KQLTELKRL                          379
```

Figure 7

*B. clausii ffh* DNA sequence

```
ATGGCATTTG AAGGACTTGC CGCGCGCCTG CAAGATACGT TGACAAAAAT    50
TCGCGGCAAA GGCAAAGTCA GCGAACAAGA CATCAAAGAA ATGATGCGAG   100
AAGTCCGGTT GGCATTGCTT GAAGCGGACG TTAACTTTAA AGTCGTAAAG   150
CAATTCATTG CGAATGTGAA AGAAAAGGCG CTTGGCCAAG AAGTTATGAA   200
AAGCCTAACG CCTGGCCAGC AAGTGATCAA AGTCGTAAAC GAAGAGTTGA   250
CCGCATTGAT GGGGGCGGAG CAAAGCAAAA TTGCTGTTGC CCAAAAACCG   300
CCAACTGTGG TGATGATGGT AGGCTTGCAA GGTGCTGGGA AAACGACGAC   350
AACGGCAAAG CTCGCCAATC ATTTGCGCAA GAAGCACAAC CGCAAGCCAC   400
TGCTCGTTGC CTGTGACGTT TACCGCCCAG CGGCTATCCA ACAGTTGGAG   450
ACGCTTGGCA AGCAACTGAA CATGCCTGTC TTTTCCAAAG GGACGGACGC   500
CAATCCAGTT GATATAGCTA AAGAAGCGGT TGCGACTGCC AAAGCAGAAC   550
ATCATGATTA TGTGTTGATT GATACGGCTG GCCGCCTTCA TGTAGATGAA   600
ACGTTAATGG CGGAACTGCA AGATATGAAA GCAGCTGTCA CACCTGATGA   650
AATTTTGCTA GTCGTCGATT CGATGACAGG TCAAGATGCT GTCAATGTCG   700
CAGAGAGCTT TAACAACCAG CTTGATGTCA CAGGCGCTGT GTTGACGAAA   750
CTAGATGGCG ATACCCGCGG AGGGGCTGCG ATTTCCATTA AGGCAGTAAC   800
AAATACGCCG ATTAAATTTG CCGGCATGGG CGAAAAAATT GACCAGCTAG   850
AACCGTTCCA TCCAGATAGG ATGGCTTCTA GAATTCTCGG CATGGGCGAT   900
GTTCTGTCGT TAATCGAAAA AGCGCAAGCG AATGTCGATG AAGAAAAAGC   950
AAAAGAGCTT GAGAAAAAAC TTCGCAAAAT GGACTTTACG TTCGATGATT  1000
TTCTAGAGCA GCTCGACCAA GTCAAAAGCA TGGGGCCTCT TGAAGATTTG  1050
CTAGGGATGA TGCCGGGGAT GAATAAGGCA AAAGGCATGA AAAACCTAAA  1100
AGTTGATGAA AAGCAATTGA CCGAGTTGAA GCGATTG                1137
```

Figure 8

*B. clausii* secA protein

MLGLLRKIVGDPAQKQLKKNEKIVDIKCEALQCMKQLSDEQLKNKTAEFKAKLEEGASLNDIVVPALAVAREAAGRVLNEYPYRVQLLGALALHQGNI
AEMKTGEGKTLVGTIAVYVQALEGKGVHIVTVNNYLARRDLENYGRIFQFLGLTVGLNENGLTREEKQKAYAADVTYSTNNELGFDYLRDNMVLYKEQ
MVQRPLHFALIDEVDSILIDEARTPLIISGSVERKTKLYGQANTFVRVLKRDADYTYDEKTKSVQLTDEGVNKAERAFNIDNLYDQKHVQLNHHINQS
LKAHVAMHRDADYVVEDGEVVIVDQFTGRLMKGRRYSDGLHQALEAKEGLEVQRESITLASITFQNYFRMYQKLAGMTGTAKTEEEEFRNIYGMDVMV
IPTNKPVAREDRPDLIYKTMQGKFNAVVSEIAELHKTGRPVLVGTVNVETSEVVSKMLTRKRIPHHVLNAKNHEREAEIIEKAGHKGAVTIATNMAGR
GTDIKLGPGVKELGGLHVLGTERHESRRIDNQLRGRAGRQGDVGSSQFYLSMEDELMRRFGSDNMKAMMEKLGMEDDQPIESSLVSRAVETAQKRVEG
NNFDARKQVLQFDDVMREQREIIYKQRMEVLEADNLKTIVENMMKATVERVVQTHCPESLVQEEWDLAAVATYINGQLLSENGISEKELKGKEQEELI
ELITEKVLAAYHAKEAEVSSEQMREFEKVIMLRTVDRKWMNHIDQMDQLRQGIHLRAYGQNDPLREYRFEGFNMFEAMIAEIEEEVSMYVMKAQVQQN
LKREEVAEGKAVKPSANGQEDKKAKRKPVRKAENIGRNDPCICGSGKKYKNCCGANR

Figure 9

*B. clausii secA* DNA sequence

ATGCTTGGATTACTTCGAAAAATAGTCGGCGATCCAGCCCAAAAACAATTAAAGAAAAACGAAAAAATCGTCGACATCAAGTGCGAGGCGCTGCAGTG
CATGAAGCAGCTTTCTGACGAACAATTAAAGAACAAAACAGCTGAATTCAAGGCAAAGCTAGAAGAAGGCGCTTCTCTTAACGATATAGTAGTTCCTG
CGCTTGCAGTTGCTCGTGAAGCTGCGGGCAGGGTGTTAAATGAGTATCCATACCGCGTCCAGTTGCTCGGTGCACTGGCGCTGCACCAAGGCAATATT
GCCGAAATGAAAACAGGGGAAGGGAAAACGCTCGTCGGCACAATTGCCGTCTATGTCCAAGCCCTGGAGGGAAAAGGCGTTCATATTGTAACGGTCAA
TAACTACTTAGCCCGCCGCGACTTAGAAAACTATGGGCGGATTTTTCAATTCTTAGGGTTGACAGTAGGATTGAATGAAAACGGCCTTACGAGAGAAG
AAAAACAAAAAGCATATGCCGCTGATGTGACGTACAGCACAAATAATGAGCTTGGGTTTGATTATTTGCGTGATAACATGGTGCTTTACAAAGAACAA
ATGGTGCAACGGCCGCTCCATTTTGCGTTAATCGATGAAGTTGACTCGATTTTAATTGATGAAGCACGGACGCCGCTAATTATTTCTGGTTCTGTTGA
ACGGAAAACAAAACTTTATGGACAAGCCAATACATTTGTGCGCGTTTTAAAGCGCGATGCTGATTACACATACGATGAAAAAACAAAATCTGTCCAGT
TGACGGATGAAGGTGTCAATAAAGCAGAGCGCGCGTTTAACATCGACAACCTTTACGATCAAAAGCATGTCCAACTGAACCATCATATTAACCAATCG
TTAAAAGCCCATGTGGCCATGCACCGTGATGCTGACTATGTCGTAGAAGACGGCGAAGTCGTAATCGTTGACCAGTTTACGGGTCGTTTAATGAAAGG
AAGGCGTTATAGCGACGGACTTCACCAAGCGCTAGAAGCAAAAGAAGGTTTAGAGGTGCAGCGCGAAAGCATCACGCTAGCATCGATTACATTCCAAA
ACTATTTCCGTATGTACCAAAAGCTCGCAGGAATGACGGGGACGGCTAAGACGGAGGAAGAAGAGTTCCGCAATATTTACGGCATGGACGTAATGGTC
ATTCCGACCAATAAACCGGTTGCTCGGGAAGACCGCCCTGATTTAATTTATAAGACGATGCAAGGGAAATTCAACGCAGTCGTCAGTGAAATTGCCGA
GCTTCACAAAACGGGGCGCCCTGTGCTAGTAGGTACAGTCAACGTTGAAACATCTGAAGTTGTTTCCAAAATGTTGACAAGAAAACGGATTCCACACC
ACGTCTTAAATGCAAAAAACCATGAGCGAGAAGCAGAAATTATTGAAAAAGCTGGCCATAAAGGGGCCGTCACGATCGCAACGAACATGGCTGGACGT
GGAACGGACATTAAACTTGGCCCAGGGGTTAAAGAGCTTGGCGGCCTCCACGTTCTTGGTACAGAGCGCCATGAGAGCCGGCGGATTGACAACCAATT
GCGTGGTCGTGCTGGGCGTCAAGGGGATGTAGGTTCTTCTCAGTTTTATTTGTCGATGGAAGATGAGCTGATGAGGCGGTTTGGCTCAGACAATATGA
AAGCGATGATGGAAAAGCTAGGCATGGAAGACGACCAGCCTATTGAATCATCATTGGTTTCAAGGGCGGTGGAAACAGCTCAGAAGCGGGTTGAAGGC
AATAACTTTGATGCTCGTAAACAAGTGCTCCAGTTTGACGACGTTATGCGTGAGCAACGGGAGATTATTTACAAACAACGGATGGAAGTGCTTGAAGC
CGATAACTTAAAAACAATTGTCGAAAATATGATGAAGGCGACTGTAGAACGTGTAGTTCAAACCCATTGCCCTGAATCGCTCGTTCAGGAAGAATGGG
ATTTGGCTGCTGTTGCCACCTATATCAACGGGCAATTGCTGTCTGAAAACGGAATTAGTGAGAAAGAGCTGAAAGGGAAAGAGCAAGAGGAACTGATC
GAGTTGATTACCGAAAAAGTCCTCGCTGCATACCATGCGAAAGAAGCAGAAGTCTCTTCAGAACAAATGCGCGAGTTTGAAAAAGTGATCATGCTGCG
CACTGTTGACCGCAAGTGGATGAACCACATTGACCAAATGGATCAATTACGACAAGGCATACATTTGCGCGCTTACGGCCAAAATGATCCGTTGCGTG
AGTATCGCTTTGAAGGCTTTAATATGTTTGAAGCGATGATCGCTGAAATTGAAGAAGAAGTATCTATGTACGTGATGAAAGCTCAAGTGCAACAAAAC
CTTAAGCGTGAGGAAGTAGCTGAAGGAAAAGCGGTGAAACCGTCAGCCAATGGGCAAGAGGACAAAAAAGCGAAACGGAAACCAGTCCGCAAAGCTGA
AAACATTGGYAGAAATGATCCATGCATTTGTGGCAGCGGCAAAAAATACAAAAATTGTTGTGGGGCTAACCGATAA

Figure 10

*B.clausii* secD aa sequence

```
MVKKGKIALF FLIIALFASG IAYFAKPVVN DVSLGLDLQG GFEVLYEVEP    50
MNEGDEINQD SLLATTTALN ERVNTIGVSE PNIQIEGENR IRVQLAGVED   100
QETARDILAT GAELTIRDVD DNVLLDGSDL TQNGASASVH PEKNQPIVTL   150
TLNDADKFGE ITREISERPL GENLLVIWLD FEEGDSFAEE SKKQDPKYMS   200
AASVNAPLHT RDVMIEGNFT TEETRFLAEI LNAGALPVEL NEIYSTSVGA   250
SLGEKAMNQT IFAGSLGVGL IFLYMVVYYR FPGIIAVITL SIYTFLVLVV   300
FNAMNAVLTL PGIAALVLGV GMAVDANIIT YERIKEEIKS GKSILSAFKV   350
GSRRSFATIF DANITTLIAA GVMFYFGTSS VQGFAVMLII SILVSFLTAV   400
YGSRVLLGLW VNSKFLNKRP GWFGVKRGEI DEL                     433
```

Figure 11

*B. clausii secD* DNA sequence

```
ATGGTTAAAA AAGGCAAAAT TGCGCTTTTC TTTCTCATTA TTGCGTTGTT    50
TGCTTCTGGA ATTGCCTATT TTGCAAAGCC TGTTGTAAAC GACGTCAGCC   100
TTGGGCTTGA CCTGCAAGGC GGCTTTGAAG TGCTCTACGA AGTGGAGCCA   150
ATGAATGAGG GCGATGAAAT TAATCAGGAT TCGCTTTTAG CAACAACGAC   200
TGCATTGAAT GAAAGGGTAA ATACAATTGG CGTTTCAGAA CCGAACATCC   250
AAATTGAAGG AGAAAATCGC ATCCGTGTCC AGTTAGCTGG CGTTGAAGAC   300
CAAGAAACAG CACGTGACAT TTTAGCGACT GGCGCAGAAT TGACGATCCG   350
TGACGTCGAT GACAACGTGC TTCTTGATGG CAGCGATTTA ACCCAAAATG   400
GCGCCAGCGC ATCGGTACAT CCAGAAAAAA ATCAGCCGAT TGTCACATTG   450
ACGCTAAATG ATGCAGACAA ATTTGGCGAA ATCACACGTG AAATTTCCGA   500
ACGCCCACTA GGAGAGAATT TGCTCGTCAT CTGGCTTGAC TTTGAGGAAG   550
GCGACAGCTT TGCAGAAGAA TCAAAAAAAC AAGACCCTAA ATACATGTCA   600
GCAGCGTCCG TTAATGCCCC GTTACATACA CGAGACGTGA TGATCGAAGG   650
GAACTTTACA ACTGAGGAAA CACGCTTTCT TGCTGAAATA TTAAATGCAG   700
GCGCTTTGCC TGTTGAGTTA AATGAGATCT ACTCTACATC AGTCGGTGCA   750
TCGCTAGGGG AAAAAGCGAT GAACCAAACG ATTTTTGCTG GCTCCCTTGG   800
GGTTGGGCTG ATCTTTTTGT ATATGGTTGT TTACTATCGC TTTCCAGGAA   850
TCATCGCTGT CATAACACTA AGCATTTATA CATTTTTGGT GCTTGTCGTC   900
TTTAATGCCA TGAATGCTGT GTTAACTTTG CCAGGCATTG CCGCGCTCGT   950
GCTTGGTGTG GGCATGGCTG TCGATGCGAA TATCATTACT TATGAACGGA  1000
TTAAGGAAGA GATTAAATCA GGGAAATCGA TTTTATCTGC CTTTAAAGTC  1050
GGCAGCAGAC GCTCGTTTGC AACGATTTTT GATGCCAATA TCACGACGTT  1100
GATTGCGGCT GGCGTCATGT TTTATTTTGG GACGAGCTCT GTGCAAGGCT  1150
TTGCAGTCAT GCTCATTATT AGCATTCTTG TCAGCTTTTT AACGGCTGTC  1200
TATGGTTCCA GGGTGTTGCT AGGCCTCTGG GTAAACAGCA AATTTTTAAA  1250
TAAACGGCCT GGCTGGTTTG GCGTGAAAAG AGGTGAAATT GATGAGCTT   1299
```

Figure 12

*B. clausii* secE partial aa sequence
MADENKGPVT FLRNVGREMK RVTWPTK 27

Figure 13

*B. clausii secE* partial DNA sequence
ATGGCAGATG AAAACAAAGG ACCAGTTACT TTTCTTCGGA ATGTAGGCAG 50
GGAAATGAAA CGCGTAACAT GGCCAACTAA A 81

Figure 14

*B. clausii* secF aa sequence

```
MSFNPEKWNV DLTKHRKRFF IGSGLSMVLG IVLLLTFGLN LGVDFESGSN    50
VEIQADQTLT QEQLLDDFAA INESYTPNIT LGGEQSQSAT ARFTVELSKD   100
EITTIQTYFQ DKYGHSPNVS TVSPLVGQEL ARNAILSVLI ASIGIVIYIG   150
LRFXYLYGVS AVIGLLHDAF IIIALFSLFQ VEINVPFIAA VLTVVGYSIN   200
DTIVTFDRMR ENINKEKEIN SFEHLAQIVN KSLLQVLTRS INTVLTVLFA   250
AVALLIFGGE AIRSFSLALV IGLIAGTYSS MFLCAQMWLV WEWKRQKKLK   300
NKPKKTEEEY I                                             311
```

Figure 15

*B. clausii secF* DNA sequence

```
ATGAGCTTTA ATCCGGAAAA GTGGAATGTC GATTTGACAA AACACCGAAA    50
ACGTTTTTTT ATCGGCTCGG GCTTGTCAAT GGTCCTTGGA ATTGTGTTGT   100
TGCTGACATT TGGTTTAAAT TTAGGCGTTG ATTTTGAAAG TGGTTCAAAT   150
GTGGAAATCC AAGCGGATCA GACATTGACG CAAGAACAAT TACTGGACGA   200
CTTTGCAGCA ATCAATGAAT CGTACACGCC GAATATTACA CTTGGAGGCG   250
AGCAAAGCCA AAGTGCGACT GCCCGGTTTA CAGTCGAACT TTCCAAAGAT   300
GAAATTACCA CGATCCAGAC GTATTTCCAA GACAAATACG GGCATTCGCC   350
TAACGTCAGT ACAGTGTCGC CCCTTGTCGG CCAGGAACTC GCTCGCAATG   400
CGATTTTGTC TGTATTGATC GCTTCGATCG GAATCGTTAT TTACATCGGT   450
CTCCGCTTTC MCTACCTTTA TGGCGTTTCA GCGGTTATCG GCTTGCTCCA   500
CGATGCCTTT ATCATTATTG CGTTGTTTAG CTTGTTCCAA GTTGAAATTA   550
ATGTTCCTTT TATAGCAGCA GTGCTCACTG TTGTCGGCTA CTCAATCAAT   600
GACACCATTG TTACGTTTGA CCGCATGCGG GAAAATATTA ACAAGGAGAA   650
GGAAATTAAC AGCTTTGAGC ACTTGGCGCA AATTGTCAAC AAAAGCTTGC   700
TGCAAGTGTT AACACGCTCG ATCAATACGG TATTGACCGT ACTATTTGCC   750
GCTGTGGCAT TGCTGATATT CGGCGGCGAA GCGATCCGCT CGTTTTCATT   800
GGCTTTAGTC ATTGGTTTGA TTGCCGGTAC TTATTCTTCG ATGTTCCTTT   850
GTGCGCAAAT GTGGCTTGTC TGGGAATGGA AACGGCAAAA GAAACTAAAA   900
AACAAACCAA AGAAAACGGA AGAAGAGTAC ATT                     933
```

Figure 16

*B. clausii* secG partial aa sequence

```
QPGRSSGLSG AITGGAEQLL GKQKARGLDA VLHRATIVLA VLFFILTGLN AYFL        54
```

Figure 17

*B. clausii secG* partial DNA sequence

```
TTGCAGCCAG GTCGCAGCTC TGGGTTATCG GGCGCCATTA CTGGAGGGGC        50
AGAGCAGTTG CTAGGAAAAC AAAAAGCGCG CGGGCTTGAT GCGGTATTGC       100
ATCGAGCAAC AATCGTACTT GCTGTTTTGT TTTTTATTTT GACAGGGTTA       150
AATGCGTATT TCCTA                                             165
```

Figure 18

*B. clausii secY* aa sequence

```
MFKAISNIFR VRDLRRKIVF TLLMLIVFRI GAFIPVPGTN SDALEMLFGG    50
ANAFGFLDTF GGGALSNFSI FAMGIMPYIT ASIVVQLLQL DVVPKFAEWA   100
KQGEAGRKKL TQVTRYGTIV LGFVQAIAMS VGFNSMYQGA GPGLIENPSV   150
MTYVYIAIVL TAGTAFLMWL GEQITAHGVG NGISLIIFAG IAAGVPNMLN   200
ALYTSEIEGA GDQLFLSIAT VALLALIVLL IIIGVIYVHQ ALRKIPVQYA   250
KRVVNRSQVG GQSTHLPIKV NAAGVIPVIF ASALFYFPST IASFVGPDDK   300
AWARWIVEHF VPSSWIGGSI FVVLIIAFTY FYTFVQVNPE KMADNLKRQG   350
GYIPGIRPGQ ATQSFITKIL YRLTFVGALF LATIATIPVV FIALLDLPQQ   400
VQIGGTGLLI IVGVALDTMK QIEGQLIKRS YKGFIN                  436
```

Figure 19

*B. clausii secY* DNA sequence

```
ATGTTTAAGG CGATCTCCAA CATCTTCCGT GTGAGAGATT TACGTCGAAA    50
AATCGTCTTT ACGCTTCTGA TGCTTATTGT TTTTCGAATC GGCGCATTCA   100
TACCCGTGCC AGGCACGAAC AGTGATGCGC TTGAGATGCT TTTTGGCGGA   150
GCTAATGCTT TTGGGTTTCT CGATACCTTT GGCGGCGGCG CACTAAGCAA   200
CTTCTCGATT TTTGCAATGG GGATCATGCC TTACATCACA GCCTCGATCG   250
TTGTTCAGCT TCTTCAACTG GATGTAGTGC CGAAGTTTGC AGAATGGGCG   300
AAACAGGGCG AGGCTGGTCG GAAAAAGCTA ACGCAAGTAA CTCGATATGG   350
TACGATTGTT TTAGGGTTTG TCCAAGCGAT CGCCATGTCA GTCGGTTTTA   400
ATTCAATGTA TCAAGGAGCA GGCCCTGGCT TGATTGAAAA TCCATCTGTG   450
ATGACGTACG TCTATATCGC CATCGTCCTT ACAGCAGGTA CAGCATTTTT   500
AATGTGGCTA GGGGAGCAGA TTACAGCTCA CGGTGTAGGG AATGGAATCT   550
CGCTCATTAT CTTTGCAGGT ATTGCAGCCG GCGTTCCAAA CATGCTGAAT   600
GCTTTATATA CATCTGAAAT TGAAGGCGCA GGCGACCAGT TGTTTTTGAG   650
CATCGCCACC GTTGCATTGC TCGCTTTAAT CGTTTTACTG ATTATCATTG   700
GCGTCATTTA CGTGCACCAA GCCTTGCGGA AAATACCTGT CCAATATGCG   750
AAGCGCGTCG TCAATCGCAG CCAAGTAGGC GGACAGTCAA CGCATTTGCC   800
GATTAAAGTG AACGCTGCAG GGGTCATTCC GGTCATCTTT GCCTCAGCAT   850
TGTTTTATTT TCCGTCAACC ATTGCTTCAT TTGTTGGGCC AGATGACAAG   900
GCATGGGCAA GATGGATTGT GGAACATTTC GTGCCGAGTT CATGGATCGG   950
CGGCAGCATT TTTGTTGTCT TGATTATCGC GTTTACGTAT TTTTACACAT  1000
TTGTACAGGT TAACCCGGAA AAAATGGCCG ATAATTTGAA ACGGCAAGGC  1050
GGGTATATCC CTGGCATTCG TCCTGGTCAA GCAACGCAGT CTTTTATCAC  1100
GAAAATTTTA TATCGGCTTA CGTTCGTTGG CGCTCTATTC CTTGCGACCA  1150
TCGCAACGAT ACCGGTTGTG TTTATTGCGC TACTTGACTT GCCGCAGCAA  1200
GTGCAAATTG GCGGCACGGG CTTGTTAATC ATCGTCGGCG TTGCGCTAGA  1250
TACGATGAAA CAAATCGAAG GGCAGCTCAT TAAACGTTCG TATAAAGGCT  1300
TCATTAAC                                                1308
```

Figure 20

B. subtilis
nifS
yrxA
pheA
pheB
obg
spo0B
rpmA
rplU
ysxB
spoIVFB
spoIVFA
minD
minC
B. clausii
contig245
Inverse PCR closure
contig372
g1728 (yrxA C-term)
pheA
pheB
obg
spo0B
g2987
g2986
(BH1206)
hemY
hemH
hemE
B. halodurans
nifS
BH1216 (yrxA)
pheA
pheB
obg
spo0B
BH1211
BH1210
BH1209
ABC transporter
unknown
BH1208
BH0434
transposase
BH1206,1205,hemY,H,E Out
Membrane
In
pre -PhrC
pre -PhrA
pre -PhrE
Sec
Opp
ComP
KinB
ComA~P
ComA
RapC
RapA
RapE
PhrC
PhrA
PhrE
SpoOF~P
SpoOF
SpoOB
SpoOB~P
SpoOA~P
SpoOA
SpoOE
KinA
Comp genes
spo0A
sigH
AbrB
Anti -microbials
Proteases

Figure 23

```
SpoOF
                                  ____helix 1____                                                                                                        loop4
                                      !         !                                              Pi                                                        ####
Bsu        MMNEKILIVD DQYGIRILLN EVFNKEGY T FQAA GL AL DI TKER D  VLLDMKIPGM DGIEILKEMK VIDENIRVII MTAYGELDMI QESKELGALT
Bclausii   -MSHKVLIVD DQFGIRVLLT EVLQKDGYEL FQAASGKEAL AIQEEEEIDI VLLDMKIPGM DGIEILKKLK EKQPGIKVIM MTAYGELNLV NEAMDHGAVS
Bhalo      -MI-KILVVD DQYGIRVLLN EILQKDGY M FQAA GI AL AI EEET D  VLLDMKIPGM DGLEILRRIK DMNPNIEVIM MTAYGELNMI NEAMQLGAVT
            *  * * ** ** *** **  *   * **   **** *  **  *   *  *  ********** ** ***    *        * **  *******    *    **

              ____helix 5____
                $$
Bsu        HFAKPFDIDE IRDAVKKYLP LKSN
Bclausii   YMAKPFDIQE VRATIRDNLQ A---
Bhalo      HFAKPFDIDD VRAVIAENMK SS--
             ******     *

SpoOB
                                             Pi       ! $   $$ !                       #  ##  #                                                     ##
Bsu        MKDVSKNQEE NISDTALTNE LIHLLGHSRH DWMNKLQLIK GNLSLQKYDR VFEMIEEMVI DAKHESKLSN LKTPHLAFDF LTFNWKTHYM TLEYEVLGEI
Bclausii   MRS------- -------NDE LIRILGSIRH DWLNVLQLIK GNLAIGNQER AEAVLEEAVE QTTNESRLCN IGMPKTALVL LEQKWHQSAY EIAYEVDGPL
Bhalo      MTS------- -------KKD MLDVLRHSRH DWLNVIQLIK GYLALERYDR IEEVLEIAIQ QALNESKLSN LSIPNVSCYL LTFNWLQPPY TLEFEVMGEV
           *                          *    ** ** *  **** * *       *        *          ** * *     *        *   *          ** *

Bsu        KDLSAYDQKL AKLMRKLFHL FDQAVSRESE NHLTVSLQTD HPDRQLILYL DFHGAFADPS AFDDIRQNGY EDVDIMRFEI TSHECLIEIG LD-----
Bclausii   LNLAKYDNAF STCFARFFSL LSEWPQLDGP SSVFVTYT-- FFDQNCLIEL DYQGHIYRSA SISNCFSEMP PSVVVDVTRQ EQAGYTVTFL LDATASN
Bhalo      TDLQSIEQEL ESLVRAAADL FKAHCSLERE NHLLLTFQ-L FPD-FLRLTF DFQGKLCRLE ELETALKHVL QKREDS-FEL REEECVFSVC FEKK---
             *                *                                 *        *  *

SpoOA
                          !        !                                          Pi                                                    ### #
Bsu        MEKIKVCVAD DNRELVSLLS EYIEGQEDME VIGVAYNGQE CLSLFKEKDP DVLVLDIIMP HLDGLAVLER LRESDLKKQP NVIMLTAFGQ EDVTKKAVDL
Bclausii   MSNVTVCIAD DNRELVHLLS EYVGAQPDME VIGTAFNGQE CLTVVEEKMP DVLLLDIIMP HLDGLAVLER LSQR--EKKP QIIMLTAFGQ EDVTKRAVDF
Bhalo      MQKVKVCIAD DNRELVNLLN DYVSAQDDME VVGVAFNGQE CLSIVEERQP DVLILDIIMP HLDGLAVLEK LPYMNLQTKP NIIMLTAFGQ EDVTKKAVDL
           *     ** ** ****** **    *    * *** * * * **** **      *  * *** ****** *********  *          *   ******** ***** ***
                      $$
Bsu        GASYFILKPF DMENLVGHIR QVSGNASSVT HRAPSSQSSI IRSSQPEPKK KNLDASITSI IHEIGVPAHI KGYLYLREAI SMVYNDIELL GSITKVLYPD
Bclausii   GASYYVLKPF DMDALMEKIR EIGG--SKKA KRTRTSSLSF HTAPRPEERQ VNLDASITSI IHEIGVPAHI KGYMYLREAI TMVYKDIELL GSITKVLYPD
Bhalo      GASYYVLKPF DMEILINNIR EVSGQKRSFV QNTASNHSSF AQPKKPEANV FNLDASITNI IHEIGVPAHI KGYMYLREAI TMVYNDIELL GSITKVLYPD
           ****  **** **  *   **    *                 *         **        ******* * ********** *** ******  *** ***** **********

             ___H-T-H_________________
Bsu        IAKKFNTTAS RVERAIRHAI EVAWSRGNID SISSLFGYTV SMTKAKPTNS EFIAMVADKL RLEHKAS
Bclausii   IAKKFNTTAS RVERAIRHAI EVAWSRGNID SISNLFGYTV SQSKAKPTNS EFIAMVADKL RIEHKVS
Bhalo      IAKKFNTTSS RVERAIRHAI EVAWSRGNID SISNLFGYTV SVSKAKPTNS EFIAMVADKL RIEHKVS
           ********  * ********** ********** *** ****** *  ******* ********** * *** *
```

*B. clausii* SipS aa sequence

```
MAFRGFPIEW AKAICIALCA TMLVRLFLYA PIVVDGHSMQ PTLDSGDKMI    50
VNQIGYVFIE PQRFDIVVFH APGGKDYIKR IIGLPGDHLK YENDTLYING   100
EETAEPYLNS LKQTLYGDQL LTGDFTLEEL IGEEVIPDDH YFMMGDNRRL   150
SKDSRDIGLI PKSEIIGKAN VIFYPFEHIS IVND                    184
```

Figure 25

*B. clausii* SipS DNA sequence

```
GTGGCATTTC GCGGATTTCC AATTGAGTGG GCCAAAGCCA TTTGCATCGC    50
GTTATGCGCC ACAATGCTCG TACGCCTTTT TTTGTACGCG CCCATTGTTG   100
TAGACGGCCA TTCGATGCAG CCAACGCTCG ACTCTGGGGA CAAAATGATC   150
GTCAACCAAA TTGGGTATGT TTTTATTGAG CCACAACGTT TTGATATTGT   200
TGTTTTCCAC GCACCTGGCG GGAAAGATTA TATTAAACGG ATCATTGGCC   250
TCCCTGGCGA CCATTTGAAA TATGAAAACG ATACGCTTTA TATTAACGGG   300
GAAGAAACAG CGGAACCTTA TTTAAACTCG CTGAAACAGA CGCTTTACGG   350
CGACCAATTG CTTACTGGCG ATTTTACACT GGAAGAGTTA ATCGGCGAAG   400
AGGTAATACC TGACGATCAT TATTTTATGA TGGGCGATAA TCGCCGTTTA   450
AGTAAAGACA GCCGTGATAT TGGTCTCATT CCGAAATCAG AAATTATCGG   500
CAAAGCCAAC GTCATTTTTT ATCCGTTTGA ACATATAAGC ATTGTTAACG   550
AT                                                       552
```

Figure 26

*B. clausii* SipT aa sequence

```
MADAKRNSEF WGWVKTIAIA FILAVGIRTF VIERFEVQGA SMVPTAHDGE   50
HFIIDKWSYQ FGEPERFDLI VFQATEEDRY IKRVIGLPGD TIRFENDILY  100
INGEQIEEPY LQEAKAAYSG PVYTEDYSFE EAVPENHVFV MGDNRPTSLD  150
SRTIGPVSED KIIGKVGLRF WPLPEFDVQ                         179
```

Figure 27

*B. clausii SipT* DNA sequence

```
GTGGCGGACG CAAAAAGAAA TTCAGAGTTT TGGGGTTGGG TAAAGACGAT   50
TGCCATTGCC TTTATTCTTG CGGTTGGAAT CCGGACATTT GTGATTGAAC  100
GTTTTGAGGT TCAAGGCGCC TCAATGGTGC CGACTGCTCA TGACGGTGAA  150
CATTTTATTA TCGATAAATG GAGTTATCAA TTCGGCGAGC CGGAACGGTT  200
TGATCTCATT GTGTTCCAAG CAACGGAAGA AGACCGCTAC ATCAAACGGG  250
TGATTGGCTT ACCAGGCGAT ACGATTCGGT TTGAGAACGA CATTCTTTAC  300
ATTAATGGCG AACAAATCGA AGAACCTTAT TTGCAAGAAG CAAAAGCTGC  350
TTATTCAGGG CCTGTGTATA CGGAAGATTA CTCATTTGAA GAGGCTGTCC  400
CAGAAAACCA TGTGTTTGTA ATGGGTGATA ACCGCCCTAC TAGCTTAGAC  450
AGCCGCACTA TTGGCCCAGT TAGCGAAGAT AAAATTATCG GCAAAGTCGG  500
ATTGCGGTTC TGGCCGCTGC CTGAATTTGA CGTACAA                537
```

Figure 28

*B. clausii* SipV aa sequence

```
MLMNGRRKRG TAVAEAEKKS EFWGGVKAIA IALILAFVVR TFVMTSFEVR   50
GVSMVPTAHD GERFIVNKLS YQFGEPERFD LIVFHATEED SYIKRVIGLP  100
GDTIRFEDDI LYINGEQVEE PYLEEAKAAY SGPAYTEDYS FEETVPENHV  150
FVMGDNRPAS LDSRVIGPVN EDEIIGKVGL RFWPVSEFGF MD          192
```

Figure 29

*B. clausii SipV* DNA sequence

```
ATGCTCATGA ATGGAAGACG AAAGCGAGGA ACAGCAGTGG CAGAAGCGGA   50
AAAGAAATCA GAGTTTTGGG GCGGGGTAAA GGCGATTGCA ATTGCGCTAA  100
TTCTTGCGTT TGTAGTCCGG ACATTTGTGA TGACCAGCTT TGAAGTTCGC  150
GGCGTCTCAA TGGTGCCGAC TGCTCATGAT GGTGAGCGTT TTATTGTAAA  200
TAAATTAAGT TACCAATTTG GCGAGCCTGA GCGGTTTGAT CTCATTGTGT  250
TCCACGCGAC GGAGGAAGAT AGCTATATCA AACGGGTGAT TGGCTTACCA  300
GGCGATACCA TTCGATTTGA GGACGACATC CTTTACATTA ATGGCGAGCA  350
AGTCGAAGAG CCTTATTTAG AAGAAGCAAA AGCTGCTTAT TCAGGGCCCG  400
CGTATACGGA AGATTACTCA TTTGAAGAAA CCGTCCCAGA GAACCATGTC  450
TTTGTAATGG GTGACAACCG CCCTGCTAGC TTAGACAGCC GTGTCATTGG  500
CCCGGTTAAT GAAGATGAAA TCATCGGCAA AGTCGGATTG CGGTTCTGGC  550
CGGTGTCTGA ATTTGGCTTT ATGGAT                            576
```

Figure 30

*B. clausii* SipW aa sequence

```
MVNMWITIGK LAITGIASFL FFLVLFFVLQ GKGSDGRGPE LFGWTSYTIL    50
SNSMEPTFSA GDVVIMKKNE EPSIGDVVTF MAPERRLFTH RIIEKFESNG   100
KTYYKTQGDN NNVVDEDPIV KEQIVGTHMF TIPKVGLVAE KINQPIGYGL   150
LIVVPIAGYL LLSFYETIQK KRKEAS                             176
```

Figure 31

*B. clausii SipW* DNA sequence

```
ATGGTCAACA TGTGGATAAC AATCGGAAAA TTGGCGATTA CCGGGATTGC    50
ATCGTTTTTG TTCTTCCTCG TTCTCTTTTT TGTCCTTCAA GGAAAGGGCA   100
GTGACGGCAG AGGACCTGAG CTGTTTGGCT GGACAAGCTA TACCATCTTG   150
TCCAACAGCA TGGAGCCGAC ATTTTCCGCC GGAGATGTGG TCATCATGAA   200
AAAGAATGAG GAGCCTAGCA TTGGCGATGT TGTAACGTTT ATGGCTCCTG   250
AACGGCGCTT GTTCACACAC CGGATTATTG AGAAGTTTGA AAGCAATGGA   300
AAGACGTATT ATAAGACGCA AGGCGATAAC AACAACGTTG TAGACGAAGA   350
CCCAATCGTA AAAGAACAAA TTGTCGGCAC CCATATGTTC ACCATTCCTA   400
AAGTGGGTTT AGTTGCTGAA AAAATCAATC AACCAATTGG TTATGGTTTG   450
TTGATTGTCG TGCCGATTGC TGGGTATTTG CTGTTATCGT TCTACGAAAC   500
CATCCAAAAA AAACGTAAGG AGGCTTCT                           528
```

Figure 32

*B. clausii* Bcl 2627 aa sequence
MELGKTIKYYRIKHNMTQAELADGICSIPHLSKIENNIYKANHATASLLLDRLGVNIEDE
YAQHNEIKQSLEAFIEAIQFVDVQEAKRIQKILVEKEFIIARTDYINTYHLYMMRYHLMN
GANHLAQEQRAILDKNRTNLSAIEELSYRLFNGILLVNRNRLKEAKEILLDLQSEDYSSK
YIFVREVAFVLAQCFTQLNEPEKAIIYAKEALQIFKQEDNYIRAFHTQMLLGVNYTQMNM
TEESLRLYKILLRNTRLFSRDTLYYQAMYNYGVLLKKIGNYEQSHECFTKCSAYYDKDSQ
NYVFSLLADIEVLFQLKTDKKQIESKLNEIIEISAKRGYKRSELQARYYAHRLKADDAMY
NFIEQELLPHLDKLDNKEEPVHYAIELAQWYQKNGEYEKANEYLNKYAMKVKRREFSIV

Figure 33

*B. clausii Bcl 2627* DNA sequence
GTGGAGTTAGGCAAAACAATCAAATACTACCGAATTAAGCATAATATGACACAGGCAGAA
CTCGCTGATGGTATTTGCTCCATTCCACACCTTAGCAAAATTGAAAACAACATCTATAAG
GCCAACCATGCTACAGCTTCCCTCTTGCTTGACCGGCTTGGCGTCAATATAGAAGATGAA
TATGCCCAACACAACGAGATTAAGCAGTCGCTGGAAGCCTTTATTGAAGCGATACAATTT
GTGGATGTACAGGAAGCAAAACGGATACAAAAAATATTAGTCGAGAAGGAATTTATCATT
GCCCGAACGGATTACATTAATACGTACCATTTATACATGATGCGCTACCACTTGATGAAC
GGAGCGAACCACCTTGCCCAAGAACAGCGAGCCATCTTAGATAAAAACCGCACGAATTTG
TCCGCGATCGAAGAACTGTCTTACCGTCTGTTCAATGGCATCCTCCTAGTAAACCGCAAC
CGCTTAAAGGAAGCAAAAGAAATTTTGCTTGACTTGCAAAGTGAAGACTATTCTTCCAAA
TACATTTTTGTCCGTGAAGTCGCTTTCGTGCTTGCACAGTGTTTTACACAGCTAAATGAG
CCAGAAAAAGCAATCATTTATGCAAAAGAGGCGCTCCAAATTTTTAAGCAAGAGGACAAT
TACATTCGCGCTTTTCACACGCAAATGTTGCTAGGGGTCAATTATACACAAATGAATATG
ACAGAGGAATCCCTTCGCCTCTATAAAATCCTTTTGCGAAACACACGCTTGTTTAGCCGC
GACACGCTCTATTACCAAGCCATGTACAATTACGGCGTCTTGCTTAAAAAAATTGGCAAC
TATGAACAAAGCCATGAATGTTTTACGAAATGCAGCGCTTATTACGACAAAGACAGCCAA
AATTACGTATTCAGCCTTCTCGCAGACATCGAAGTTCTCTTCCAGTTGAAAACGGACAAA
AAACAAATTGAATCAAAATTAAATGAAATTATTGAAATTAGTGCAAAACGTGGGTACAAA
CGCTCTGAGCTTCAAGCCCGCTACTATGCGCACCGCTTAAAAGCCGACGATGCGATGTAC
AACTTTATCGAACAGGAACTGCTCCCTCATCTCGATAAGCTTGATAATAAAGAAGAACCA
GTCCACTATGCAATTGAGCTGGCGCAATGGTACCAGAAAAACGGAGAGTACGAAAAAGCA
AACGAATACTTAAATAAATATGCCATGAAAGTCAAAAGACGTGAATTTTCCATTGTATAG

Figure 34

SEQUENCE LISTING

<160> NUMBER OF SEQ ID NOS: 32

<210> SEQ ID NO 1
<211> LENGTH: 840
<212> TYPE: PRT
<213> ORGANISM: Bacillus clausii

<400> SEQUENCE: 1

```
Met Ile Ser Lys Val Ile Lys Thr Ser Glu Glu Met Gly Thr Ala Lys
 1               5                  10                  15

Val Ala Glu Lys Leu Asn Gly Ile Trp Thr Lys Cys Ala Ser Ser Gly
            20                  25                  30

Gln Ala Leu Lys Ser Gly Ala Lys Thr Val Leu Tyr Asp Trp Gly Ile
        35                  40                  45

Phe Ile Ala Ile Leu Gly Phe Leu Leu Gly Arg Ala Met Ile Leu Ser
    50                  55                  60

Glu Leu Thr Pro Phe Ile Leu Pro Phe Leu Ala Ala Val Phe Leu Leu
65                  70                  75                  80

Arg Arg Ser Gln Ser Leu Ile Ala Ala Ala Ser Leu Leu Ala Gly Ala
                85                  90                  95

Val Phe Ser Phe His Gly Gln Leu Ile Phe Ala Ile Ala Gly Ile Gly
            100                 105                 110

Phe Phe Leu Ile Leu Tyr Lys Cys Met Lys Met Phe Met Lys Tyr Pro
        115                 120                 125

Ala Lys Ser Leu Pro Tyr Leu Val Phe Ser Ala Ser Ile Ala Thr Arg
    130                 135                 140

Leu Ser Leu Val Phe Leu Thr Glu Gly Gly Leu Ser Gln Tyr Ala Met
145                 150                 155                 160

Met Met Ala Thr Val Glu Ala Ala Leu Ser Phe Ile Leu Thr Met Ile
                165                 170                 175

Phe Ile Gln Ser Ile Pro Leu Val Thr Gly Lys Arg Gly Gly Gln Ala
            180                 185                 190

Leu Arg Asn Glu Glu Ile Ile Cys Leu Ile Ile Leu Leu Ala Ser Val
        195                 200                 205

Met Thr Gly Thr Val Gly Trp Thr Ile Asn Glu Ala Val Leu Gln His
    210                 215                 220

Ser Phe Ala Ser Tyr Leu Val Leu Val Phe Ala Phe Val Gly Gly Ala
225                 230                 235                 240

Ala Ile Gly Ser Thr Val Gly Val Val Thr Gly Leu Ile Leu Ser Leu
                245                 250                 255

Ala Ser Leu Ala Ser Leu Tyr Gln Met Ser Leu Leu Ala Phe Ala Gly
            260                 265                 270

Leu Leu Gly Gly Leu Leu Lys Glu Gly Lys Arg Ile Gly Val Ser Leu
        275                 280                 285

Gly Leu Leu Val Gly Thr Leu Leu Ile Gly Met Tyr Gly Gln Gly Gly
    290                 295                 300

Gly Leu Gly Ala Ser Val Ser Glu Ser Ala Ile Ala Ile Thr Leu Phe
305                 310                 315                 320

Leu Leu Thr Pro Lys Ser Trp Leu Thr Lys Val Ala Arg Tyr Ile Pro
                325                 330                 335

Gly Thr Val Glu His Ser Gln Glu Gln Gln Gln Tyr Leu Arg Lys Val
            340                 345                 350

Arg Asp Ala Thr Ala Gly Lys Val Glu Arg Phe Ser Ser Leu Phe Gln
```

-continued

```
        355                 360                 365

Thr Leu Ser Asn Ser Phe His Thr Pro Ser Lys Asn Glu Glu Glu Glu
    370                 375                 380

His Asp His Glu Val Asp Val Leu Leu Ser Arg Val Thr Glu Lys Thr
385                 390                 395                 400

Cys Gln Thr Cys Met Leu Lys Glu Lys Cys Trp Val Gln Asn Phe Asn
                405                 410                 415

Ala Thr Tyr Asp Ser Met Lys Gln Met Val Gln Glu Ser Glu Val His
            420                 425                 430

Gly Thr Val Val Asp Pro Lys Leu Gln Arg Gln Trp Arg Ser His Cys
        435                 440                 445

Arg Lys Pro Asp Gln Val Met Ala Ala Leu Asn Ala Glu Val Asn His
    450                 455                 460

Tyr Arg Ala Asn Lys Glu Leu Lys Arg Gln Val Leu Glu Ser Gln Arg
465                 470                 475                 480

Leu Val Ala Asp Gln Leu Leu Gly Val Ser Arg Val Met Gly Asp Phe
                485                 490                 495

Ala Lys Glu Ile Gln Lys Glu Lys Gln Pro His Val Ile Gln Glu Glu
            500                 505                 510

His Met Val Asp Ala Leu Arg Asn Ala Gly Leu Glu Val Gly His Ile
        515                 520                 525

Asp Ile Tyr Ser Met Glu Ser Gly Ser Ile Glu Ile Glu Met Ser Val
    530                 535                 540

Leu Cys Ser His Glu Asn Gly Glu Ala Glu Lys Ile Ile Ala Pro Met
545                 550                 555                 560

Leu Ser Asp Leu Val Lys Glu Thr Ile Val Leu Met Arg Glu Glu Pro
                565                 570                 575

Gly Phe Tyr Ser Asn Gly Tyr Ser His Ile Ser Phe Gly Ser Ala Lys
            580                 585                 590

Pro Phe Ala Val Glu Thr Gly Ile Ala Lys Val Ala Lys Gly Gly Glu
        595                 600                 605

Trp Leu Ser Gly Asp Asn Tyr Ala Met Ile Lys Leu Asn Ser Glu Lys
    610                 615                 620

Phe Ala Val Ala Ile Ser Asp Gly Met Gly Asn Gly Glu Lys Ala His
625                 630                 635                 640

Leu Glu Ser Ser Glu Thr Leu Lys Leu Leu Gln Lys Val Leu Gln Ser
                645                 650                 655

Gly Ile Glu Glu Thr Val Ala Ile Lys Ser Val Asn Ser Ile Leu Ser
            660                 665                 670

Leu Arg Asn Thr Glu Glu Met Phe Ser Thr Leu Asp Leu Ala Met Ile
        675                 680                 685

Asp Met Gln Asp Ala Gly Ala Lys Phe Leu Lys Ile Gly Ser Thr Pro
    690                 695                 700

Ser Phe Ile Lys Arg Lys Asp His Val Ile Lys Ile Glu Ala Gly Asn
705                 710                 715                 720

Leu Pro Met Gly Ile Leu His Glu Phe Glu Val Asp Val Val Ser Glu
                725                 730                 735

Gln Leu Lys Pro Gly Asp Leu Leu Ile Met Cys Ser Asp Gly Val Phe
            740                 745                 750

Asp Ala Lys Arg Gln Ile Glu Asn Lys Glu Gln Trp Met Lys Arg Met
        755                 760                 765

Ile Lys Glu Ile Glu Thr Asp Asp Pro Gln Glu Val Ala Asp Val Leu
    770                 775                 780
```

-continued

```
Leu Glu Lys Val Ile Arg Ser Glu Lys Gly Ile Val Ile Glu Asp Asp
785                 790                 795                 800

Met Thr Ile Val Val Thr Gln Leu Lys His Asn Thr Pro Lys Trp Ser
                805                 810                 815

Ser Ile Pro Ile His Pro Lys Thr Thr Lys Asn Lys Lys Thr Ala Pro
            820                 825                 830

Phe Tyr Lys Gln Ala Thr Gly Thr
        835                 840


<210> SEQ ID NO 2
<211> LENGTH: 2520
<212> TYPE: DNA
<213> ORGANISM: Bacillus clausii

<400> SEQUENCE: 2

atgatcagta aagtgataaa gacgtcagaa gaaatgggta cagcgaaagt agccgaaaag     60

ctaaacggca tatggaccaa atgtgcaagc agtggacaag cccttaaaag cggagccaaa    120

acggtgcttt atgattgggg catattcatt gccattcttg gttttctgct aggaagggct    180

atgattttat cagagttgac gccatttatc ttgccattct tggcggccgt gttcttgtta    240

agacgctctc aatcactcat tgctgcagct tcattattag caggtgctgt gttcagtttc    300

catggtcagt tgatttttgc gattgcaggg atcgggtttt ttcttattct gtacaaatgt    360

atgaaaatgt tcatgaagta ccctgctaaa tcgctccctt atcttgtgtt ttcagctagt    420

atcgccacga ggctgtcact cgtatttttg acagaaggtg gattaagcca atatgcgatg    480

atgatggcta cagtcgaagc ggcgcttagc tttatcctga caatgatctt tatccaaagc    540

ataccgcttg tgacaggaaa aagaggcgga caagcactcc ggaatgaaga aattatttgt    600

ttaattattt tgcttgcctc tgtaatgaca ggaacagtcg gttggacgat aaatgaagct    660

gtgcttcagc atagctttgc aagttatctc gttttagtgt ttgcttttgt tggcggggct    720

gcaataggct cgactgtcgg agtggtgaca ggcttgattt taagcttggc cagtttagca    780

agtctttatc agatgagtct gcttgccttt gcaggcttgt taggagggtt gttaaaggaa    840

gggaaacgga tcggcgtgtc acttggctta cttgtaggaa cgcttttaat tggcatgtat    900

ggccaagggg gcgggcttgg ggcaagtgtg tcagagtctg ccattgcgat cacgctattt    960

ttattgacgc caaagagctg gctgacgaaa gtagcacgct atattcctgg gacagttgag   1020

cattcccagg aacagcagca gtatttacgg aaagtccggg acgcgacagc gggaaaggtt   1080

gaacggtttt cgtctttatt ccaaacacta tcgaacagct ttcatacacc ttctaaaaat   1140

gaggaagaag agcatgacca tgaggtcgat gtcctcctta gccgcgtgac ggaaaaaaca   1200

tgccaaacgt gcatgttgaa agaaaagtgc tgggtgcaaa actttaatgc tacctatgat   1260

tcaatgaagc aaatggtcca ggaaagtgag gtgcatggaa cagttgtcga tccaaaatta   1320

caaaggcaat ggcgcagcca ttgccgcaag cctgaccaag tcatggctgc ccttaatgct   1380

gaagtgaacc attatcgggc aaacaaggaa ttgaagaggc aagtgttaga gagccaacgg   1440

ctagtcgccg accaattgct tggcgtttcc cgggtaatgg gtgatttcgc caaagaaatc   1500

caaaaagaaa agcaacctca tgtcatccaa gaagaacata tggtggatgc tttgagaaac   1560

gccggccttg aggttgggca tatagacatt tacagcatgg agagtggtag cattgaaatt   1620

gaaatgagtg ttttatgcag ccacgaaaat ggcgaggcgg aaaaaatcat cgcgcccatg   1680

ctttctgatt tagtcaagga aacgattgtg ttgatgcggg aagaaccagg cttttattca   1740
```

-continued

```
aatggatata gccatatttc atttgggtca gcaaagcctt ttgctgttga aacaggcatt   1800

gccaaagtcg ccaaaggcgg cgaatggctg tctggagaca attacgccat gatcaaatta   1860

aatagcgaaa agttcgcagt tgcgataagc gacggcatgg gcaacggcga aaaagcccat   1920

ttggaaagca gtgaaacgtt gaaattgctg caaaaagtgc tgcaatcagg aattgaagaa   1980

acagtggcaa tcaaatcagt caattccatc ttgtcattgc gcaacactga agaaatgttc   2040

tccaccctcg atctggcgat gatcgatatg caagatgcag gagcgaaatt cctgaaaatt   2100

ggatcaacac caagctttat taagcggaaa gatcacgtca taaaaattga agcaggcaac   2160

ttgccaatgg gcattctcca cgaatttgaa gtagacgttg ttagcgagca gcttaagcca   2220

ggtgacttgc tgattatgtg cagcgatggg gtgtttgatg cgaaaaggca aattgaaaac   2280

aaagagcagt ggatgaaacg tatgattaag gaaattgaaa ccgatgaccc ccaagaagtg   2340

gccgatgtgc tattagagaa agtcattcgt tcggaaaaag ggattgtgat tgaggatgac   2400

atgacgatcg ttgttactca gttgaaacat aatacgccga aatggtcttc gattccgatc   2460

catccgaaaa cgactaaaaa caagaaaacc gcgccgttct ataaacaggc aacaggcacg   2520


<210> SEQ ID NO 3
<211> LENGTH: 235
<212> TYPE: PRT
<213> ORGANISM: Bacillus clausii

<400> SEQUENCE: 3

Met Ile Thr Gln Glu Thr Gln Glu Ile Arg Ile Val Ile Ile Asp Asp
 1               5                  10                  15

His Pro Leu Phe Lys Glu Gly Val Lys Arg Ile Leu Ser Met Glu Glu
            20                  25                  30

Asn Phe Asn Val Val Ala Asp Gly Glu Asp Gly Ser Glu Val Ile Asp
        35                  40                  45

Leu Val Arg Gln His Gln Pro Asp Val Ile Leu Met Asp Ile Asn Met
    50                  55                  60

Pro Lys Thr Asn Gly Val Glu Ala Thr Lys Asp Leu Ile Lys Ala Phe
65                  70                  75                  80

Pro Lys Val Lys Val Ile Ile Leu Ser Ile His Asp Asp Glu Ser Tyr
                85                  90                  95

Val Ser His Val Leu Arg Thr Gly Ala Ser Gly Tyr Leu Leu Lys Glu
            100                 105                 110

Met Asp Ala Glu Ser Leu Val Glu Ala Val Lys Val Val Ala Ser Gly
        115                 120                 125

Gly Ala Tyr Ile His Pro Lys Val Thr Ser Asn Leu Ile Lys Glu Tyr
    130                 135                 140

Arg Arg Leu Ala Arg Gln Asp Glu Gln Tyr Gln Asp Ser Ile Gly Phe
145                 150                 155                 160

Arg Glu Val Glu Tyr Arg Lys Pro Leu His Ile Leu Thr Arg Arg Glu
                165                 170                 175

Cys Glu Val Leu Gln Leu Met Thr Asp Gly Gln Asn Asn Arg Ala Ile
            180                 185                 190

Gly Glu Ser Leu Tyr Ile Ser Glu Lys Thr Val Lys Asn His Val Ser
        195                 200                 205

Asn Ile Leu Gln Lys Met Asn Val Asn Asp Arg Thr Gln Ala Val Val
    210                 215                 220

Glu Ser Ile Lys Lys Gly Tyr Val Ile Val Arg
225                 230                 235
```

-continued

<210> SEQ ID NO 4
<211> LENGTH: 705
<212> TYPE: DNA
<213> ORGANISM: Bacillus clausii

<400> SEQUENCE: 4

```
atgattactc aagaaacaca agaaattcgc attgtcatta tagacgacca tccattgttt      60

aaagaagggg taaagcggat tttatcgatg gaggaaaatt ttaatgttgt tgcagatggg     120

gaagacggat cggaagttat cgatttggtt cgccaacatc agccagatgt cattttaatg     180

gatattaata tgccaaaaac gaatggcgtc gaagcaacaa aagacttgat caaggcattt     240

ccaaaagtga aagtaattat tctttcaatt catgatgatg agtcttatgt ttcccatgtg     300

ttacgtacag gagcctcagg ttacttatta aaagaaatgg atgcggaatc attggttgaa     360

gctgtaaaag tggtggcatc cggcggcgct tatattcatc caaaagtgac atcaaatttg     420

attaaagaat accgtcgcct tgcccgccaa gatgagcaat accaagactc gatcggtttc     480

cgtgaagtcg agtatagaaa gccgcttcat attttaacta ggagagagtg tgaagtgctt     540

cagcttatga cggatggaca aaacaaccgg gcaatcggcg agtcgcttta cataagcgag     600

aagacagtga aaaaccatgt tagcaacatt ttgcaaaaaa tgaacgtgaa cgaccgaacg     660

caagcagtgg tagagtccat aaaaaaagga tatgtcatcg ttcgc                     705
```

<210> SEQ ID NO 5
<211> LENGTH: 329
<212> TYPE: PRT
<213> ORGANISM: Bacillus clausii

<400> SEQUENCE: 5

```
Val Ser Phe Phe Lys Lys Leu Arg Glu Lys Met Ala Gln Gln Thr Asn
 1               5                  10                  15

Glu Val Ala Asp Lys Phe Lys His Gly Leu Glu Lys Thr Arg Thr Ser
            20                  25                  30

Phe Ser Gly Lys Ile Asn Glu Leu Val Ala Arg Tyr Arg Lys Ile Asp
        35                  40                  45

Glu Asp Phe Phe Glu Asp Leu Glu Glu Ile Leu Ile Gly Ala Asp Val
    50                  55                  60

Gly Val Ser Thr Val Met Glu Leu Val Asp Glu Leu Lys Glu Glu Val
65                  70                  75                  80

Arg Leu Arg Asn Leu Lys Asp Thr Glu Glu Ile Gln Pro Val Ile Ser
                85                  90                  95

Glu Lys Leu Ala Ser Leu Leu Glu Lys Asp Asp Lys Asp Thr Thr Leu
            100                 105                 110

Gln Leu Gln Glu Gly Leu Ser Val Ile Leu Val Val Gly Val Asn Gly
        115                 120                 125

Val Gly Lys Thr Thr Ser Ile Gly Lys Leu Ala His Tyr Leu Lys Gly
    130                 135                 140

Gln Gly Lys Ser Val Val Leu Ala Ala Gly Asp Thr Phe Arg Ala Gly
145                 150                 155                 160

Ala Ile Asp Gln Leu Asp Val Trp Gly Glu Arg Val Gly Val Pro Val
                165                 170                 175

Ile Lys Gln Gln Glu Gly Ser Asp Pro Ala Ala Val Met Tyr Asp Ala
            180                 185                 190

Ile Ala Trp Ala Arg Ser Arg Lys Ala Asp Val Leu Ile Cys Asp Thr
        195                 200                 205
```

-continued

```
Ala Gly Arg Leu Gln Asn Lys Val Asn Leu Met Asn Glu Leu Ala Lys
    210                 215                 220

Val Lys Arg Val Asn Glu Arg Glu Val Pro Gly Ala Pro His Glu Val
225                 230                 235                 240

Leu Leu Val Val Asp Ala Thr Thr Gly Gln Asn Ala Leu Ser Gln Ala
                245                 250                 255

Lys Ala Phe Ala Ala Ser Thr Asp Val Ser Gly Leu Val Leu Thr Lys
            260                 265                 270

Leu Asp Gly Thr Ala Lys Gly Gly Ile Val Ile Ala Ile Arg Gln Glu
        275                 280                 285

Leu Asp Leu Pro Val Lys Phe Ile Gly Leu Gly Glu Gln Lys Asp Asp
    290                 295                 300

Leu Gln Pro Phe Asp Ala Glu Gln Phe Val Tyr Gly Leu Phe Lys Asp
305                 310                 315                 320

Ala Ile Asp Ala Glu Lys Asn Asp Gln
                325
```

<210> SEQ ID NO 6
<211> LENGTH: 990
<212> TYPE: DNA
<213> ORGANISM: Bacillus clausii

<400> SEQUENCE: 6

```
gtgagctttt ttaaaaaatt gagagaaaaa atggcgcagc aaacgaatga agtagcggac     60

aaatttaaac atggattaga aaaaacacgg acaagctttt cgggcaaaat caatgagctt    120

gtcgcccgct accgtaaaat cgacgaagat ttctttgaag acttggagga aatcctgatt    180

ggcgccgatg tcggtgtttc aacagtaatg gaacttgttg acgaattaaa ggaagaagtg    240

cgtttgcgca acttaaagga caccgaagag atacagcctg tcatttccga aaaactagct    300

agtctcttag aaaaagacga taaagacaca acgctccaat tacaagaagg gttgagcgtc    360

attcttgttg ttggcgtaaa tggcgtcggc aaaacgacgt ccattggcaa gctcgcccat    420

tatttaaaag ggcaaggaaa atctgtcgtg ctcgccgctg gcgatacatt ccgagcgggt    480

gcgattgacc agcttgacgt ttggggagaa cgtgttggcg ttccagttat taaacagcaa    540

gaaggctctg acccggcggc ggtcatgtat gatgcgattg cttgggcacg ttcccgcaaa    600

gccgatgtgc ttatttgcga tacagcgggg cgcctgcaaa acaaagtcaa tttaatgaat    660

gagctggcaa aagtaaaacg cgtcaatgaa agggaagtgc caggagctcc ccacgaagta    720

ctgcttgtcg tcgatgcgac aacaggccaa aatgctttgt cgcaagcgaa agcatttgca    780

gcttcaactg acgtgagcgg ccttgtcctc acgaaacttg atggcacggc caaaggaggc    840

attgtcattg ccattcgcca agagcttgat ttgccagtta agtttatcgg gctaggtgaa    900

cagaaagacg atttgcagcc atttgacgct gagcaatttg tgtatgggct gtttaaggac    960

gcgatcgatg ccgaaaagaa tgaccagtga                                     990
```

<210> SEQ ID NO 7
<211> LENGTH: 379
<212> TYPE: PRT
<213> ORGANISM: Bacillus clausii

<400> SEQUENCE: 7

```
Met Ala Phe Glu Gly Leu Ala Ala Arg Leu Gln Asp Thr Leu Thr Lys
 1               5                  10                  15

Ile Arg Gly Lys Gly Lys Val Ser Glu Gln Asp Ile Lys Glu Met Met
            20                  25                  30
```

-continued

```
Arg Glu Val Arg Leu Ala Leu Leu Glu Ala Asp Val Asn Phe Lys Val
        35                  40                  45

Val Lys Gln Phe Ile Ala Asn Val Lys Glu Lys Ala Leu Gly Gln Glu
    50                  55                  60

Val Met Lys Ser Leu Thr Pro Gly Gln Gln Val Ile Lys Val Val Asn
65                  70                  75                  80

Glu Glu Leu Thr Ala Leu Met Gly Ala Glu Gln Ser Lys Ile Ala Val
                85                  90                  95

Ala Gln Lys Pro Pro Thr Val Val Met Met Val Gly Leu Gln Gly Ala
            100                 105                 110

Gly Lys Thr Thr Thr Thr Ala Lys Leu Ala Asn His Leu Arg Lys Lys
        115                 120                 125

His Asn Arg Lys Pro Leu Leu Val Ala Cys Asp Val Tyr Arg Pro Ala
    130                 135                 140

Ala Ile Gln Gln Leu Glu Thr Leu Gly Lys Gln Leu Asn Met Pro Val
145                 150                 155                 160

Phe Ser Lys Gly Thr Asp Ala Asn Pro Val Asp Ile Ala Lys Glu Ala
                165                 170                 175

Val Ala Thr Ala Lys Ala Glu His His Asp Tyr Val Leu Ile Asp Thr
            180                 185                 190

Ala Gly Arg Leu His Val Asp Glu Thr Leu Met Ala Glu Leu Gln Asp
        195                 200                 205

Met Lys Ala Ala Val Thr Pro Asp Glu Ile Leu Leu Val Val Asp Ser
    210                 215                 220

Met Thr Gly Gln Asp Ala Val Asn Val Ala Glu Ser Phe Asn Asn Gln
225                 230                 235                 240

Leu Asp Val Thr Gly Ala Val Leu Thr Lys Leu Asp Gly Asp Thr Arg
                245                 250                 255

Gly Gly Ala Ala Ile Ser Ile Lys Ala Val Thr Asn Thr Pro Ile Lys
            260                 265                 270

Phe Ala Gly Met Gly Glu Lys Ile Asp Gln Leu Glu Pro Phe His Pro
        275                 280                 285

Asp Arg Met Ala Ser Arg Ile Leu Gly Met Gly Asp Val Leu Ser Leu
    290                 295                 300

Ile Glu Lys Ala Gln Ala Asn Val Asp Glu Glu Lys Ala Lys Glu Leu
305                 310                 315                 320

Glu Lys Lys Leu Arg Lys Met Asp Phe Thr Phe Asp Asp Phe Leu Glu
                325                 330                 335

Gln Leu Asp Gln Val Lys Ser Met Gly Pro Leu Glu Asp Leu Leu Gly
            340                 345                 350

Met Met Pro Gly Met Asn Lys Ala Lys Gly Met Lys Asn Leu Lys Val
        355                 360                 365

Asp Glu Lys Gln Leu Thr Glu Leu Lys Arg Leu
    370                 375
```

```
<210> SEQ ID NO 8
<211> LENGTH: 1137
<212> TYPE: DNA
<213> ORGANISM: Bacillus clausii

<400> SEQUENCE: 8

atggcatttg aaggacttgc cgcgcgcctg caagatacgt tgacaaaaat tcgcggcaaa      60

ggcaaagtca gcgaacaaga catcaaagaa atgatgcgag aagtccggtt ggcattgctt     120
```

-continued

```
gaagcggacg ttaactttaa agtcgtaaag caattcattg cgaatgtgaa agaaaaggcg    180

cttggccaag aagttatgaa aagcctaacg cctggccagc aagtgatcaa agtcgtaaac    240

gaagagttga ccgcattgat gggggcggag caaagcaaaa ttgctgttgc ccaaaaaccg    300

ccaactgtgg tgatgatggt aggcttgcaa ggtgctggga aaacgacgac aacggcaaag    360

ctcgccaatc atttgcgcaa gaagcacaac cgcaagccac tgctcgttgc ctgtgacgtt    420

taccgcccag cggctatcca acagttggag acgcttggca agcaactgaa catgcctgtc    480

ttttccaaag ggacggacgc caatccagtt gatatagcta aagaagcggt tgcgactgcc    540

aaagcagaac atcatgatta tgtgttgatt gatacggctg gccgccttca tgtagatgaa    600

acgttaatgg cggaactgca agatatgaaa gcagctgtca cacctgatga aattttgcta    660

gtcgtcgatt cgatgacagg tcaagatgct gtcaatgtcg cagagagctt taacaaccag    720

cttgatgtca caggcgctgt gttgacgaaa ctagatggcg atacccgcgg aggggctgcg    780

atttccatta aggcagtaac aaatacgccg attaaatttg ccggcatggg cgaaaaaatt    840

gaccagctag aaccgttcca tccagatagg atggcttcta gaattctcgg catgggcgat    900

gttctgtcgt taatcgaaaa agcgcaagcg aatgtcgatg aagaaaaagc aaaagagctt    960

gagaaaaaac ttcgcaaaat ggactttacg ttcgatgatt ttctagagca gctcgaccaa   1020

gtcaaaagca tggggcctct tgaagatttg ctagggatga tgccggggat gaataaggca   1080

aaaggcatga aaaacctaaa agttgatgaa aagcaattga ccgagttgaa gcgattg      1137
```

<210> SEQ ID NO 9
<211> LENGTH: 841
<212> TYPE: PRT
<213> ORGANISM: Bacillus clausii

<400> SEQUENCE: 9

```
Met Leu Gly Leu Leu Arg Lys Ile Val Gly Asp Pro Ala Gln Lys Gln
1               5                   10                  15

Leu Lys Lys Asn Glu Lys Ile Val Asp Ile Lys Cys Glu Ala Leu Gln
            20                  25                  30

Cys Met Lys Gln Leu Ser Asp Glu Gln Leu Lys Asn Lys Thr Ala Glu
        35                  40                  45

Phe Lys Ala Lys Leu Glu Glu Gly Ala Ser Leu Asn Asp Ile Val Val
    50                  55                  60

Pro Ala Leu Ala Val Ala Arg Glu Ala Ala Gly Arg Val Leu Asn Glu
65                  70                  75                  80

Tyr Pro Tyr Arg Val Gln Leu Leu Gly Ala Leu Ala Leu His Gln Gly
                85                  90                  95

Asn Ile Ala Glu Met Lys Thr Gly Glu Gly Lys Thr Leu Val Gly Thr
            100                 105                 110

Ile Ala Val Tyr Val Gln Ala Leu Glu Gly Lys Gly Val His Ile Val
        115                 120                 125

Thr Val Asn Asn Tyr Leu Ala Arg Arg Asp Leu Glu Asn Tyr Gly Arg
    130                 135                 140

Ile Phe Gln Phe Leu Gly Leu Thr Val Gly Leu Asn Glu Asn Gly Leu
145                 150                 155                 160

Thr Arg Glu Glu Lys Gln Lys Ala Tyr Ala Ala Asp Val Thr Tyr Ser
                165                 170                 175

Thr Asn Asn Glu Leu Gly Phe Asp Tyr Leu Arg Asp Asn Met Val Leu
            180                 185                 190

Tyr Lys Glu Gln Met Val Gln Arg Pro Leu His Phe Ala Leu Ile Asp
```

-continued

```
        195                 200                 205

Glu Val Asp Ser Ile Leu Ile Asp Glu Ala Arg Thr Pro Leu Ile Ile
    210                 215                 220

Ser Gly Ser Val Glu Arg Lys Thr Lys Leu Tyr Gly Gln Ala Asn Thr
225                 230                 235                 240

Phe Val Arg Val Leu Lys Arg Asp Ala Asp Tyr Thr Tyr Asp Glu Lys
                245                 250                 255

Thr Lys Ser Val Gln Leu Thr Asp Glu Gly Val Asn Lys Ala Glu Arg
            260                 265                 270

Ala Phe Asn Ile Asp Asn Leu Tyr Asp Gln Lys His Val Gln Leu Asn
        275                 280                 285

His His Ile Asn Gln Ser Leu Lys Ala His Val Ala Met His Arg Asp
    290                 295                 300

Ala Asp Tyr Val Val Glu Asp Gly Glu Val Val Ile Val Asp Gln Phe
305                 310                 315                 320

Thr Gly Arg Leu Met Lys Gly Arg Arg Tyr Ser Asp Gly Leu His Gln
                325                 330                 335

Ala Leu Glu Ala Lys Glu Gly Leu Glu Val Gln Arg Glu Ser Ile Thr
            340                 345                 350

Leu Ala Ser Ile Thr Phe Gln Asn Tyr Phe Arg Met Tyr Gln Lys Leu
        355                 360                 365

Ala Gly Met Thr Gly Thr Ala Lys Thr Glu Glu Glu Glu Phe Arg Asn
    370                 375                 380

Ile Tyr Gly Met Asp Val Met Val Ile Pro Thr Asn Lys Pro Val Ala
385                 390                 395                 400

Arg Glu Asp Arg Pro Asp Leu Ile Tyr Lys Thr Met Gln Gly Lys Phe
                405                 410                 415

Asn Ala Val Val Ser Glu Ile Ala Glu Leu His Lys Thr Gly Arg Pro
            420                 425                 430

Val Leu Val Gly Thr Val Asn Val Glu Thr Ser Glu Val Val Ser Lys
        435                 440                 445

Met Leu Thr Arg Lys Arg Ile Pro His His Val Leu Asn Ala Lys Asn
    450                 455                 460

His Glu Arg Glu Ala Glu Ile Ile Glu Lys Ala Gly His Lys Gly Ala
465                 470                 475                 480

Val Thr Ile Ala Thr Asn Met Ala Gly Arg Gly Thr Asp Ile Lys Leu
                485                 490                 495

Gly Pro Gly Val Lys Glu Leu Gly Gly Leu His Val Leu Gly Thr Glu
            500                 505                 510

Arg His Glu Ser Arg Arg Ile Asp Asn Gln Leu Arg Gly Arg Ala Gly
        515                 520                 525

Arg Gln Gly Asp Val Gly Ser Ser Gln Phe Tyr Leu Ser Met Glu Asp
    530                 535                 540

Glu Leu Met Arg Arg Phe Gly Ser Asp Asn Met Lys Ala Met Met Glu
545                 550                 555                 560

Lys Leu Gly Met Glu Asp Asp Gln Pro Ile Glu Ser Ser Leu Val Ser
                565                 570                 575

Arg Ala Val Glu Thr Ala Gln Lys Arg Val Glu Gly Asn Asn Phe Asp
            580                 585                 590

Ala Arg Lys Gln Val Leu Gln Phe Asp Asp Val Met Arg Glu Gln Arg
        595                 600                 605

Glu Ile Ile Tyr Lys Gln Arg Met Glu Val Leu Glu Ala Asp Asn Leu
    610                 615                 620
```

```
Lys Thr Ile Val Glu Asn Met Met Lys Ala Thr Val Glu Arg Val Val
625                 630                 635                 640

Gln Thr His Cys Pro Glu Ser Leu Val Gln Glu Glu Trp Asp Leu Ala
                645                 650                 655

Ala Val Ala Thr Tyr Ile Asn Gly Gln Leu Leu Ser Glu Asn Gly Ile
            660                 665                 670

Ser Glu Lys Glu Leu Lys Gly Lys Glu Gln Glu Glu Leu Ile Glu Leu
        675                 680                 685

Ile Thr Glu Lys Val Leu Ala Ala Tyr His Ala Lys Glu Ala Glu Val
    690                 695                 700

Ser Ser Glu Gln Met Arg Glu Phe Glu Lys Val Ile Met Leu Arg Thr
705                 710                 715                 720

Val Asp Arg Lys Trp Met Asn His Ile Asp Gln Met Asp Gln Leu Arg
                725                 730                 735

Gln Gly Ile His Leu Arg Ala Tyr Gly Gln Asn Asp Pro Leu Arg Glu
            740                 745                 750

Tyr Arg Phe Glu Gly Phe Asn Met Phe Glu Ala Met Ile Ala Glu Ile
        755                 760                 765

Glu Glu Glu Val Ser Met Tyr Val Met Lys Ala Gln Val Gln Gln Asn
    770                 775                 780

Leu Lys Arg Glu Glu Val Ala Glu Gly Lys Ala Val Lys Pro Ser Ala
785                 790                 795                 800

Asn Gly Gln Glu Asp Lys Lys Ala Lys Arg Lys Pro Val Arg Lys Ala
                805                 810                 815

Glu Asn Ile Gly Arg Asn Asp Pro Cys Ile Cys Gly Ser Gly Lys Lys
            820                 825                 830

Tyr Lys Asn Cys Cys Gly Ala Asn Arg
        835                 840
```

<210> SEQ ID NO 10
<211> LENGTH: 2526
<212> TYPE: DNA
<213> ORGANISM: Bacillus clausii

<400> SEQUENCE: 10

```
atgcttggat tacttcgaaa aatagtcggc gatccagccc aaaaacaatt aaagaaaaac     60

gaaaaaatcg tcgacatcaa gtgcgaggcg ctgcagtgca tgaagcagct ttctgacgaa    120

caattaaaga acaaaacagc tgaattcaag gcaaagctag aagaaggcgc ttctcttaac    180

gatatagtag ttcctgcgct tgcagttgct cgtgaagctg cgggcagggt gttaaatgag    240

tatccatacc gcgtccagtt gctcggtgca ctggcgctgc accaaggcaa tattgccgaa    300

atgaaaacag gggaagggaa aacgctcgtc ggcacaattg ccgtctatgt ccaagccctg    360

gagggaaaag gcgttcatat tgtaacggtc aataactact tagcccgccg cgacttagaa    420

aactatgggc ggatttttca attcttaggg ttgacagtag gattgaatga aaacggcctt    480

acgagagaag aaaaacaaaa agcatatgcc gctgatgtga cgtacagcac aaataatgag    540

cttgggtttg attatttgcg tgataacatg gtgctttaca aagaacaaat ggtgcaacgg    600

ccgctccatt ttgcgttaat cgatgaagtt gactcgattt taattgatga agcacggacg    660

ccgctaatta tttctggttc tgttgaacgg aaaacaaaac tttatggaca agccaataca    720

tttgtgcgcg ttttaaagcg cgatgctgat tacacatacg atgaaaaaac aaaatctgtc    780

cagttgacgg atgaaggtgt caataaagca gagcgcgcgt ttaacatcga caacctttac    840
```

-continued

```
gatcaaaagc atgtccaact gaaccatcat attaaccaat cgttaaaagc ccatgtggcc    900

atgcaccgtg atgctgacta tgtcgtagaa gacggcgaag tcgtaatcgt tgaccagttt    960

acgggtcgtt taatgaaagg aaggcgttat agcgacggac ttcaccaagc gctagaagca   1020

aaagaaggtt tagaggtgca gcgcgaaagc atcacgctag catcgattac attccaaaac   1080

tatttccgta tgtaccaaaa gctcgcagga atgacgggga cggctaagac ggaggaagaa   1140

gagttccgca atatttacgg catggacgta atggtcattc cgaccaataa accggttgct   1200

cgggaagacc gccctgattt aatttataag acgatgcaag ggaaattcaa cgcagtcgtc   1260

agtgaaattg ccgagcttca caaaacgggg cgccctgtgc tagtaggtac agtcaacgtt   1320

gaaacatctg aagttgtttc caaaatgttg acaagaaaac ggattccaca ccacgtctta   1380

aatgcaaaaa accatgagcg agaagcagaa attattgaaa aagctggcca taaaggggcc   1440

gtcacgatcg caacgaacat ggctggacgt ggaacggaca ttaaacttgg cccaggggtt   1500

aaagagcttg gcggcctcca cgttcttggt acagagcgcc atgagagccg gcggattgac   1560

aaccaattgc gtggtcgtgc tgggcgtcaa ggggatgtag gttcttctca gttttatttg   1620

tcgatggaag atgagctgat gaggcggttt ggctcagaca atatgaaagc gatgatggaa   1680

aagctaggca tggaagacga ccagcctatt gaatcatcat tggtttcaag ggcggtggaa   1740

acagctcaga agcgggttga aggcaataac tttgatgctc gtaaacaagt gctccagttt   1800

gacgacgtta tgcgtgagca acgggagatt atttacaaac aacggatgga agtgcttgaa   1860

gccgataact taaaaacaat tgtcgaaaat atgatgaagg cgactgtaga acgtgtagtt   1920

caaacccatt gccctgaatc gctcgttcag gaagaatggg atttggctgc tgttgccacc   1980

tatatcaacg ggcaattgct gtctgaaaac ggaattagtg agaaagagct gaaagggaaa   2040

gagcaagagg aactgatcga gttgattacc gaaaaagtcc tcgctgcata ccatgcgaaa   2100

gaagcagaag tctcttcaga acaaatgcgc gagtttgaaa aagtgatcat gctgcgcact   2160

gttgaccgca agtggatgaa ccacattgac caaatggatc aattacgaca aggcatacat   2220

ttgcgcgctt acggccaaaa tgatccgttg cgtgagtatc gctttgaagg ctttaatatg   2280

tttgaagcga tgatcgctga aattgaagaa gaagtatcta tgtacgtgat gaaagctcaa   2340

gtgcaacaaa accttaagcg tgaggaagta gctgaaggaa aagcggtgaa accgtcagcc   2400

aatgggcaag aggacaaaaa agcgaaacgg aaaccagtcc gcaaagctga aaacattggy   2460

agaaatgatc catgcatttg tggcagcggc aaaaaataca aaaattgttg tggggctaac   2520

cgataa                                                              2526
```

```
<210> SEQ ID NO 11
<211> LENGTH: 433
<212> TYPE: PRT
<213> ORGANISM: Bacillus clausii

<400> SEQUENCE: 11

Met Val Lys Lys Gly Lys Ile Ala Leu Phe Phe Leu Ile Ile Ala Leu
1               5                   10                  15

Phe Ala Ser Gly Ile Ala Tyr Phe Ala Lys Pro Val Val Asn Asp Val
            20                  25                  30

Ser Leu Gly Leu Asp Leu Gln Gly Gly Phe Glu Val Leu Tyr Glu Val
        35                  40                  45

Glu Pro Met Asn Glu Gly Asp Glu Ile Asn Gln Asp Ser Leu Leu Ala
    50                  55                  60

Thr Thr Thr Ala Leu Asn Glu Arg Val Asn Thr Ile Gly Val Ser Glu
```

-continued

```
65                  70                  75                  80

Pro Asn Ile Gln Ile Glu Gly Glu Asn Arg Ile Arg Val Gln Leu Ala
                85                  90                  95

Gly Val Glu Asp Gln Glu Thr Ala Arg Asp Ile Leu Ala Thr Gly Ala
            100                 105                 110

Glu Leu Thr Ile Arg Asp Val Asp Asp Asn Val Leu Leu Asp Gly Ser
        115                 120                 125

Asp Leu Thr Gln Asn Gly Ala Ser Ala Ser Val His Pro Glu Lys Asn
    130                 135                 140

Gln Pro Ile Val Thr Leu Thr Leu Asn Asp Ala Asp Lys Phe Gly Glu
145                 150                 155                 160

Ile Thr Arg Glu Ile Ser Glu Arg Pro Leu Gly Glu Asn Leu Leu Val
                165                 170                 175

Ile Trp Leu Asp Phe Glu Glu Gly Asp Ser Phe Ala Glu Glu Ser Lys
            180                 185                 190

Lys Gln Asp Pro Lys Tyr Met Ser Ala Ala Ser Val Asn Ala Pro Leu
        195                 200                 205

His Thr Arg Asp Val Met Ile Glu Gly Asn Phe Thr Thr Glu Glu Thr
    210                 215                 220

Arg Phe Leu Ala Glu Ile Leu Asn Ala Gly Ala Leu Pro Val Glu Leu
225                 230                 235                 240

Asn Glu Ile Tyr Ser Thr Ser Val Gly Ala Ser Leu Gly Glu Lys Ala
                245                 250                 255

Met Asn Gln Thr Ile Phe Ala Gly Ser Leu Gly Val Gly Leu Ile Phe
            260                 265                 270

Leu Tyr Met Val Val Tyr Tyr Arg Phe Pro Gly Ile Ile Ala Val Ile
        275                 280                 285

Thr Leu Ser Ile Tyr Thr Phe Leu Val Leu Val Val Phe Asn Ala Met
    290                 295                 300

Asn Ala Val Leu Thr Leu Pro Gly Ile Ala Ala Leu Val Leu Gly Val
305                 310                 315                 320

Gly Met Ala Val Asp Ala Asn Ile Ile Thr Tyr Glu Arg Ile Lys Glu
                325                 330                 335

Glu Ile Lys Ser Gly Lys Ser Ile Leu Ser Ala Phe Lys Val Gly Ser
            340                 345                 350

Arg Arg Ser Phe Ala Thr Ile Phe Asp Ala Asn Ile Thr Thr Leu Ile
        355                 360                 365

Ala Ala Gly Val Met Phe Tyr Phe Gly Thr Ser Ser Val Gln Gly Phe
    370                 375                 380

Ala Val Met Leu Ile Ile Ser Ile Leu Val Ser Phe Leu Thr Ala Val
385                 390                 395                 400

Tyr Gly Ser Arg Val Leu Leu Gly Leu Trp Val Asn Ser Lys Phe Leu
                405                 410                 415

Asn Lys Arg Pro Gly Trp Phe Gly Val Lys Arg Gly Glu Ile Asp Glu
            420                 425                 430

Leu
```

<210> SEQ ID NO 12
<211> LENGTH: 1299
<212> TYPE: DNA
<213> ORGANISM: Bacillus clausii

<400> SEQUENCE: 12

```
atggttaaaa aaggcaaaat tgcgcttttc tttctcatta ttgcgttgtt tgcttctgga     60
```

-continued

```
attgcctatt ttgcaaagcc tgttgtaaac gacgtcagcc ttgggcttga cctgcaaggc    120

ggctttgaag tgctctacga agtggagcca atgaatgagg gcgatgaaat taatcaggat    180

tcgcttttag caacaacgac tgcattgaat gaaagggtaa atacaattgg cgtttcagaa    240

ccgaacatcc aaattgaagg agaaaatcgc atccgtgtcc agttagctgg cgttgaagac    300

caagaaacag cacgtgacat tttagcgact ggcgcagaat tgacgatccg tgacgtcgat    360

gacaacgtgc ttcttgatgg cagcgattta acccaaaatg gcgccagcgc atcggtacat    420

ccagaaaaaa atcagccgat tgtcacattg acgctaaatg atgcagacaa atttggcgaa    480

atcacacgtg aaatttccga acgcccacta ggagagaatt tgctcgtcat ctggcttgac    540

tttgaggaag gcgacagctt tgcagaagaa tcaaaaaaac aagaccctaa atacatgtca    600

gcagcgtccg ttaatgcccc gttacataca cgagacgtga tgatcgaagg gaactttaca    660

actgaggaaa cacgctttct tgctgaaata ttaaatgcag gcgctttgcc tgttgagtta    720

aatgagatct actctacatc agtcggtgca tcgctagggg aaaaagcgat gaaccaaacg    780

atttttgctg gctcccttgg ggttgggctg atctttttgt atatggttgt ttactatcgc    840

tttccaggaa tcatcgctgt cataacacta agcatttata catttttggt gcttgtcgtc    900

tttaatgcca tgaatgctgt gttaactttg ccaggcattg ccgcgctcgt gcttggtgtg    960

ggcatggctg tcgatgcgaa tatcattact tatgaacgga ttaaggaaga gattaaatca   1020

gggaaatcga ttttatctgc ctttaaagtc ggcagcagac gctcgtttgc aacgattttt   1080

gatgccaata tcacgacgtt gattgcggct ggcgtcatgt tttattttgg gacgagctct   1140

gtgcaaggct ttgcagtcat gctcattatt agcattcttg tcagcttttt aacggctgtc   1200

tatggttcca gggtgttgct aggcctctgg gtaaacagca aatttttaaa taaacggcct   1260

ggctggtttg gcgtgaaaag aggtgaaatt gatgagctt                          1299
```

<210> SEQ ID NO 13
<211> LENGTH: 27
<212> TYPE: PRT
<213> ORGANISM: Bacillus clausii

<400> SEQUENCE: 13

```
Met Ala Asp Glu Asn Lys Gly Pro Val Thr Phe Leu Arg Asn Val Gly
 1               5                  10                  15

Arg Glu Met Lys Arg Val Thr Trp Pro Thr Lys
            20                  25
```

<210> SEQ ID NO 14
<211> LENGTH: 81
<212> TYPE: DNA
<213> ORGANISM: Bacillus clausii

<400> SEQUENCE: 14

```
atggcagatg aaaacaaagg accagttact tttcttcgga atgtaggcag ggaaatgaaa     60

cgcgtaacat ggccaactaa a                                               81
```

<210> SEQ ID NO 15
<211> LENGTH: 311
<212> TYPE: PRT
<213> ORGANISM: Bacillus clausii
<220> FEATURE:
<221> NAME/KEY: VARIANT
<222> LOCATION: (1)...(311)
<223> OTHER INFORMATION: Xaa = Any Amino Acid

<400> SEQUENCE: 15

```
Met Ser Phe Asn Pro Glu Lys Trp Asn Val Asp Leu Thr Lys His Arg
 1               5                  10                  15

Lys Arg Phe Phe Ile Gly Ser Gly Leu Ser Met Val Leu Gly Ile Val
            20                  25                  30

Leu Leu Leu Thr Phe Gly Leu Asn Leu Gly Val Asp Phe Glu Ser Gly
        35                  40                  45

Ser Asn Val Glu Ile Gln Ala Asp Gln Thr Leu Thr Gln Glu Gln Leu
    50                  55                  60

Leu Asp Asp Phe Ala Ala Ile Asn Glu Ser Tyr Thr Pro Asn Ile Thr
65                  70                  75                  80

Leu Gly Gly Glu Gln Ser Gln Ser Ala Thr Ala Arg Phe Thr Val Glu
                85                  90                  95

Leu Ser Lys Asp Glu Ile Thr Thr Ile Gln Thr Tyr Phe Gln Asp Lys
            100                 105                 110

Tyr Gly His Ser Pro Asn Val Ser Thr Val Ser Pro Leu Val Gly Gln
        115                 120                 125

Glu Leu Ala Arg Asn Ala Ile Leu Ser Val Leu Ile Ala Ser Ile Gly
    130                 135                 140

Ile Val Ile Tyr Ile Gly Leu Arg Phe Xaa Tyr Leu Tyr Gly Val Ser
145                 150                 155                 160

Ala Val Ile Gly Leu Leu His Asp Ala Phe Ile Ile Ile Ala Leu Phe
                165                 170                 175

Ser Leu Phe Gln Val Glu Ile Asn Val Pro Phe Ile Ala Ala Val Leu
            180                 185                 190

Thr Val Val Gly Tyr Ser Ile Asn Asp Thr Ile Val Thr Phe Asp Arg
        195                 200                 205

Met Arg Glu Asn Ile Asn Lys Glu Lys Glu Ile Asn Ser Phe Glu His
    210                 215                 220

Leu Ala Gln Ile Val Asn Lys Ser Leu Leu Gln Val Leu Thr Arg Ser
225                 230                 235                 240

Ile Asn Thr Val Leu Thr Val Leu Phe Ala Ala Val Ala Leu Leu Ile
                245                 250                 255

Phe Gly Gly Glu Ala Ile Arg Ser Phe Ser Leu Ala Leu Val Ile Gly
            260                 265                 270

Leu Ile Ala Gly Thr Tyr Ser Ser Met Phe Leu Cys Ala Gln Met Trp
        275                 280                 285

Leu Val Trp Glu Trp Lys Arg Gln Lys Lys Leu Lys Asn Lys Pro Lys
    290                 295                 300

Lys Thr Glu Glu Glu Tyr Ile
305                 310
```

<210> SEQ ID NO 16
<211> LENGTH: 933
<212> TYPE: DNA
<213> ORGANISM: Bacillus clausii

<400> SEQUENCE: 16

```
atgagcttta atccggaaaa gtggaatgtc gatttgacaa aacaccgaaa acgttttttt      60

atcggctcgg gcttgtcaat ggtccttgga attgtgttgt tgctgacatt tggtttaaat     120

ttaggcgttg attttgaaag tggttcaaat gtggaaatcc aagcggatca gacattgacg     180

caagaacaat tactggacga ctttgcagca atcaatgaat cgtacacgcc gaatattaca     240

cttggaggcg agcaaagcca aagtgcgact gcccggttta cagtcgaact ttccaaagat     300
```

-continued

```
gaaattacca cgatccagac gtatttccaa gacaaatacg ggcattcgcc taacgtcagt    360

acagtgtcgc cccttgtcgg ccaggaactc gctcgcaatg cgattttgtc tgtattgatc    420

gcttcgatcg gaatcgttat ttacatcggt ctccgctttc mctaccttta tggcgtttca    480

gcggttatcg gcttgctcca cgatgccttt atcattattg cgttgtttag cttgttccaa    540

gttgaaatta atgttccttt tatagcagca gtgctcactg ttgtcggcta ctcaatcaat    600

gacaccattg ttacgtttga ccgcatgcgg gaaaatatta acaaggagaa ggaaattaac    660

agctttgagc acttggcgca aattgtcaac aaaagcttgc tgcaagtgtt aacacgctcg    720

atcaatacgg tattgaccgt actatttgcc gctgtggcat tgctgatatt cggcggcgaa    780

gcgatccgct cgttttcatt ggctttagtc attggtttga ttgccggtac ttattcttcg    840

atgttccttt gtgcgcaaat gtggcttgtc tgggaatgga aacggcaaaa gaaactaaaa    900

aacaaaccaa agaaaacgga agaagagtac att                                 933
```

```
<210> SEQ ID NO 17
<211> LENGTH: 54
<212> TYPE: PRT
<213> ORGANISM: Bacillus clausii

<400> SEQUENCE: 17

Gln Pro Gly Arg Ser Ser Gly Leu Ser Gly Ala Ile Thr Gly Gly Ala
1               5                   10                  15

Glu Gln Leu Leu Gly Lys Gln Lys Ala Arg Gly Leu Asp Ala Val Leu
            20                  25                  30

His Arg Ala Thr Ile Val Leu Ala Val Leu Phe Phe Ile Leu Thr Gly
        35                  40                  45

Leu Asn Ala Tyr Phe Leu
    50
```

```
<210> SEQ ID NO 18
<211> LENGTH: 165
<212> TYPE: DNA
<213> ORGANISM: Bacillus clausii

<400> SEQUENCE: 18

ttgcagccag gtcgcagctc tgggttatcg ggcgccatta ctggaggggc agagcagttg     60

ctaggaaaac aaaaagcgcg cgggcttgat gcggtattgc atcgagcaac aatcgtactt    120

gctgttttgt tttttatttt gacagggtta aatgcgtatt tccta                    165
```

```
<210> SEQ ID NO 19
<211> LENGTH: 436
<212> TYPE: PRT
<213> ORGANISM: Bacillus clausii

<400> SEQUENCE: 19

Met Phe Lys Ala Ile Ser Asn Ile Phe Arg Val Arg Asp Leu Arg Arg
1               5                   10                  15

Lys Ile Val Phe Thr Leu Leu Met Leu Ile Val Phe Arg Ile Gly Ala
            20                  25                  30

Phe Ile Pro Val Pro Gly Thr Asn Ser Asp Ala Leu Glu Met Leu Phe
        35                  40                  45

Gly Gly Ala Asn Ala Phe Gly Phe Leu Asp Thr Phe Gly Gly Gly Ala
    50                  55                  60

Leu Ser Asn Phe Ser Ile Phe Ala Met Gly Ile Met Pro Tyr Ile Thr
65                  70                  75                  80
```

-continued

```
Ala Ser Ile Val Val Gln Leu Leu Gln Leu Asp Val Val Pro Lys Phe
                85                  90                  95

Ala Glu Trp Ala Lys Gln Gly Glu Ala Gly Arg Lys Lys Leu Thr Gln
            100                 105                 110

Val Thr Arg Tyr Gly Thr Ile Val Leu Gly Phe Val Gln Ala Ile Ala
        115                 120                 125

Met Ser Val Gly Phe Asn Ser Met Tyr Gln Gly Ala Gly Pro Gly Leu
    130                 135                 140

Ile Glu Asn Pro Ser Val Met Thr Tyr Val Tyr Ile Ala Ile Val Leu
145                 150                 155                 160

Thr Ala Gly Thr Ala Phe Leu Met Trp Leu Gly Glu Gln Ile Thr Ala
                165                 170                 175

His Gly Val Gly Asn Gly Ile Ser Leu Ile Ile Phe Ala Gly Ile Ala
            180                 185                 190

Ala Gly Val Pro Asn Met Leu Asn Ala Leu Tyr Thr Ser Glu Ile Glu
        195                 200                 205

Gly Ala Gly Asp Gln Leu Phe Leu Ser Ile Ala Thr Val Ala Leu Leu
    210                 215                 220

Ala Leu Ile Val Leu Leu Ile Ile Ile Gly Val Ile Tyr Val His Gln
225                 230                 235                 240

Ala Leu Arg Lys Ile Pro Val Gln Tyr Ala Lys Arg Val Val Asn Arg
                245                 250                 255

Ser Gln Val Gly Gly Gln Ser Thr His Leu Pro Ile Lys Val Asn Ala
            260                 265                 270

Ala Gly Val Ile Pro Val Ile Phe Ala Ser Ala Leu Phe Tyr Phe Pro
        275                 280                 285

Ser Thr Ile Ala Ser Phe Val Gly Pro Asp Asp Lys Ala Trp Ala Arg
    290                 295                 300

Trp Ile Val Glu His Phe Val Pro Ser Ser Trp Ile Gly Gly Ser Ile
305                 310                 315                 320

Phe Val Val Leu Ile Ile Ala Phe Thr Tyr Phe Tyr Thr Phe Val Gln
                325                 330                 335

Val Asn Pro Glu Lys Met Ala Asp Asn Leu Lys Arg Gln Gly Gly Tyr
            340                 345                 350

Ile Pro Gly Ile Arg Pro Gly Gln Ala Thr Gln Ser Phe Ile Thr Lys
        355                 360                 365

Ile Leu Tyr Arg Leu Thr Phe Val Gly Ala Leu Phe Leu Ala Thr Ile
    370                 375                 380

Ala Thr Ile Pro Val Val Phe Ile Ala Leu Leu Asp Leu Pro Gln Gln
385                 390                 395                 400

Val Gln Ile Gly Gly Thr Gly Leu Leu Ile Ile Val Gly Val Ala Leu
                405                 410                 415

Asp Thr Met Lys Gln Ile Glu Gly Gln Leu Ile Lys Arg Ser Tyr Lys
            420                 425                 430

Gly Phe Ile Asn
        435
```

<210> SEQ ID NO 20
<211> LENGTH: 1308
<212> TYPE: DNA
<213> ORGANISM: Bacillus clausii

<400> SEQUENCE: 20

```
atgtttaagg cgatctccaa catcttccgt gtgagagatt tacgtcgaaa aatcgtcttt     60
```

-continued

```
acgcttctga tgcttattgt ttttcgaatc ggcgcattca tacccgtgcc aggcacgaac    120

agtgatgcgc ttgagatgct ttttggcgga gctaatgctt ttgggtttct cgataccttt    180

ggcggcggcg cactaagcaa cttctcgatt tttgcaatgg ggatcatgcc ttacatcaca    240

gcctcgatcg ttgttcagct tcttcaactg gatgtagtgc cgaagtttgc agaatgggcg    300

aaacagggcg aggctggtcg gaaaaagcta acgcaagtaa ctcgatatgg tacgattgtt    360

ttagggtttg tccaagcgat cgccatgtca gtcggtttta attcaatgta tcaaggagca    420

ggccctggct tgattgaaaa tccatctgtg atgacgtacg tctatatcgc catcgtcctt    480

acagcaggta cagcattttt aatgtggcta ggggagcaga ttacagctca cggtgtaggg    540

aatggaatct cgctcattat ctttgcaggt attgcagccg gcgttccaaa catgctgaat    600

gctttatata catctgaaat tgaaggcgca ggcgaccagt tgtttttgag catcgccacc    660

gttgcattgc tcgctttaat cgttttactg attatcattg gcgtcattta cgtgcaccaa    720

gccttgcgga aaatacctgt ccaatatgcg aagcgcgtcg tcaatcgcag ccaagtaggc    780

ggacagtcaa cgcatttgcc gattaaagtg aacgctgcag ggtcattcc  ggtcatcttt    840

gcctcagcat tgttttattt tccgtcaacc attgcttcat ttgttgggcc agatgacaag    900

gcatgggcaa gatggattgt ggaacatttc gtgccgagtt catggatcgg cggcagcatt    960

tttgttgtct tgattatcgc gtttacgtat ttttacacat ttgtacaggt taacccggaa   1020

aaaatggccg ataatttgaa acggcaaggc gggtatatcc ctggcattcg tcctggtcaa   1080

gcaacgcagt cttttatcac gaaaatttta tatcggctta cgttcgttgg cgctctattc   1140

cttgcgacca tcgcaacgat accggttgtg tttattgcgc tacttgactt gccgcagcaa   1200

gtgcaaattg gcggcacggg cttgttaatc atcgtcggcg ttgcgctaga tacgatgaaa   1260

caaatcgaag ggcagctcat taaacgttcg tataaaggct tcattaac                1308
```

<210> SEQ ID NO 21
<211> LENGTH: 184
<212> TYPE: PRT
<213> ORGANISM: Bacillus clausii

<400> SEQUENCE: 21

```
Met Ala Phe Arg Gly Phe Pro Ile Glu Trp Ala Lys Ala Ile Cys Ile
 1               5                  10                  15

Ala Leu Cys Ala Thr Met Leu Val Arg Leu Phe Leu Tyr Ala Pro Ile
            20                  25                  30

Val Val Asp Gly His Ser Met Gln Pro Thr Leu Asp Ser Gly Asp Lys
        35                  40                  45

Met Ile Val Asn Gln Ile Gly Tyr Val Phe Ile Glu Pro Gln Arg Phe
    50                  55                  60

Asp Ile Val Val Phe His Ala Pro Gly Gly Lys Asp Tyr Ile Lys Arg
65                  70                  75                  80

Ile Ile Gly Leu Pro Gly Asp His Leu Lys Tyr Glu Asn Asp Thr Leu
                85                  90                  95

Tyr Ile Asn Gly Glu Glu Thr Ala Glu Pro Tyr Leu Asn Ser Leu Lys
            100                 105                 110

Gln Thr Leu Tyr Gly Asp Gln Leu Leu Thr Gly Asp Phe Thr Leu Glu
        115                 120                 125

Glu Leu Ile Gly Glu Glu Val Ile Pro Asp Asp His Tyr Phe Met Met
    130                 135                 140

Gly Asp Asn Arg Arg Leu Ser Lys Asp Ser Arg Asp Ile Gly Leu Ile
```

-continued

```
145                 150                 155                 160

Pro Lys Ser Glu Ile Ile Gly Lys Ala Asn Val Ile Phe Tyr Pro Phe
                165                 170                 175

Glu His Ile Ser Ile Val Asn Asp
            180


<210> SEQ ID NO 22
<211> LENGTH: 552
<212> TYPE: DNA
<213> ORGANISM: Bacillus clausii

<400> SEQUENCE: 22

gtggcatttc gcggatttcc aattgagtgg gccaaagcca tttgcatcgc gttatgcgcc     60

acaatgctcg tacgcctttt tttgtacgcg cccattgttg tagacggcca ttcgatgcag    120

ccaacgctcg actctgggga caaaatgatc gtcaaccaaa ttgggtatgt ttttattgag    180

ccacaacgtt ttgatattgt tgttttccac gcacctggcg ggaaagatta tattaaacgg    240

atcattggcc tccctggcga ccatttgaaa tatgaaaacg atacgcttta tattaacggg    300

gaagaaacag cggaacctta tttaaactcg ctgaaacaga cgctttacgg cgaccaattg    360

cttactggcg attttacact ggaagagtta atcggcgaag aggtaatacc tgacgatcat    420

tattttatga tgggcgataa tcgccgttta agtaaagaca gccgtgatat tggtctcatt    480

ccgaaatcag aaattatcgg caaagccaac gtcatttttt atccgtttga acatataagc    540

attgttaacg at                                                        552


<210> SEQ ID NO 23
<211> LENGTH: 179
<212> TYPE: PRT
<213> ORGANISM: Bacillus clausii

<400> SEQUENCE: 23

Met Ala Asp Ala Lys Arg Asn Ser Glu Phe Trp Gly Trp Val Lys Thr
 1               5                  10                  15

Ile Ala Ile Ala Phe Ile Leu Ala Val Gly Ile Arg Thr Phe Val Ile
            20                  25                  30

Glu Arg Phe Glu Val Gln Gly Ala Ser Met Val Pro Thr Ala His Asp
        35                  40                  45

Gly Glu His Phe Ile Ile Asp Lys Trp Ser Tyr Gln Phe Gly Glu Pro
    50                  55                  60

Glu Arg Phe Asp Leu Ile Val Phe Gln Ala Thr Glu Glu Asp Arg Tyr
65                  70                  75                  80

Ile Lys Arg Val Ile Gly Leu Pro Gly Asp Thr Ile Arg Phe Glu Asn
                85                  90                  95

Asp Ile Leu Tyr Ile Asn Gly Glu Gln Ile Glu Glu Pro Tyr Leu Gln
            100                 105                 110

Glu Ala Lys Ala Ala Tyr Ser Gly Pro Val Tyr Thr Glu Asp Tyr Ser
        115                 120                 125

Phe Glu Glu Ala Val Pro Glu Asn His Val Phe Val Met Gly Asp Asn
    130                 135                 140

Arg Pro Thr Ser Leu Asp Ser Arg Thr Ile Gly Pro Val Ser Glu Asp
145                 150                 155                 160

Lys Ile Ile Gly Lys Val Gly Leu Arg Phe Trp Pro Leu Pro Glu Phe
                165                 170                 175

Asp Val Gln
```

<210> SEQ ID NO 24
<211> LENGTH: 537
<212> TYPE: DNA
<213> ORGANISM: Bacillus clausii

<400> SEQUENCE: 24

```
gtggcggacg caaaaagaaa ttcagagttt tggggttggg taaagacgat tgccattgcc      60
tttattcttg cggttggaat ccggacattt gtgattgaac gttttgaggt tcaaggcgcc     120
tcaatggtgc cgactgctca tgacggtgaa cattttatta tcgataaatg gagttatcaa     180
ttcggcgagc cggaacggtt tgatctcatt gtgttccaag caacggaaga agaccgctac     240
atcaaacggg tgattggctt accaggcgat acgattcggt ttgagaacga cattctttac     300
attaatggcg aacaaatcga agaaccttat ttgcaagaag caaaagctgc ttattcaggg     360
cctgtgtata cggaagatta ctcatttgaa gaggctgtcc cagaaaacca tgtgtttgta     420
atgggtgata accgccctac tagcttagac agccgcacta ttggcccagt tagcgaagat     480
aaaattatcg gcaaagtcgg attgcggttc tggccgctgc ctgaatttga cgtacaa       537
```

<210> SEQ ID NO 25
<211> LENGTH: 192
<212> TYPE: PRT
<213> ORGANISM: Bacillus clausii

<400> SEQUENCE: 25

```
Met Leu Met Asn Gly Arg Arg Lys Arg Gly Thr Ala Val Ala Glu Ala
 1               5                  10                  15

Glu Lys Lys Ser Glu Phe Trp Gly Gly Val Lys Ala Ile Ala Ile Ala
            20                  25                  30

Leu Ile Leu Ala Phe Val Val Arg Thr Phe Val Met Thr Ser Phe Glu
        35                  40                  45

Val Arg Gly Val Ser Met Val Pro Thr Ala His Asp Gly Glu Arg Phe
    50                  55                  60

Ile Val Asn Lys Leu Ser Tyr Gln Phe Gly Glu Pro Glu Arg Phe Asp
65                  70                  75                  80

Leu Ile Val Phe His Ala Thr Glu Glu Asp Ser Tyr Ile Lys Arg Val
                85                  90                  95

Ile Gly Leu Pro Gly Asp Thr Ile Arg Phe Glu Asp Asp Ile Leu Tyr
            100                 105                 110

Ile Asn Gly Glu Gln Val Glu Glu Pro Tyr Leu Glu Glu Ala Lys Ala
        115                 120                 125

Ala Tyr Ser Gly Pro Ala Tyr Thr Glu Asp Tyr Ser Phe Glu Glu Thr
    130                 135                 140

Val Pro Glu Asn His Val Phe Val Met Gly Asp Asn Arg Pro Ala Ser
145                 150                 155                 160

Leu Asp Ser Arg Val Ile Gly Pro Val Asn Glu Asp Glu Ile Ile Gly
                165                 170                 175

Lys Val Gly Leu Arg Phe Trp Pro Val Ser Glu Phe Gly Phe Met Asp
            180                 185                 190
```

<210> SEQ ID NO 26
<211> LENGTH: 576
<212> TYPE: DNA
<213> ORGANISM: Bacillus clausii

<400> SEQUENCE: 26

```
atgctcatga atggaagacg aaagcgagga acagcagtgg cagaagcgga aaagaaatca      60
```

```
gagttttggg gcggggtaaa ggcgattgca attgcgctaa ttcttgcgtt tgtagtccgg    120

acatttgtga tgaccagctt tgaagttcgc ggcgtctcaa tggtgccgac tgctcatgat    180

ggtgagcgtt ttattgtaaa taaattaagt taccaatttg gcgagcctga gcggtttgat    240

ctcattgtgt tccacgcgac ggaggaagat agctatatca aacgggtgat tggcttacca    300

ggcgatacca ttcgatttga ggacgacatc ctttacatta atggcgagca agtcgaagag    360

ccttatttag aagaagcaaa agctgcttat tcagggcccg cgtatacgga agattactca    420

tttgaagaaa ccgtcccaga gaaccatgtc tttgtaatgg gtgacaaccg ccctgctagc    480

ttagacagcc gtgtcattgg cccggttaat gaagatgaaa tcatcggcaa agtcggattg    540

cggttctggc cggtgtctga atttggcttt atggat                              576
```

<210> SEQ ID NO 27
<211> LENGTH: 176
<212> TYPE: PRT
<213> ORGANISM: Bacillus clausii

<400> SEQUENCE: 27

```
Met Val Asn Met Trp Ile Thr Ile Gly Lys Leu Ala Ile Thr Gly Ile
 1               5                  10                  15

Ala Ser Phe Leu Phe Phe Leu Val Leu Phe Phe Val Leu Gln Gly Lys
            20                  25                  30

Gly Ser Asp Gly Arg Gly Pro Glu Leu Phe Gly Trp Thr Ser Tyr Thr
        35                  40                  45

Ile Leu Ser Asn Ser Met Glu Pro Thr Phe Ser Ala Gly Asp Val Val
    50                  55                  60

Ile Met Lys Lys Asn Glu Glu Pro Ser Ile Gly Asp Val Val Thr Phe
65                  70                  75                  80

Met Ala Pro Glu Arg Arg Leu Phe Thr His Arg Ile Ile Glu Lys Phe
                85                  90                  95

Glu Ser Asn Gly Lys Thr Tyr Tyr Lys Thr Gln Gly Asp Asn Asn Asn
            100                 105                 110

Val Val Asp Glu Asp Pro Ile Val Lys Glu Gln Ile Val Gly Thr His
        115                 120                 125

Met Phe Thr Ile Pro Lys Val Gly Leu Val Ala Glu Lys Ile Asn Gln
    130                 135                 140

Pro Ile Gly Tyr Gly Leu Leu Ile Val Val Pro Ile Ala Gly Tyr Leu
145                 150                 155                 160

Leu Leu Ser Phe Tyr Glu Thr Ile Gln Lys Lys Arg Lys Glu Ala Ser
                165                 170                 175
```

<210> SEQ ID NO 28
<211> LENGTH: 528
<212> TYPE: DNA
<213> ORGANISM: Bacillus clausii

<400> SEQUENCE: 28

```
atggtcaaca tgtggataac aatcggaaaa ttggcgatta ccgggattgc atcgtttttg     60

ttcttcctcg ttctcttttt tgtccttcaa ggaaagggca gtgacggcag aggacctgag    120

ctgtttggct ggacaagcta taccatcttg tccaacagca tggagccgac attttccgcc    180

ggagatgtgg tcatcatgaa aaagaatgag gagcctagca ttggcgatgt tgtaacgttt    240

atggctcctg aacggcgctt gttcacacac cggattattg agaagtttga aagcaatgga    300

aagacgtatt ataagacgca aggcgataac aacaacgttg tagacgaaga cccaatcgta    360
```

-continued

```
aaagaacaaa ttgtcggcac ccatatgttc accattccta aagtgggttt agttgctgaa    420

aaaatcaatc aaccaattgg ttatggtttg ttgattgtcg tgccgattgc tgggtatttg    480

ctgttatcgt tctacgaaac catccaaaaa aaacgtaagg aggcttct                 528


<210> SEQ ID NO 29
<211> LENGTH: 383
<212> TYPE: PRT
<213> ORGANISM: Bacillus clausii

<400> SEQUENCE: 29

Met Lys Lys Arg Gly Val Phe Met Thr Asp Val Thr Met Leu Asp His
 1               5                  10                  15

Ile Ile Thr Gln Thr Leu Asp Ser Val Gly Thr Ser Arg Glu Lys Ile
            20                  25                  30

Phe Glu Ile Gly Glu Arg Ser Arg Asn Glu Tyr Glu Tyr Leu Lys Lys
        35                  40                  45

Glu Leu Asp Gln Val Lys Val Lys Leu Thr His Val Ile Asn Asp Val
    50                  55                  60

Asp Glu Thr Val Leu Lys Thr Lys His Ala Arg Asn Arg Leu Ala Lys
65                  70                  75                  80

Val Ser Lys Glu Phe Asn Arg Tyr Thr Ser Glu Glu Val Arg Thr Ala
                85                  90                  95

Tyr Glu Gln Ala Ser Asp Phe Gln Val Gln Leu Ala Val Leu Gln Gln
            100                 105                 110

Glu Glu Ile Gln Leu Arg Ile Arg Arg Asp Asp Ile Asp Arg Arg Leu
        115                 120                 125

Lys Asn Leu Gln Asp Thr Ile Asn Arg Ala Glu Gln Leu Ser Val Gln
    130                 135                 140

Met Ser Val Val Phe Asp Phe Leu Ser Ser Asp Leu Lys Gln Val Gly
145                 150                 155                 160

Glu Tyr Ile Lys Asp Ala Asn Glu Lys Gln Ala Phe Gly Leu Lys Ile
                165                 170                 175

Ile Glu Ala Gln Glu Glu Glu Arg Arg Arg Leu Ser Arg Glu Ile His
            180                 185                 190

Asp Gly Pro Ala Gln Met Met Ala Asn Val Met Leu His Ser Glu Leu
        195                 200                 205

Ile Glu Arg Ile Tyr Gln Glu Arg Gly Ile Glu Glu Ala Leu Lys Glu
    210                 215                 220

Ile Arg Gly Leu Arg Arg Met Val Arg Ser Ser Leu Ala Glu Val Arg
225                 230                 235                 240

Arg Ile Ile Tyr Asp Leu Arg Pro Met Ala Leu Asp Asp Leu Gly Leu
                245                 250                 255

Val Pro Thr Leu Arg Lys Tyr Leu Glu Asn Ile Glu Glu Arg His Gly
            260                 265                 270

Leu Lys Val Thr Phe Lys His Phe Gly Val Glu Lys Arg Leu Ala Gln
        275                 280                 285

Gln Phe Glu Ile Ala Leu Phe Arg Leu Val Gln Glu Ala Val Gln Asn
    290                 295                 300

Ala Thr Lys His Ala Glu Pro Thr Glu Ile Ile Val Lys Ile Glu Leu
305                 310                 315                 320

Lys Pro Lys Asn Val Thr Leu Val Ile Arg Asp Asp Gly Lys Gly Phe
                325                 330                 335

Asp Leu Ser Glu Arg Lys Glu Ser Ser Phe Gly Leu Ile Gly Met Lys
```

```
            340                 345                 350

Glu Arg Val Asn Met Leu Asn Gly Lys Met Thr Ile His Ser Lys Pro
        355                 360                 365

Gln Glu Gly Thr Asn Ile Leu Ile Gln Leu Pro Val Ser Thr Asn
    370                 375                 380
```

<210> SEQ ID NO 30
<211> LENGTH: 1152
<212> TYPE: DNA
<213> ORGANISM: Bacillus clausii

<400> SEQUENCE: 30

```
ttgaaaaagc gaggagtatt catgacagac gtaacgatgc ttgatcatat aattacgcaa      60

acgcttgact cagttgggac gagtcgcgaa aaaatctttg aaatcggtga acgctcccgc     120

aatgagtatg aatacttgaa aaaggaatta gatcaagtca aagttaaatt aacacacgtt     180

attaatgatg tcgacgaaac cgtgttaaaa acaaaacacg cacgaaaccg gttagccaaa     240

gtaagcaagg aattcaatcg gtacacaagt gaggaagtcc gtacagcgta cgaacaagcc     300

agcgatttcc aagtacagct ggccgtgctt caacaagaag agatccaatt gcggattagg     360

cgggatgata ttgatcgccg cttgaaaaat cttcaggata cgattaatcg ggctgaacag     420

ctttctgtac agatgtccgt ggtgtttgac tttttatcaa gtgaccttaa gcaagtcggc     480

gaatacatta aagacgccaa tgaaaagcaa gcgttcggct taaaaataat cgaggcacag     540

gaagaagagc gtcgccgtct ttcccgggaa atccatgacg ggccagctca gatgatggca     600

aacgttatgc ttcattcaga attgattgaa cggatttacc aggaacgggg cattgaggaa     660

gcgcttaaag aaattcgcgg gttgcgccgt atggttcgtt cttcattggc agaggtaaga     720

agaatcattt atgatttgcg cccgatggcg ttggatgatt tagggctagt gcctacattg     780

agaaagtatt tggagaatat tgaagagcgt catggcttaa aagtcacttt taaacacttt     840

ggcgttgaaa agaggcttgc ccaacaattt gaaattgcgt tatttcgcct tgtgcaggaa     900

gcggtgcaaa atgcgactaa gcacgcagaa ccgactgaaa ttatcgtgaa gattgaattg     960

aaaccaaaaa atgtaacgct agtcattaga gatgacggca aaggatttga cctttctgaa    1020

agaaaggaat cttcgtttgg gttaatagc atgaaagaaa gggttaacat gctaaatggc    1080

aaaatgacga ttcattccaa accgcaagaa ggaacaaata ttttgattca actccctgtc    1140

tctacgaatt aa                                                        1152
```

<210> SEQ ID NO 31
<211> LENGTH: 419
<212> TYPE: PRT
<213> ORGANISM: Bacillus stearothermophilus

<400> SEQUENCE: 31

```
Met Glu Leu Gly Lys Thr Ile Lys Tyr Tyr Arg Ile Lys His Asn Met
 1               5                  10                  15

Thr Gln Ala Glu Leu Ala Asp Gly Ile Cys Ser Ile Pro His Leu Ser
            20                  25                  30

Lys Ile Glu Asn Asn Ile Tyr Lys Ala Asn His Ala Thr Ala Ser Leu
        35                  40                  45

Leu Leu Asp Arg Leu Gly Val Asn Ile Glu Asp Glu Tyr Ala Gln His
    50                  55                  60

Asn Glu Ile Lys Gln Ser Leu Glu Ala Phe Ile Glu Ala Ile Gln Phe
65                  70                  75                  80
```

-continued

```
Val Asp Val Gln Glu Ala Lys Arg Ile Gln Lys Ile Leu Val Glu Lys
                85                  90                  95

Glu Phe Ile Ile Ala Arg Thr Asp Tyr Ile Asn Thr Tyr His Leu Tyr
            100                 105                 110

Met Met Arg Tyr His Leu Met Asn Gly Ala Asn His Leu Ala Gln Glu
        115                 120                 125

Gln Arg Ala Ile Leu Asp Lys Asn Arg Thr Asn Leu Ser Ala Ile Glu
    130                 135                 140

Glu Leu Ser Tyr Arg Leu Phe Asn Gly Ile Leu Leu Val Asn Arg Asn
145                 150                 155                 160

Arg Leu Lys Glu Ala Lys Glu Ile Leu Leu Asp Leu Gln Ser Glu Asp
                165                 170                 175

Tyr Ser Ser Lys Tyr Ile Phe Val Arg Glu Val Ala Phe Val Leu Ala
            180                 185                 190

Gln Cys Phe Thr Gln Leu Asn Glu Pro Glu Lys Ala Ile Ile Tyr Ala
        195                 200                 205

Lys Glu Ala Leu Gln Ile Phe Lys Gln Glu Asp Asn Tyr Ile Arg Ala
    210                 215                 220

Phe His Thr Gln Met Leu Leu Gly Val Asn Tyr Thr Gln Met Asn Met
225                 230                 235                 240

Thr Glu Glu Ser Leu Arg Leu Tyr Lys Ile Leu Leu Arg Asn Thr Arg
                245                 250                 255

Leu Phe Ser Arg Asp Thr Leu Tyr Tyr Gln Ala Met Tyr Asn Tyr Gly
            260                 265                 270

Val Leu Leu Lys Lys Ile Gly Asn Tyr Glu Gln Ser His Glu Cys Phe
        275                 280                 285

Thr Lys Cys Ser Ala Tyr Tyr Asp Lys Asp Ser Gln Asn Tyr Val Phe
    290                 295                 300

Ser Leu Leu Ala Asp Ile Glu Val Leu Phe Gln Leu Lys Thr Asp Lys
305                 310                 315                 320

Lys Gln Ile Glu Ser Lys Leu Asn Glu Ile Ile Glu Ile Ser Ala Lys
                325                 330                 335

Arg Gly Tyr Lys Arg Ser Glu Leu Gln Ala Arg Tyr Tyr Ala His Arg
            340                 345                 350

Leu Lys Ala Asp Asp Ala Met Tyr Asn Phe Ile Glu Gln Glu Leu Leu
        355                 360                 365

Pro His Leu Asp Lys Leu Asp Asn Lys Glu Glu Pro Val His Tyr Ala
    370                 375                 380

Ile Glu Leu Ala Gln Trp Tyr Gln Lys Asn Gly Glu Tyr Glu Lys Ala
385                 390                 395                 400

Asn Glu Tyr Leu Asn Lys Tyr Ala Met Lys Val Lys Arg Arg Glu Phe
                405                 410                 415

Ser Ile Val


<210> SEQ ID NO 32
<211> LENGTH: 1260
<212> TYPE: DNA
<213> ORGANISM: Bacillus clausii

<400> SEQUENCE: 32

gtggagttag gcaaaacaat caaatactac cgaattaagc ataatatgac acaggcagaa      60

ctcgctgatg gtatttgctc cattccacac cttagcaaaa ttgaaaacaa catctataag     120

gccaaccatg ctacagcttc cctcttgctt gaccggcttg gcgtcaatat agaagatgaa     180
```

-continued

```
tatgcccaac acaacgagat taagcagtcg ctggaagcct ttattgaagc gatacaattt    240
gtggatgtac aggaagcaaa acggatacaa aaaatattag tcgagaagga atttatcatt    300
gcccgaacgg attacattaa tacgtaccat ttatacatga tgcgctacca cttgatgaac    360
ggagcgaacc accttgccca agaacagcga gccatcttag ataaaaaccg cacgaatttg    420
tccgcgatcg aagaactgtc ttaccgtctg ttcaatggca tcctcctagt aaaccgcaac    480
cgcttaaagg aagcaaaaga aattttgctt gacttgcaaa gtgaagacta ttcttccaaa    540
tacatttttg tccgtgaagt cgctttcgtg cttgcacagt gttttacaca gctaaatgag    600
ccagaaaaag caatcattta tgcaaaagag gcgctccaaa tttttaagca agaggacaat    660
tacattcgcg cttttcacac gcaaatgttg ctaggggtca attatacaca aatgaatatg    720
acagaggaat cccttcgcct ctataaaatc cttttgcgaa acacacgctt gtttagccgc    780
gacacgctct attaccaagc catgtacaat tacggcgtct tgcttaaaaa aattggcaac    840
tatgaacaaa gccatgaatg ttttacgaaa tgcagcgctt attacgacaa agacagccaa    900
aattacgtat tcagccttct cgcagacatc gaagttctct tccagttgaa aacggacaaa    960
aaacaaattg aatcaaaatt aaatgaaatt attgaaatta gtgcaaaacg tgggtacaaa   1020
cgctctgagc ttcaagcccg ctactatgcg caccgcttaa aagccgacga tgcgatgtac   1080
aactttatcg aacaggaact gctccctcat ctcgataagc ttgataataa agaagaacca   1140
gtccactatg caattgagct ggcgcaatgg taccagaaaa acggagagta cgaaaaagca   1200
aacgaatact taaataaata tgccatgaaa gtcaaaagac gtgaattttc cattgtatag   1260
```

SECRETION, TRANSCRIPTION AND SPORULATION GENES IN *BACILLUS CLAUSII*

The present application is a 371 of PCT/US03/03534, filed Feb. 6, 2003, which claims benefit to U.S. Provisional Application No. 60/355,258 filed Feb. 8, 2002.

FIELD OF THE INVENTION

The present invention relates to cells that have been genetically manipulated to have an altered capacity to produce expressed proteins. In particular, the present invention relates to Gram-positive microorganisms having exogenous nucleic acid sequences introduced therein and methods for producing proteins in such host cells, such as members of the genus *Bacillus*. More specifically, the present invention relates to the expression, production and secretion of a polypeptide of interest and to cells that have been genetically manipulated to have an altered capacity to produce expressed proteins. In particular, the present invention provides for the enhanced expression of a selected polypeptide by a microorganism.

BACKGROUND OF THE INVENTION

Gram-positive microorganisms, such as members of the genus *Bacillus*, have been used for large-scale industrial fermentation due, in part, to their ability to secrete their fermentation products into their culture media. Secreted proteins are exported across a cell membrane and a cell wall, and then are subsequently released into the external media. Secretion of polypeptides into periplasmic space or into their culture media is subject to a variety of parameters, which need to be carefully considered in industrial fermentations.

Indeed, secretion of heterologous polypeptides is a widely used technique in industry. Typically, cells are transformed with a nucleic acid encoding a heterologous polypeptide of interest to be expressed and thereby produce large quantities of desired polypeptides. This technique can be used to produce a vast amount of polypeptide over what would be produced naturally. These expressed polypeptides have a number of industrial applications, including therapeutic and agricultural uses, as well as use in foods, cosmetics, cleaning compositions, animal feed, etc. Thus, increasing expression of polypeptides is of great interest in many fields.

SUMMARY OF THE INVENTION

The present invention relates to cells that have been genetically manipulated to have an altered capacity to produce expressed proteins. In particular, the present invention relates to Gram-positive microorganisms having exogenous nucleic acid sequences introduced therein and methods for producing proteins in such host cells, such as members of the genus *Bacillus*. More specifically, the present invention relates to the expression, production and secretion of a polypeptide of interest and to cells that have been genetically manipulated to have an altered capacity to produce expressed proteins. In particular, the present invention provides for the enhanced expression of a selected polypeptide by a microorganism.

In some embodiments, the present invention provides nucleotide sequences encoding proteins involved in the secretion of peptides in Gram-positive host cells, as well as methods for increasing the secretion of proteins by cells.

In some embodiments, the present invention provides methods for increasing production and/or secretion of a polypeptide. In a preferred embodiment, the cell used in these methods expresses at least one secretion-associated protein derived from *B. clausii*. In particularly preferred methods, the cell is transformed to express the protein. In one embodiment, the method optionally comprises inactivating at least one secretion-associated protein in the cell. The method further comprises culturing the cell under conditions suitable for expression and secretion of the polypeptide.

The present invention also provides nucleic acid sequences encoding secretion-associated proteins. In a preferred embodiment, the nucleic acid sequences are derived from *Bacillus clausii*. In additional embodiments, variants of the *B. clausii* secretion factors are provided. In still further embodiments, at least partial sequence information for the deduced amino acid sequences of the secretion-associated proteins encoded by the nucleic acid sequences are provided.

The present invention also provides methods for the production of an alkaline protease in a host cell. In one embodiment, the hyperexpression of bc/2627 is used to induce enhance expression and/or secretion of the alkaline protease.

In yet another embodiment, the present invention provides *B. claussii* spollE and degU nucleic acid sequences. In some embodiments, these sequences are subjected to in vitro mutagenesis. In further embodiments, these mutagenized sequences are re-introduced into a host cell. In one embodiment the host cell is *B. clausii*, while in other embodiments, other organisms, including, but not limited to *B. subtilis* are used as host cells.

The present invention provides nucleotide sequences comprising a *Bacillus clausii* secretion factor, wherein the secretion factor is selected from the group consisting of SecA, SecD, SecE, SecF, SecG, SecY, Ffh, FtsY, SipS, SipT, SipV, and SipW. In some preferred embodiments, the nucleotide sequence is selected from the group consisting of SEQ ID NO: 10, SEQ ID NO:12, SEQ ID NO:14, SEQ ID NO:16, SEQ ID NO:18, SEQ ID NO:20, SEQ ID NO:8; SEQ ID NO:6, SEQ ID NO:22, SEQ ID NO:24, SEQ ID NO:26, and SEQ ID NO:28. In alternative embodiments a hybridizable nucleotide sequence remains hybridized to the nucleotide sequence of SEQ ID NO: 10, SEQ ID NO:12, SEQ ID NO:14, SEQ ID NO:16, SEQ ID NO:18, SEQ ID NO:20, SEQ ID NO:8; SEQ ID NO:6, SEQ ID NO:22, SEQ ID NO:24, SEQ ID NO:26, and SEQ ID NO:28, under stringency conditions of low stringency, moderate stringency, and high stringency. In additional embodiments, the present invention provides vectors comprising at least a portion of at least one of the nucleotide sequences set forth in SEQ ID NO: 10, SEQ ID NO:12, SEQ ID NO:14, SEQ ID NO:16, SEQ ID NO:18, SEQ ID NO:20, SEQ ID NO:8; SEQ ID NO:6, SEQ ID NO:22, SEQ ID NO:24, SEQ ID NO:26, and SEQ ID NO:28. In particularly preferred embodiments, the vector further comprises a nucleotide sequence encoding at least one polypeptide of interest. In still further embodiments, the present invention provides expression cassettes comprising the vector(s). In some preferred embodiments, the present invention provides host cells of the genus *Bacillus* comprising these expression cassette(s). In some preferred embodiments, the host cell secretes at least one *B. clausii* secretion factor selected from the group consisting of SecA, SecD, SecE, secF, SecG, SecY, Ffh, FtsY, SipS, SipT, SipV, and SipW. In alternative embodiments, secretion factor comprises an amino acid sequence selected from the group consisting of SEQ ID NO:9, SEQ ID NO:11, SEQ ID NO:13, SEQ ID NO:15, SEQ ID NO:17, SEQ ID NO:19, SEQ ID NO:7, SEQ ID NO:5, SEQ ID NO:21, SEQ ID NO:23, SEQ ID NO:25, and SEQ ID NO:27. In additional embodiments, the amino acid comprises a fragment of an amino acid sequence selected from the group consisting of SEQ ID NO:9, SEQ ID NO:11, SEQ ID NO:13, SEQ ID NO:15, SEQ ID NO:17, SEQ ID NO:19, SEQ ID NO:7, SEQ ID NO:5, SEQ ID NO:21, SEQ ID NO:23, SEQ ID NO:25, and SEQ ID NO:27. In still further embodiments, the amino acid comprises a variant of an amino acid sequence selected from the group consisting of SEQ ID NO:9, SEQ ID NO:11, SEQ ID NO:13, SEQ ID NO:15, SEQ ID NO:17, SEQ ID NO:19, SEQ ID NO:7, SEQ ID NO:5, SEQ ID NO:21, SEQ ID NO:23, SEQ ID NO:25, and SEQ ID NO:27.

The present invention also provides nucleotide sequences comprising a *Bacillus clausii* transcription factor, wherein the transcription factor is selected from the group consisting of DegS, DegU, and BcI2627. In some preferred embodiments, the nucleotide sequence is selected from the group consisting of SEQ ID NO: 4, SEQ ID NO:30, and SEQ ID NO:32. In further embodiments, the present invention provides hybridizable nucleotide sequences that remain hybridized under stringency conditions of low stringency, moderate stringency, and high stringency to a nucleotide sequence comprising a *Bacillus clausil* transcription factor, wherein said transcription factor is selected from the group consisting of DegS, DegU, and Bcl2627, and wherein said nucleotide sequence is selected from the group consisting of SEQ ID NO: 4, SEQ ID NO:30, and SEQ ID NO:32 . In still further embodiments, the present invention provides vectors comprising at least a portion of a nucleotide sequence selected from the group consisting of SEQ ID NO: 4, SEQ ID NO:30, and SEQ ID NO:32. In some preferred embodiments, the vectors further comprise a nucleotide sequence encoding at least one polypeptide of interest. In still further embodiments, the present invention provides expression cassettes comprising these vector(s). In additional embodiments, the present invention provides host cells of the genus *Bacillus* comprising the expression cassette(s). In still further embodiments, the host cell secretes at least one *B. clausii* transcription factor. In additional embodiments, the transcription factor comprises an amino acid sequence selected from the group consisting of SEQ ID NO:3, SEQ ID NO:29, and SEQ ID NO:31. In some embodiments, the amino acid comprises a fragment of an amino acid sequence selected from the group consisting of SEQ ID NO:3, SEQ ID NO:29, and SEQ ID NO:31. In some alternative embodiments, the amino comprises a variant of an amino acid sequence selected from the group consisting of SEQ ID NO:3, SEQ ID NO:29, and SEQ ID NO:31.

The present invention also provides a nucleotide sequence comprising the *Bacillus clausii* sporulation factor SpollE protein. In some embodiments, the sequence comprises SEQ ID NO: 2. In further embodiments, the present invention provides hybridizable nucleotide sequences that remain hybridized under stringency conditions of low stringency, moderate stringency, and high stringency to a nucleotide sequence comprising the *Bacillus clausii* sporulation factor SpollE protein, wherein said sequence comprises SEQ ID NO: 2. The present invention also provides vectors comprising at least a portion of the nucleotide sequence of SEQ ID NO:2. In some preferred embodiments, the vectors further comprise a nucleotide sequence encoding at least one polypeptide of interest. In still further embodiments, the present invention provides expression cassettes comprising these vector(s). In additional embodiments, the present invention provides host cells of the genus *Bacillus* comprising the expression cassette(s). In some particularly preferred embodiments, the host cell secretes at least one *B. clausii* sporulation factor. In still further embodiments, the sporulation factor comprises the amino acid sequence SEQ ID NO:1. In some embodiments, the amino acid comprises a fragment of the amino acid sequence set forth SEQ ID NO: 1, while in alternative embodiments the amino acid comprises a variant of the amino acid sequence set forth in SEQ ID NO:1.

The present invention further provides methods for producing a protein of interest comprising the steps of: culturing a *Bacillus* host cell under suitable conditions, wherein the *Bacillus* host cell comprises a nucleotide sequence encoding a protein of interest, and wherein the host cell has been transformed with a nucleotide sequence encoding a protein comprising the amino acid sequence selected from the group consisting of SEQ ID NOs:1, 3, 5, 7, 9, 11, 13, 15, 17, 19, 21, 23, 25, 27, 29, and 31; and allowing expression of the protein of interest. In some embodiments, the amino acid sequence is at least 85% identical to the sequence of a protein having an amino acid sequence selected from the group consisting of of SEQ ID NOs:1, 3, 5, 7, 9, 11, 13, 15, 17, 19, 21, 23, 25, 27, 29, and 31. In further embodiments, the amino acid sequence comprises an amino acid sequence that is a variant of an amino acid sequence selected from the group consisting of SEQ ID NOs:1, 3, 5, 7, 9, 11, 13, 15, 17, 19, 21, 23, 25, 27, 29, and 31. In alternative embodiments, the amino acid sequence comprises an amino acid sequence that is a fragment of an amino acid sequence selected from the group consisting of SEQ ID NOs:1, 3, 5, 7, 9, 11, 13, 15, 17, 19, 21, 23, 25, 27, 29, and 31. The present invention also provides amino acid sequences that comprise hybrid *B. clausii* sequences.

DESCRIPTION OF THE FIGURES

FIG. 1 shows the deduced amino acid sequence for SpollE from *B. clausii* (SEQ ID NO:1).

FIG. 2 shows the DNA sequence for spollE from *B. clausii* (SEQ ID NO:2).

FIG. 3A shows the deduced amino acid sequence for DegU from *B. clausii* (SEQ ID NO:3).

FIG. 3B shows the deduced amino acid sequence for DegS from *B. clausii* (SEQ ID NO:29).

FIG. 4A shows the DNA sequence for degU from *B. clausii* (SEQ ID NO:4).

FIG. 4B shows the DNA sequence for degS from *B. clausii* (SEQ ID NO:30).

FIG. 5 show the deduced amino acid sequence for FtsY from *B. clausii* (SEQ ID NO:5).

FIG. 6 shows the DNA sequence for ftsY from *B. clausii* (SEQ ID NO:6).

FIG. 7 show the deduced amino acid sequence for ffh from *B. clausii* (SEQ ID NO:7).

FIG. 8 shows the DNA sequence for ffh from *B. clausii* (SEQ ID NO:8).

FIG. 9 show the deduced amino acid sequence for SecA from *B. clausii* (SEQ ID NO:9).

FIG. 10 shows the DNA sequence for secA from *B. clausii* (SEQ ID NO:10).

FIG. 11 show the deduced amino acid sequence for SecD from *B. clausii* (SEQ ID NO:11).

FIG. 12 shows the DNA sequence for secD from *B. clausii* (SEQ ID NO:12).

FIG. 13 show the deduced amino acid sequence for SecE from *B. clausii* (SEQ ID NO:13).

FIG. 14 shows the DNA sequence for secE from *B. clausii* (SEQ ID NO:14).

FIG. 15 show the deduced amino acid sequence for SecF from *B. clausii* (SEQ ID NO:15).

FIG. 16 shows the DNA sequence for secF from *B. clausii* (SEQ ID NO:16). The nucleotide residue designated as "M" means that the nucleotide can be either a C or an A.

FIG. 17 show the deduced amino acid sequence for SecG from *B. clausii* (SEQ ID NO:17).

FIG. 18 shows the DNA sequence for secG from *B. clausii* (SEQ ID NO:18).

FIG. 19 show the deduced amino acid sequence for SecY from *B. clausii* (SEQ ID NO:19).

FIG. 20 shows the DNA sequence for secY from *B. clausii* (SEQ ID NO:20).

FIG. 23 depicts the alignment of phosphorelay component proteins Spo0F, Spo0B and Spo0A of *B. subtilis* (Bsu), *B. clausii*, and *B. halodurans* (Bhalo). Residues conserved in all three species are denoted with an asterisk; those conserved between subtilis and *clausii* are in red, between *clausii* and halodurans in blue and between subtilis and halodurans in green. The mosaic nature of the proteins is especially evident among the relatively low homology Spo0B proteins, where, in non-conserved positions, approximately 10% identity is seen between *B. clausii* vs *B. subtilis* as well as *B. clausii* vs *B. halodurans*, while approximately 20% identity is observed for the *B. subtilis/B. halodurans* comparison.

Active site D54 (0F), H30 (0B) and D56 (0A) residues are marked (Pi). The DNA binding helix-turn helix sequence of Spo0A is overlined (_H-T-H_). Residues conferring specificity of interaction (Hoch and Varughese, J. Bacteriol., 183: 4941–4949 [2001]) between response regulators, i.e. preventing cross-talk, are shown for Spo0F helix 1 (!), loop 4 (#) and helix 5 ($); residues contacted in Spo0B are shown with the corresponding designation as are the homologous residues in Spo0A. While these specificity residues are completely conserved in Spo0F and Spo0A, with the exception of the conservative E21 D substitution in *B. halodurans* Spo0A, only four of eleven contact residues of Spo0B are totally conserved, with additional residues 44,45, 67 and 100 conservatively substituted. This may reflect some degree of flexibility within this molecular recognition of partners in phosphorelay signal transduction systems, although assuredly these interactions must remain highly specific.

Figure 24:
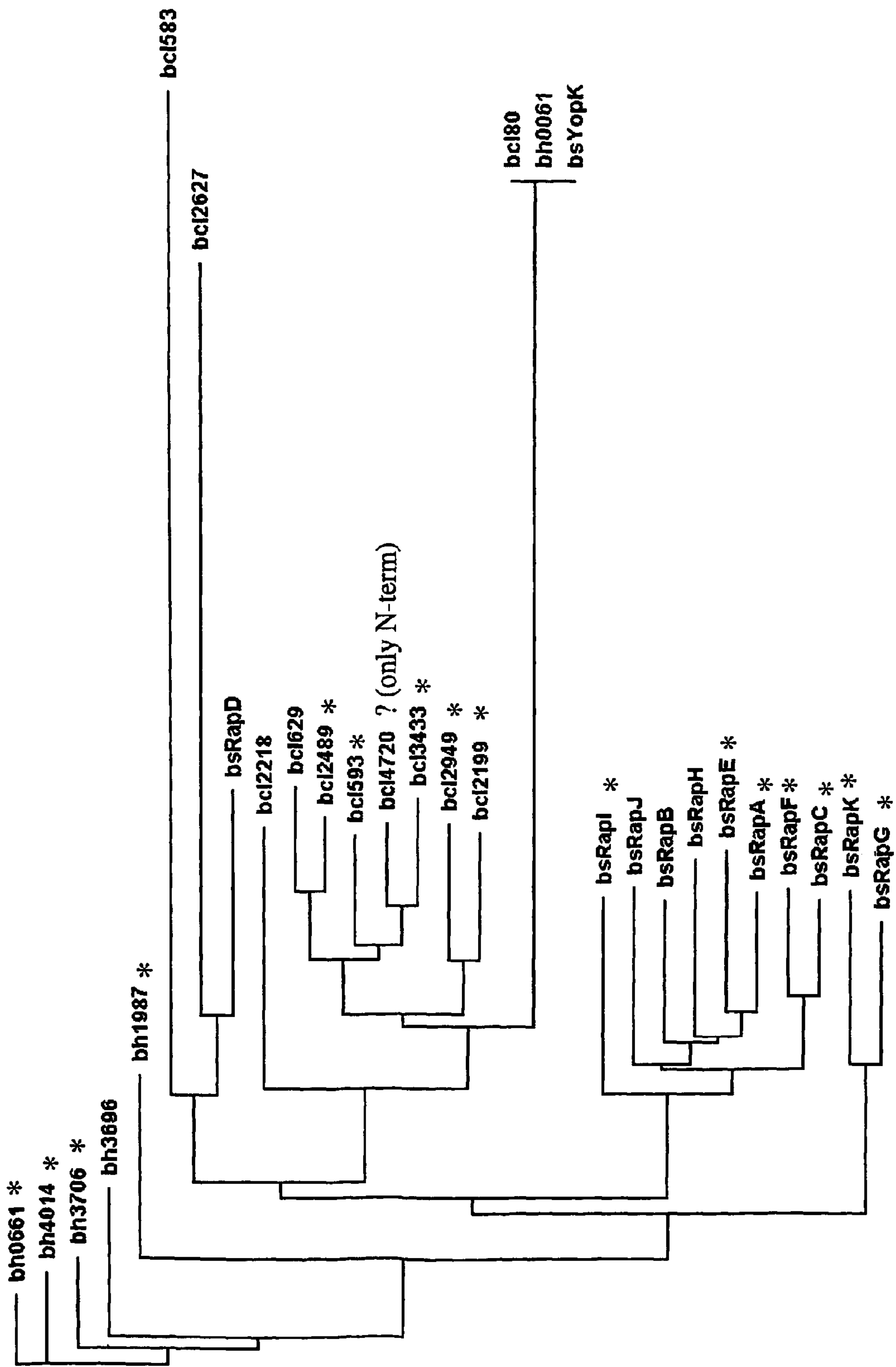

FIG. 24 depicts a multiple sequence alignment of putative Rap proteins from three *Bacillus* species. The alignment was performed using ClustalW. The dendrogram was constructed using the Phylip software package. For computation of the distance matrix the Dayhoff PAM matrix was used ("bh" indicates sequences from *Bacillus halodurans*, "bcl" indicates sequences from *Bacillus clausii* and "bs" indicates sequences from *Bacillus subtilis*).

Although it is not intended that the present invention be limited to any particular mechanism or theory, the tree suggests an early acquisition of a common ancestral gene followed by separate duplications in the three genomes. *B. halodurans* is unique in the small number of Rap phosphatases encoded in its genome relative to subtilis and clausi. *B. subtilis* RapD, an from the other subtilis Rap sequences, is most closely related to a pair of *B. clausii* Rap proteins which likewise fall outside the main *B. clausii* grouping. YopK in *B. subtilis*, similar to Rap phosphatases and followed by a potential Phr-encoding gene (but currently annotated as of unknown function), is homologous to *clausii* bcl80 and *halodurans* BH0061. *B. clausii* bcl80 is much shorter than YopK, sharing homology with only N-terminal 160 amino acids of 386 amino acid YopK. BH0061 is annotated as a 4-diphosphocytidyl-2-C-methyl-D-erythritol kinase and is shorter than YopK by 100 amino acids.

FIG. 25 show the deduced amino acid sequence for SipS from *B. clausii* (SEQ ID NO:21).

FIG. 26 shows the DNA sequence for sips from *B. clausii* (SEQ ID NO:22).

FIG. 27 show the deduced amino acid sequence for SipT from *B. clausii* (SEQ ID NO:23).

FIG. 28 shows the DNA sequence for sipT from *B. clausii* (SEQ ID NO:24).

FIG. 29 show the deduced amino acid sequence for SipV from *B. clausii* (SEQ ID NO:25).

FIG. 30 shows the DNA sequence for sipV from *B. clausii* (SEQ ID NO:26).

FIG. 31 show the deduced amino acid sequence for SipW from *B. clausii* (SEQ ID NO:27).

FIG. 32 shows the DNA sequence for sipW from *B. clausii* (SEQ ID NO:28).

FIG. 33 shows the deduced amino acid sequence of bcl 2627 which is homologous to the transcriptional activator gene nprA from *Bacillus stearothermophilus* (SEQ ID NO:31).

FIG. 34 shows the DNA sequence of the gene bcl2627 from *B. clausii* (SEQ ID NO:32).

DESCRIPTION OF THE INVENTION

The invention will now be described in detail by way of reference only using the following definitions and examples.

All patents and publications, including all sequences disclosed within such patents and publications, referred to herein are expressly incorporated by reference.

The present invention relates to cells that have been genetically manipulated to have an altered capacity to produce expressed proteins. In particular, the present invention relates to Gram-positive microorganisms having exogenous nucleic acid sequences introduced therein and methods for producing proteins in such host cells, such as members of the genus *Bacillus*. More specifically, the present invention relates to the expression, production and secretion of a polypeptide of interest and to cells that have been genetically manipulated to have an altered capacity to produce expressed proteins. In particular, the present invention provides for the enhanced expression of a selected polypeptide by a microorganism.

Definitions

All patents and publications, including all sequences disclosed within such patents and publications, referred to herein are expressly incorporated by reference. Unless defined otherwise herein, all technical and scientific terms used herein have the same meaning as commonly understood by one of ordinary skill in the art to which this invention belongs (See e.g., Singleton, et al., Dictionary of Microbiology and Molecular Biology, 2d Ed., John Wiley and Sons, New York [1994]; and Hale and Marham, The Harper Collins Dictionary of Biology, Harper Perennial, N.Y. [1991], both of which provide one of skill with a general dictionary of many of the terms used herein). Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined immediately below are more fully defined by reference to the Specification as a whole.

As used herein, "host cell" refers to a cell that has the capacity to act as a host and expression vehicle for an expression cassette according to the invention. In one embodiment, the host cell is a Gram positive microorganism. In some preferred embodiments, the term refers to cells in the genus *Bacillus.*

As used herein, "the genus *Bacillus*" includes all members known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, and B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus.*

The term "polypeptide," as used herein, refers to a compound made up of amino acid residues linked by peptide bonds. The term "protein" as used herein, may be synonymous with the term "polypeptide" or may refer, in addition, to a complex of two or more polypeptides. Thus, the terms "protein," "peptide," and "polypeptide" are used interchangeably.

Additionally, a "protein of interest," or "polypeptde of interest," refers to the protein/polypeptide to be expressed and secreted by the host cell. The protein of interest may be any protein that up until now has been considered for expression in prokaryotes and/or eukaryotes. In one embodiment, the protein of interest which is translocated by the secretion-associated proteins or systems utilized by the host cell include proteins comprising a signal peptide. The protein of interest may be either homologous or heterologous to the host. In some embodiments, the protein of interest is a secreted polypeptide, particularly an enzyme which is selected from amylolytic enzymes, proteolytic enzymes, cellulytic enzymes, oxidoreductase enzymes and plant wall degrading enzymes. In further embodiments, these enzyme include amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, galactosidases and chitinases. In still further embodiments, the expressed polypeptide is a hormone, growth factor, receptor, vaccine, antibody, or the like. While it is not intended that the present invention be limited to any particular protein/polypeptide, in some most preferred embodiments, the expressed polypeptide is a protease.

As used herein, the terms "chimeric polypeptide" and "fusion polypeptide" are used interchangeably to refer to a protein that comprises at least two separate and distinct regions that may or may not originate from the same protein. For example, a signal peptide linked to the protein of interest wherein the signal peptide is not normally associated with the protein of interest would be termed a chimeric polypeptide or chimeric protein.

As used herein, "secretion-associated protein" as used herein refers to a protein involved in the secretion of a protein of interest from a host cell. The secretion-associated proteins may assist a nascent (i.e., during or immediately after synthesis), protein to fold correctly, to assist in the movement of a protein from the intracellular to extracellular environment (e.g., moving through the cytoplasm to the cell membrane and/or across the membrane/cell wall to the extracellular milieu, etc.), appropriate processing and the like. Proteins involved in any aspect of the movement of a protein once it is synthesized intracellularly until it emerges on the external surface of the cell membrane are considered to have secretion-associated activity or function. In one embodiment, a secretion-associated protein comprises a protein involved in assisting the nascent protein of interest achieve a correctly folded conformation. In another embodiment, the secretion-associated protein comprises a protein from the Sec pathway. The terms "secretion-associated protein," "secretion-associated factor," and "secretion factor" are all used interchangeably herein.

As used herein, the term "hybrid" refers to a sequence (e.g., a secretion factor) containing sequences derived from two or more orthologs. Thus, a "hybrid gene" or "hybrid protein" is a gene or protein, respectively, in which two or more fragment sequences are derived from two or more strains of *Bacillus.*

In an embodiment, the orthologous sequences comprise a sequence from a single ortholog. In another embodiment, the orthologous sequences comprise less than 5 sequences from a single ortholog. In a further embodiment, the orthologous sequences comprise sequences from two orthologs. In one embodiment, the orthologous sequences comprise a single amino acid. In another embodiment, the orthologous sequences comprise from between two amino acids to five, 10, 15, 20 aminio acids. In a further embodiment, the orthologous sequences comprise from about 2% to about 50%, of the total amino acid residues, of the secretion factor sequence.

In another embodiment, the orthologous sequences comprise great than two amino acids and less than five, 10, 15, 20, 25, 30, 35, 40, 45 or 50 amino acids. In a further embodiment, the orthologous sequences comprise less than about 50%, in total, of the hybrid secretion factor sequence when compared to the wild-type *B. clausii* secretion factor.

As used herein, the terms "chimeric polypeptide" and "fusion polypeptide" are used interchangeably to refer to a protein that comprises at least two separate and distinct regions that may or may not originate from the same protein. For example, a signal peptide linked to the protein of interest wherein the signal peptide is not normally associated with the protein of interest would be termed a chimeric polypeptide or chimeric protein.

As used herein, the terms "chimeric DNA construct" and "heterologous nucleic acid construct," refer to a gene (i.e., one that has been introduced into a host) that is comprised of parts of different genes, including regulatory elements. Thus, in some embodiments, a chimeric gene is an endogenous gene operably linked to a promoter that is not its native promoter. A chimeric gene construct for transformation of a host cell is typically composed of a transcriptional regulatory region (promoter) operably linked to a protein coding sequence, or, in a selectable marker chimeric gene, to a selectable marker gene encoding a protein conferring antimicrobial resistance to transformed cells. In one embodiment, a typical chimeric gene construct of the present invention useful for transformation into a host cell comprises a transcriptional regulatory region that is constitutive or inducible, a signal peptide coding sequence, a protein coding sequence, and a terminator sequence. In other embodiments, the chimeric gene comprises a promoter operably linked to a phr gene. In yet other embodiments, the chimeric gene comprises a promoter operably linked to a gene encoding a protein of interest. In still further embodiments, chimeric gene constructs also comprise a second DNA sequence encoding a signal peptide if secretion of the target protein is desired.

Thus, "hybrid" is used to describe the secretion factor and the nucleotide encoding it, while "chimeric" is used to describe the DNA construct with regulatory elements. Thus, the chimeric gene or chimeric DNA construct may encode a hybrid secretion factor.

As used herein, "variant" refers to a protein which is derived from a precursor protein (e.g., a *B. clausii* secretion factor) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. A "*B. clausii* secretion factor variant" refers a *B. clausii* secretion factor modified as described above. The preparation of a *B. clausii* secretion factor variant is preferably achieved by modifying a DNA sequence which encodes for the native protein, transformation of that DNA sequence into a suitable host, and expression of the modified DNA sequence to form the derivative enzyme. The variant *B. clausii* secretion factors of the invention include peptides comprising altered amino acid sequences in comparison with a precursor enzyme amino acid sequence wherein the variant *B. clausii* secretion factor retains the characteristic secretion factor nature of the precursor *B. clausii* secretion factor but which may have altered properties in some specific aspect. For example, in some embodiments, variant *B. clausii* secretion factors have increased stability under oxidative conditions but retain their characteristic secretion factor activity. However, the activity of the variant may be increased or decreased relative to the precursor secretion factor. It is contemplated that the variants according to the present invention may be derived from a DNA fragment encoding a *B. clausii* secretion factor variant wherein the functional activity of the expressed *B. clausii* secretion factor variant is retained. For example, in some embodiments, a DNA fragment encoding a *B. clausii* secretion factor further includes a DNA sequence or portion thereof encoding a hinge or linker attached to the *B. clausii* secretion factor DNA sequence at either the 5' or 3' end wherein the functional activity of the encoded *B. clausii* secretion factor domain is retained.

A "signal peptide," as used herein, refers to an amino-terminal extension on a protein to be secreted. "Signal sequence" is used interchangeably herein. In most preferred embodiments, secreted proteins use an amino-terminal protein extension which plays a crucial role in the targeting to and translocation of precursor proteins across the membrane and which is proteolytically removed by a signal peptidase during or immediately following membrane transfer. In preferred embodiments, the signal sequence is the sec-dependent signal peptides derived from *Bacillus*.

As used herein, the term "enhanced" refers to improved production of proteins of interest. In preferred embodiments, the present invention provides enhanced (i.e., improved) production and secretion of a protein of interest. In these embodiments, the "enhanced" production is improved as compared to the normal levels of production by the host (e.g., wild-type cells). Thus, for heterologous proteins, basically any expression is enhanced, as the cells normally do not produce the protein.

As used herein, the terms "isolated" and "purified" refer to a nucleic acid or amino acid that is removed from at least one component with which it is naturally associated.

As used herein, the term "heterologous protein" refers to a protein or polypeptide that does not naturally occur in a host cell. Examples of heterologous proteins include enzymes such as hydrolases including proteases, cellulases, amylases, other carbohydrases, and lipases; isomerases such as racemases, epimerases, tautomerases, or mutases; transferases, kinases and phosphatases, hormones, growth factors, cytokines, antibodies and the like. Thus, in some embodiments, heterologous proteins comprise therapeutically significant protein or peptides (e.g., growth factors, cytokines, ligands, receptors and inhibitors), as well as vaccines and antibodies. In alternate embodiments, the protein is a commercially important industrial protein or peptide. It is intended that the term encompass protein that are encoded by naturally occurring genes, mutated genes, and/or synthetic genes.

As used herein, the terms "heterologous nucleic acid construct" and "heterologous nucleic acid sequence" refer to a portion of a genetic sequence that is not native to the cell in which it is expressed. "Heterologous," with respect to a control sequence refers to a control sequence (i.e., promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. In some embodiments, "heterologous nucleic acid constructs" contain a control sequence/DNA coding sequence combination that is the same as, or different from a control sequence/DNA coding sequence combination found in the native cell.

As used herein, the term "homologous protein" refers to a protein or polypeptide native or naturally occurring in a host cell. The present invention encompasses host cells producing the homologous protein via recombinant DNA technology. The present invention further encompasses a host cells with one or more deletions or one or more interruptions of the nucleic acid encoding the naturally occurring homologous protein or proteins, such as, for example, a protease, and having nucleic acid encoding the homologous protein or proteins re-introduced in a recombinant form (i.e., in an expression cassette). In other embodiments, the host cell produces the homologous protein.

As used herein, the term "nucleic acid molecule" includes RNA, DNA and cDNA molecules. It will be understood that, as a result of the degeneracy of the genetic code, a multitude of nucleotide sequences encoding a given protein may be produced.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the terms "expression cassette" and "expression vector" refer to a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the term "selectable marker" refers to a gene capable of expression in host cell which allows for ease of selection of those hosts containing the vector. Examples of such selectable markers include but are not limited to antimicrobials, (e.g., kanamycin, erythromycin, actinomycin, chloramphenicol and tetracycline). Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the chromosome of the microorganism to be transformed. A residing selectable marker encodes a gene that is different from the selectable marker on the transforming DNA construct.

As used herein, the term "promoter" refers to a nucleic acid sequence that functions to direct transcription of a downstream gene. In preferred embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, that may or may not include regions preceding and following the coding region (e.g. 5' untranslated (5' UTR) or "leader" sequences and 3' UTR or "trailer" sequences), as well as intervening sequences (introns) between individual coding segments (exons).

In some embodiments, the gene encodes therapeutically significant proteins or peptides, such as growth factors, cytokines, ligands, receptors and inhibitors, as well as vaccines and antibodies. The gene may encode commercially important industrial proteins or peptides, such as enzymes (e.g., proteases, carbohydrases such as amylases and glucoamylases, cellulases, oxidases and lipases). However, it is not intended that the present invention be limited to any particular enzyme or protein. In some embodiments, the gene of interest is a naturally-occurring gene, a mutated gene or a synthetic gene.

As used herein, a "deletion" is defined as a change in either nucleotide or amino acid sequence in which one or more nucleotides or amino acid residues, respectively, are absent.

As used herein, an "insertion" or "addition" is that change in a nucleotide or amino acid sequence which has resulted in the addition of one or more nucleotides or amino acid residues, respectively, as compared to the naturally occurring sequence (e.g., a *B. clausii* secretion factor).

As used herein, a "substitution" results from the replacement of one or more nucleotides or amino acids by different nucleotides or amino acids, respectively.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387–395 [1984]).

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351–360 [1987]). The method is similar to that described by Higgins and Sharp (Higgins and Sharp, CABIOS 5:151–153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403–410, [1990]; and Karlin et al., Proc. Natl. Acad. Sci. USA 90:5873–5787 [1993]). A particularly useful BLAST program is the WU-BLAST-2 program (See, Altschul et al., Meth. Enzymol., 266:460–480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the sequence shown in the nucleic acid figures. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of the nucleic acid figures, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

As used herein, the term "hybridization" refers to the process by which a strand of nucleic acid joins with a complementary strand through base pairing, as known in the art.

As used herein, "maximum stringency" refers to the level of hybridization that typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature I of the nucleic acid binding complex or probe. For example, "maximum stringency" typically occurs at about Tm-5° C. (50 below the Tm of the probe); "high stringency" at about 5–10° C. below the Tm; "intermediate stringency" at about 10–20° C. below the Tm of the probe; and "low stringency" at about 20–25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5× Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination, "recombining," or generating a Recombined" nucleic acid is generally the assembly of two or more nucleic acid fragments wherein the assembly gives rise to a chimeric gene.

As used herein, the terms "transformed," "stably transformed," and "transgenic" used in reference to a cell means the cell has a non-native (heterologous) nucleic acid sequence integrated into its genome or as an episomal plasmid that is maintained through two or more generations.

As used herein, the term "expression" refers to the process by which a polypeptide is produced based on the nucleic acid sequence of a gene. The process includes both transcription and translation.

As used herein, the term "introduced" used in the context of inserting a nucleic acid sequence into a cell, means "transfection," "transformation," or "transduction," and includes reference to the incorporation of a nucleic acid sequence into a eukaryotic or prokaryotic cell where the nucleic acid sequence may be incorporated into the genome of the cell (e.g., chromosome, plasmid, plastid, or mitochondrial DNA), converted into an autonomous replicon, or transiently expressed (for example, transfected mRNA).

As used herein, "transforming DNA," "transforming sequence," and "DNA construct" refer to DNA that is used to introduce sequences into a host cell or organism. Transforming DNA is DNA used to introduce sequences into a host cell or organism. The DNA may be generated in vitro by PCR or any other suitable techniques. In some preferred embodiments, the transforming DNA comprises an incoming sequence, while in other preferred embodiments it further comprise an incoming sequence flanked by homology boxes. In yet a further embodiment, the transforming DNA may comprise other non-homologous sequences, added to the ends (i.e., stuffer sequences or flanks). The ends can be closed such that the transforming DNA forms a closed circle, such as, for example, insertion into a vector.

In a preferred embodiment, mutant DNA sequences are generated with site saturation mutagenesis in at least one codon. In another preferred embodiment, site saturation mutagenesis is performed for two or more codons. In a further embodiment, mutant DNA sequences have more than 40%, more than 45%, more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

In an alternative embodiment, the transforming DNA sequence comprises homology boxes without the presence of an incoming sequence. In this embodiment, it is desired to delete the endogenous DNA sequence between the two homology boxes. Furthermore, in some embodiments, the transforming sequences are wild-type, while in other embodiments, they are mutant or modified sequences. In addition, in some embodiments, the transforming sequences are homologous, while in other embodiments, they are heterologous.

As used herein, the term "incoming sequence" refers to a DNA sequence that is introduced into the *Bacillus* chromosome or genome. In preferred embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In some embodiments, the incoming sequence includes a selectable marker, such as a gene that confers resistance to an antimicrobial.

In one embodiment, the incoming sequence encodes at least one heterologous protein including, but not limited to hormones, enzymes, and growth factors. In another embodiment, the enzyme includes, but is not limited to hydrolases, such as protease, esterase, lipase, phenol oxidase, permease, amylase, pullulanase, cellulase, glucose isomerase, laccase and protein disulfide isomerase.

In alternative embodiments, the incoming sequence encodes a functional wild-type gene or operon, a functional mutant gene or operon, or a non-functional gene or operon. In some embodiments, the non-functional sequence may be inserted into a gene to disrupt function of the gene.

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A B C, gene B is flanked by the A and C gene sequences). In a preferred embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence.

As used herein, the term "stuffer sequence" refers to any extra DNA that flanks homology boxes (typically vector sequences). However, the term encompasses any non-homologous DNA sequence. Not to be limited by any theory, a stuffer sequence provides a noncritical target for a cell to initiate DNA uptake.

As used herein, the term "chromosomal integration" refers to the process whereby the incoming sequence is introduced into the chromosome of a host cell (e.g., *Bacillus*). The homology boxes of the transforming DNA align with homologous regions of the chromosome. Subsequently, the sequence between the homology boxes is replaced by the incoming sequence in a double crossover (i.e., homologous recombination).

As used herein, the term "homologous recombination" refers to the exchange of DNA fragments between two DNA molecules or paired chromosomes (e.g., during crossing over) at the site of identical nucleotide sequences. In a preferred embodiment, chromosomal integration is by homologous recombination.

As used herein, the term "library of mutants" refers to a population of cells which are identical in most of their genome but include different homologues of one or more genes. Such libraries find use for example, in methods to identify genes or operons with improved traits.

As used herein, the terms "hypercompetent" and "super competent" mean that greater than 1% of a cell population is transformable with chromosomal DNA (e.g., *Bacillus* DNA). Alternatively, the terms are used in reference to cell populations in which greater than 10% of a cell population is transformable with a self-replicating plasmid (e.g., a *Bacillus* plasmid). Preferably, the super competent cells are transformed at a rate greater than observed for the wild-type or parental cell population. Super competent and hypercompetent are used interchangeably herein As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a gene or a vector encoding a gene which permits the amplification of that gene under appropriate growth conditions.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

DETAILED DESCRIPTION OF THE INVENTION

The present invention relates to cells that have been genetically manipulated to have an altered capacity to produce expressed proteins. In particular, the present invention relates to Gram-positive microorganisms having exogenous nucleic acid sequences introduced therein and methods for producing proteins in such host cells, such as members of the genus *Bacillus*. More specifically, the present invention relates to the expression, production and secretion of a polypeptide of interest and to cells that have been genetically manipulated to have an altered capacity to produce expressed proteins. In particular, the present invention provides for the enhanced expression of a selected polypeptide by a microorganism.

Many industrially important products (e.g., enzymes, hormones, growth factors, and other proteins) are produced from members of the genus *Bacillus* in large scale fermentation processes, including without limitation, proteases, lipases, amylases, and beta-glucanases. These products (i.e., proteins of interest) are either homologous or heterologous to the host. For homologous proteins, "overexpression" refers to expression above normal levels in the host cell. For heterologous proteins, any expression is of course "overexpression." Thus, it is advantageous to have a cell that will fail to sporulate yet possesses enhanced expression of gene(s) of interest.

In order to address some of the needs in the art, in one embodiment the present invention provides nucleic acid sequences encoding secretion factors involved in protein secretion from Gram-positive host cells. In some embodiments, these sequences find use in the replacement of a host *Bacillus* species' genes with the inventive *B. clausii* genes provided herein to alter the secretion profile of proteins of interest, such that there is a greater level of protein production by the transformed host *Bacillus* cell. In one preferred embodiment, the host *Bacillus* cell is *B. subtilis*. In an alternative embodiment, the host cell is *B. clausii*. In a further embodiment, the present invention provides methods to enhance the secretion (i.e., production and expression) of any protein of interest.

*Bacillus clausii* Nucleotide Sequences

During the development of the present invention, a large number of bacterial strains from extreme environments were collected. An obligate alkalophilic *Bacillus* was identified as *Bacillus clausii*, based on 16S RNA gene sequences. This strain was given the designation "PB92." Strain PB92 was deposited in the ATCC collection as ATCC 31408, in the collection of the Laboratory for Microbiology of the Technical University of Delft as OR-60, and in the collection of the Fermentation Research Institute of the Agency of Industrial Science and Technology in Japan as FERM-P 3304.

Figure 21:
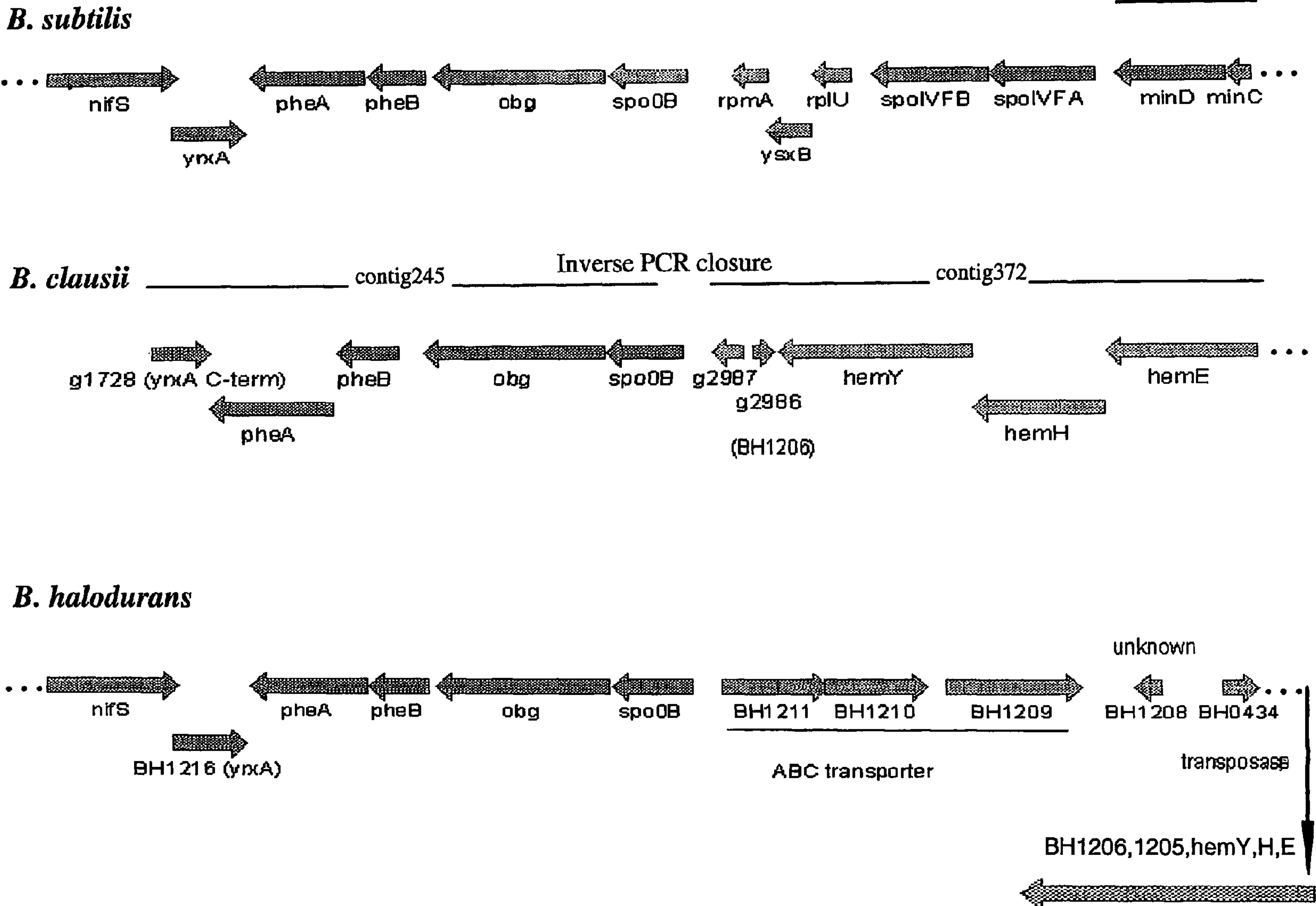
FIG. 21 depicts the synteny between three species in the spo0B region. Chromosome walking by inverso PCR was employed to connect two contigs in the spo0B region of *B. clausii*. The resulting closure allowed us to look at conservation of (or lack of) gene organization in this region containing the gene for the central component of the developmental phosphorelay signal transduction system. The yrxA to spo0B regions of the three chromosomes is conserved; nifS in *B. clausii* is on a third contig which has not to date been connected. The arrangement of genes in the region upstream of spo0B in *B. subtilis* is unique among the species compared here. The spo0B-contiguous hemEHY region in *B. clausii* is separated by an ABC transporter operon and a transposase gene in *B. halodurans*. This situation will most likely prove common in the *clausii* /halodurans comparison, as both species have in excess of 100 transposase genes.
Figure 22:
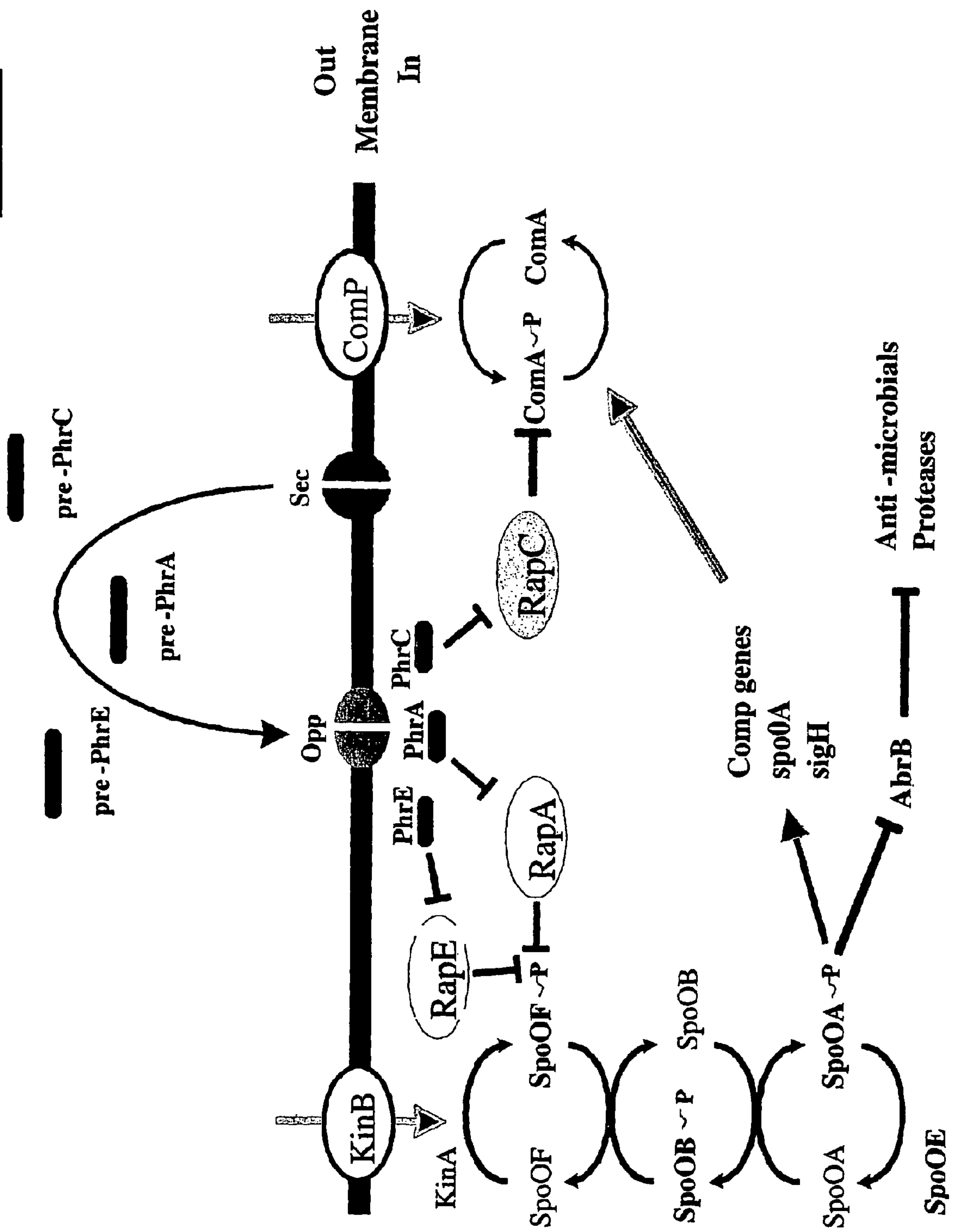
FIG. 22 depicts the sporulation phosphorelay in *Bacillus*. This system is the central signal processing system determining whether cells enter into sporulation. It consists of an elaborated two component system which consist of a signal sensing histidine kinase and a response regulator. Further fine tuning of this particular system in response to a variety of signals is achieved through specific phosphatases (Rap proteins) which in turn are regulated through the action of cognate phosphatase inhibitory peptides, processed forms of Phr proteins. The large number of two component systems in bacterial species (at least 35 in *B. subtilis*) requires exquisite specificity of molecular recognition between kinase/response regulator protein pairs to assure that signals are not transduced incorrectly to homologous systems, so-called cross-talk. Green arrows indicate transcriptional or functional activation. Red lines indicate transcription repression or functional inactivation.

As discussed in greater detail below, the *B. clausii* (PB92) sequence was compared with genomes of *B. subtilis* and *B. halodurans*. Although the *B. clausii* sequence was highly similar to the sequences from both of the other members of the genus *Bacillus*, the data suggest that there is a closer relationship between *B. clausii* and *B. halodurans*, than between *B. clausii* and *B. subtilis*. However, as shown in FIG. 21, there are also clear examples of genes in *B. clausii* that are more similar to *B. subtilis* than *B. halodurans*.

Sequencing

A shotgun library of the *B. clausii* PB92 genome was sequenced using standard methods known in the art. The subsequent assembly of the individual sequences resulted in 450 non-overlapping contigs with a total length of 4,345,345 base pairs. Gene prediction was performed automatically using the Orpheus software (Frishman et al., Nuc. Acids Res., 26:2941–7 [1998]). All predicted open reading frame (ORF) boundaries were manually refined on the basis of extrinsic evidence. Intergenic regions of the genome and ORFs for which no match could be found in a non-redundant protein database were reevaluated using BLASTX. ORFs were then extrapolated from the regions of alignments.

Additional genetic elements (tRNAs, rRNAs, scRNAs, transposable elements) were also annotated. ORFs that were internal to or overlapping with known genetic elements were modified or removed from the data set. The main vehicle for automatic and manual annotation of the gene products was the Pedant-Pro™ Sequence Analysis Suite (Frishman et al., Bioinformatics 17:44–57 [2001]). Extracted proteins were subjected to exhaustive bioinformatics analyses, including similarity searches, protein motif identification, and protein secondary structure and feature prediction, including sensitive fold recognition. For each ORF, functional categories were manually assigned according to the MIPS Functional Catalogue (Mewes et al., Nature 387:7–65 [1997]).

Sequences

The sequences of various regulatory and/or secretion associated proteins are shown in FIGS. 1 through 20 and 25–32. FIG. 1 shows the deduced amino acid for SpollE from *B. clausii* (SEQ ID NO:1). FIG. 2 shows the DNA sequence for spollE from *B. clausii* (SEQ ID NO:2). It is a desirable characteristic that a production strain be deficient in sporulation. Thus, experiments were conducted to assess the sporulation characteristics of the *B. clausii* identified during the development of the present invention.

*B. subtilis* is capable of entering sporulation during times of great stress in the environment, such as extreme lack of nutrients. Making this decision triggers a very elaborate and energy-expensive conversion to the sporulation development state. Over 50 genes which need to be expressed for sporulation are under the control of eight sporulation control genes, namely Spo0A, Spo0B, Spo0lE, Spo0F, Spo0H, Spo0J, Spo0K, and Spo0L, with spo0A being the most critical control factor. Mutation in the sporulation control genes allows the cells to ignore their environment, so that they fail to enter sporulation and continue production of heterologous and/or homologous proteins. Although it is not intended that the present invention be limited to any particular mechanism or theory, it is believed that the spollE gene of *B. clausii* functions in a manner similar to the *B. subtilis* homolog. Thus, it is contemplated that by mutating the spollE gene in *B. clausii*, a beneficial sporulation-deficient strain will result.

FIG. 3 shows the deduced amino acid for the DegS (SEQ ID NO:29) and DegU (SEQ ID NO:3) from *B. clausii* (SEQ ID NO:3), while FIG. 4 shows the DNA sequence coding for degS (SEQ ID NO:30) and degU from *B. clausii* (SEQ ID NO:4). The degS and degU genes of *B. subtilis* belong to the family of two-components regulatory systems, and encode proteins involved in the control of expression of different cellular functions, including degradative enzyme synthesis, competence for DNA uptake and the presence of flagella. Two classes of mutations have been identified in both genes. One class of mutations leads to decreased expression (degU mutations), while the second one leads to enhanced expression [degU(Hy) mutations] of regulated genes (i.e., genes regulated by the degU system) (Msadeck et al., In: Sonenshein et al., (eds.), *Bacillus subtilis and Other Gram-Positive Bacteria*, American Society for Microbiology, Washington, D.C., page 729–745 [1993]). This second class of mutations is associated with a pleiotropic phenotype which, in *B. subtilis*, includes the ability to sporulate in the presence of glucose, loss of flagella, and decreased genetic competence.

It is known that several of the production *Bacillus* strains carry one or more mutations in either the degS or the degU genes which confer certain characteristics such as lower catabolite repression and better enzyme secretion to the strain. Thus, it was contemplated that the *B. clausii* degS and/or degU find similar uses. Therefore, it was considered desirable to:

1) conduct in vitro random mutagenesis of the degS and/or degU genes, replace either or both the wild type genes with such mutagenized population and select for the mutants which confer the phenotypes described above;
2) introduce one or more mutations in the residues of the native DegU gene, such as: H17X, (by XI mean any other amino acid) T103×, E112X, V136X, etc., wherein "X" is any amino acid; and/or
3) introduce one or more mutations in the residues of the native DegS gene, such as: V238X, wherein "X" is any amino acid. Mutated genes, carrying one or more of these mutations are used to replace the wild type gene in *B. clausii* are thereby provided. In addition, the present invention encompasses any degU and/or degS mutation that increasing phosphorylation; and
4) transform the *B. clausii* with its own degS and/or degU gene(s) carried either in a multicopy plasmid or transcribed by a stronger promoter so to obtain higher levels of expression of such gene. In some embodiments, the genes are wild-type, while in other embodiments, the genes are mutated.

The present invention provides a further gene of interest. FIG. 33 provides the amino acid sequence (SEQ ID NO:31) and FIG. 34 provides the DNA sequence (SEQ ID NO:32) of "gene 2627," which is homologous to the transcriptional activator gene nprA from *Bacillus stearothermophilus*. In *B. stearothermophilus* the nprA gene is located adjacent to the gene coding for the neutral protease nprS. It has been observed that hyper-expression of the nprA gene, such as cloning it in a multicopy plasmid, increases the expression of the adjacent neutral protease (Nishiya and Imanaka, J. Bacteriol., 172:4861–4869 [1990]). It is therefore desirable to hyper-express gene 2627 in *B. clausii*, transforming *B. clausii* with gene 2627 carried either in a multicopy plasmid or integrated in the chromosome under the transcriptional control of a stronger promoter, so to obtain higher levels of expression of such gene.

The Sec-dependent protein transport pathway is responsible for the translocation of proteins containing amino-terminal signal sequences across the cytoplasmic membrane. The Sec machinery is composed of a proteinaceous channel in the cell membrane (consisting of SecY, SecE, SecG and SecDF (in *B. subtilis*) or SecD and SecF in (*B. halodurans*)) and a translocation motor (SecA). The Sec machinery is known to 'thread' its substrates in an unfolded state through the membrane. Consequently, this machinery is inherently incapable of translocating proteins that fold in the cytosol. A number of the components of this transport system from *B. clausii* were identified.

Nearly all secreted proteins use an amino-terminal protein extension, known as the signal peptide, which plays a crucial role in the targeting to and translocation of precursor proteins across the membrane and which is proteolytically removed by a signal peptidase during or immediately following membrane transfer. The newly synthesized precursor proteins are recognized by specific proteins in the cytoplasm, collectively called "chaperones." These chaperones prevent polypeptides destined for translocation to aggregate or fold prematurely which would lead to an export-incompatible conformation.

Most of the exported proteins are translocated in an unfolded conformation via the general secretion (Sec) pathway. Cytoplasmic chaperones and targeting factors like the Ffh protein that is homologous to the 54-kDa subunit of the mammalian signal recognition particle (SRP) and the FtsY protein a homologue of the mammalian SRP receptor alpha-subunit facilitate targeting of the pre-proteins to the Sec-translocase in the membrane. FIGS. 5–20 provide amino acid and DNA sequences for FtsY, Ffh, SecA, SecD, SecE, SecF, SecG, and SecY of *B. clausii* (respectively). In these Figures, SecE, SecG and Ffh are provided as partial sequences. However, it is intended that the present invention encompass the complete sequences of these genes and polypeptides.

Upon translocation across the membrane, the signal peptide is removed by a signal peptidase, which is a prerequisite for the release of the translocated protein from the membrane, and its secretion into the medium. Thus, in some embodiments, the proteins of interest have signal peptides that require removal. Signal peptidases identified herein are designated SipS, SipT, SipV, SipW (See, FIGS. 25–32). It is contemplated that any of the above proteins will find use in a manner similar to orthologs that are known in the art.

Hybridization Analogs

In one embodiment of the present invention, a protein is a "secretion-associated protein," if it assists a nascent protein to fold correctly or to be translocated from the intracellular to extracellular environment. In one embodiment of the present invention, the secretion-associated protein is a variant of the wild-type protein wherein it has an overall homology greater than about 40%, more preferably greater than about 60%, more preferably at least 75%, more preferably greater than about 80%, even more preferably greater than about 85% and most preferably greater than 90% to the amino acid sequence of any one of FIGS. 5, 7, 9, 11, 13, 15, 17, 19, 21, 23, 25 or 27. In some embodiments the homology is as high as about 93 to 95 or, in particularly preferred embodiments, 98%.

Accordingly, the present invention provides methods for the detection of Gram-positive polynucleotide homologs which comprise hybridizing part or all of a nucleic acid sequences encoding *B. clausii* regulatory and/or secretion-associated proteins with Gram-positive microorganism nucleic acid of either genomic or cDNA origin.

Also included within the scope of the present invention are Gram-positive microorganism polynucleotide sequences that are capable of hybridizing to the nucleotide sequences encoding *B. clausii* regulatory and/or secretion-associated proteins under conditions of intermediate to maximal stringency.

Also included within the scope of the present invention are novel Gram-positive microorganism polynucleotide sequences encoding regulatory and/or secretion-associated proteins that are capable of hybridizing to part or all of any one of the nucleotide sequences encoding *B. clausii* regulatory and/or secretion-associated proteins of FIGS. 1–20 and 25–32 under conditions of intermediate to maximal stringency.

In addition, amplification methods known in the art, such as the polymerase chain reaction (PCR) find use in amplifying *B. clausii* sequences. In some embodiments, a nucleic acid sequence of at least about 10 nucleotides and as many as about 60 nucleotides from any one of the nucleotide sequences encoding a *B. clausii* regulatory and/or secretion-associated protein of FIGS. 1–20 and 25–32, preferably about 12 to 30 nucleotides, and more preferably about 20–25 nucleotides are used as a probe or PCR primer.

In a further embodiment, the present invention provides DNA sequences encoding regulatory and/or secretion-associated protein having more than 40%, more than 45%, more than 50%, more than 55%, more than 60%, more than 65%, more than 70%, more than 75%, more than 80%, more than 85%, more than 90%, more than 95%, or more than 98% homology with the wild-type sequence.

Hybrids

The present invention also provides nucleic acids encoding hybrid secretion factors and amino acids comprising the hybrid secretion factors. In these embodiments, the hybrid secretion-associated factors retain the function of the corresponding *B. clausii* secretion-associated factor. In some embodiments, the present invention provides hybrids between *B. clausii* and other species, including but not limited to *B. subtilis*. Thus, in some embodiments, the microorganism comprises *B. clausii* sequences as well as sequences from another organism, such as *B. subtilis*.

In one embodiment, the orthologous sequences comprise a sequence from a single ortholog. In another embodiment, the orthologous sequences comprise less than 5 sequences from a single ortholog. In a further embodiment, the orthologous sequences comprise sequences from two orthologs. In an additional embodiment, the orthologous sequences comprise a single amino acid. In another embodiment, the orthologous sequences comprise from between two amino acids to five, 10, 15, 20 amino acids. In yet a further embodiment, the orthologous sequences comprise from about 2% to about 50%, in total, of the secretion factor sequence.

In alternative embodiments, the orthologous sequences comprise great than two amino acids and less than five, 10, 15, 20, 25, 30, 35, 40, 45 or 50 amino acids. In still another embodiment, the orthologous sequences comprise less than about 50%, in total, of the hybrid secretion factor sequence when compared to the wild-type *B. clausii* secretion factor.

Proteins of Interest

The present invention is particularly useful in enhancing the intracellular and/or extracellular production of proteins. In some embodiments, the protein is homologous, while in other embodiments, it is heterologous. The present invention finds use in the production of various proteins, including but not limited to hormones, enzymes, growth factors, cytokines, antibodies, and the like. The present invention finds particular use in the production of enzymes, including but not limited to hydrolases, such as proteases, esterases, lipases, phenol oxidase, permeases, amylases, pullulanases, cellulases, glucose isomerase, laccases and protein disulfide isomerases. However, the present invention also finds use in the production of hormones, including but are not limited to, follicle-stimulating hormone, luteinizing hormone, corticotropin-releasing factor, somatostatin, gonadotropin hormone, vasopressin, oxytocin, erythropoietin, insulin and the like.

Growth factors are proteins that bind to receptors on the cell surface, with the primary result of activating cellular proliferation and/or differentiation. In addition to enzymes and hormones, the present invention finds use in the production of growth factors including but are not limited to, platelet-derived growth factor, epidermal growth factor, nerve growth factor, fibroblast growth factors, insulin-like growth factors, transforming growth factors, etc. Cytokines are a unique family of growth factors. Secreted primarily from leukocytes, cytokines stimulate both the humoral and cellular immune responses, as well as the activation of phagocytic cells. Cytokines include, but are not limited to, colony stimulating factors, the interleukins (e.g., IL-1 [α and β], IL-2 through IL-13) and the interferons (α, β and γ).

Human Interleukin-3 (IL-3) is a 15 kDa protein containing 133 amino acid residues. IL-3 is a species-specific colony stimulating factor which stimulates colony formation of megakaryocytes, neutrophils, and macrophages from bone marrow cultures.

In addition to the above proteins, it is contemplated that the present invention will find use in embodiments involving antibodies. Antibodies include, but are not limited to, immunoglobulins from any species from which it is desirable to produce large quantities. It is especially preferred that the antibodies are human antibodies. Immunoglobulins may be from any class (i.e., IgG, IgA, IgM, IgE, or IgD).

The present invention is particularly useful in enhancing the production and secretion of proteins that possess non-polar or substantially non-polar carboxy termini. Thus, it is contemplated that proteins that comprises a signal sequence and a non-polar or substantially non-polar carboxy terminus find particular use in the present invention. The protein may be homologous or heterologous.

In some embodiments of the present invention, the protein of interest is fused to a signal peptide. Signal peptides from two secretory pathways are specifically contemplated by the present invention. The first pathway is the sec-dependent pathway. This pathway is well characterized and a number of putative signal sequences have been described. It is intended that all sec-dependent signal peptides be encompassed by the present invention. Specific examples include, but are not limited to the AmyL and the AprE sequences. The AmyL sequence refers to the signal sequence for α-amylase and AprE refers to the AprE signal peptide sequence (AprE is subtilisin [also referred to as alkaline protease] of *B. subtilis*). Any signal sequence derived from any source may be used as long as it is functional (i.e., directs the protein of interest into the secretory pathway), in the host cell.

Host Cells

The present invention provides host microorganisms and expression means for the expression, production and secretion of desired proteins in Gram-positive microorganisms, such as members of the genus *Bacillus*.

In a general embodiment, the present methods find use in enhancing the expression and/or secretion of any protein of interest produced intracellularly or secreted via the Sec-dependent secretion pathway. Thus, any protein of interest that may be fused to a Sec-dependent signal peptide by recombinant DNA methods finds use in the present invention.

The host cell is rendered capable of enhanced secretion of a protein of interest by transforming the host cell with nucleotide sequences encoding one or more of the inventive *B. clausii* secretion factors. In some embodiments, the protein of interest is endogenous, while in other embodiments, it is heterologous. In some embodiments, the protein of interest is a chimeric protein in which a native protein of interest is fused to a Sec-dependent signal sequence. In a preferred embodiment the *B. clausii* secretion factor gene is operably linked to a promoter. The promoter may be constitutive or inducible. In one embodiment, the promoter is the *B. subtilis* aprE promoter. However, preferred promoters are host cell promoters that are responsible for the transcription of the ortholog genes. For example, in *B. subtilis*, the secA promoter would be used to express the *B. clausii* secA gene, the *B. subtilis* secY promoter would be used to express the *B. clausii* secY gene, etc.

It is further contemplated that by varying the level of induction of an inducible promoter it is possible to modulate the expression of the gene product and thereby modulate the secretion of the protein of interest.

In some embodiments, the host cell is a Gram-positive cell. In preferred embodiments, the Gram-positive cell is a member of the genus *Bacillus*. As used herein, the genus *Bacillus* includes all members known to those of skill in the art, including but not limited to *B. subtilis, B. licheniformis, B. lentus, B. brevis, B. stearothermophilus, B. amyloliquefaciens, B. halodurans, B. clausii, B. coagulans, B. circulans, B. megaterium, B. lautus*, and *B. thuringiensis*. In some particularly preferred embodiments, the member of the genus *Bacillus* is selected from the group consisting of *B. subtilis, B. clausii*, and *B. licheniformis.*

DNA Constructs

The present invention provides expression systems for the enhanced production and secretion of desired heterologous or homologous proteins in a host microorganism. The various components of the DNA construct may be assembled by any suitable method, including PCR and/or ligation. It should be noted that any technique may be used as long as the DNA construct has the final configuration desired. In preferred embodiments, the DNA constructs are incorporated into vectors that include, but are not limited to, integrating single copy vectors, integrating amplifiable vectors or multicopy vectors.

Promoters

As indicated above, the promoter may be either inducible or constitutive. Preferred promoters for use herein are promoters from the host cell that correspond to the *B. clausii* secretion factor. Alternatively, the *B. clausii* promoter normally associated with the secretion factor may be used. In another embodiment, the promoter may be any promoter that is functional in the host cell and is not the native promoter for the *B. clausii* secretion factor.

Signal Sequence/Protein of Interest

In some preferred embodiments of the present invention, the vector comprises at least one copy of nucleic acid encoding a Gram-positive microorganism secretion factor and preferably comprises multiple copies. In additional embodiments, the vector comprises sequences (e.g., *B. clausii* sequences) are integrated into the host cell genome, preferably as a single copy. In additional embodiments, host cells are provided that carry both genes (i.e., native and introduced sequences). In further embodiments, the present invention provides vectors that contain the native gene of interest, while in still other embodiments, the vectors contain hybrid sequences. Thus, the present invention provides multiple embodiments in which incoming sequences, hybrids, and native sequences are present in any appropriate combination.

In some preferred embodiments, the Gram-positive microorganism is *Bacillus*. In another preferred embodiment, the gram-positive microorganism is *B. subtilis*. In a preferred embodiment, polynucleotides which encode *B. clausii* secretion associated factors, or fragments thereof, or fusion proteins or polynucleotide homolog sequences that encode amino acid variants of said secretion factors, are used to generate recombinant DNA molecules that direct the expression of the secretion-associated proteins, or amino acid variants thereof, respectively, in Gram-positive host cells. In a preferred embodiment, the host cell belongs to the genus *Bacillus*. In another preferred embodiment, the host cell is *B. subtilis*.

As will be understood by those of skill in the art, it may be advantageous to produce polynucleotide sequences possessing non-naturally occurring codons. Thus, in some embodiments, codons preferred by a particular Gram-positive host cell (See, Murray et al., Nuc. Acids Res., 17:477–508 [1989]) are selected, for example, to increase the rate of expression or to produce recombinant RNA transcripts having desirable properties, such as a longer half-life, than transcripts produced from naturally occurring sequence.

Altered *B. clausii* secretion factor polynucleotide sequences which find use in the present invention include deletions, insertions, and/or substitutions of different nucleotide residues resulting in a polynucleotide that encodes the same or a functionally equivalent secretion factor homolog, respectively. In alternative embodiments, the encoded protein contains deletions, insertions and/or substitutions of amino acid residues that produce a silent change and result in a functionally equivalent *B. clausii* secretion factor variant. Deliberate amino acid substitutions may be made on the basis of similarity in polarity, charge, solubility, hydrophobicity, hydrophilicity, and/or the amphipathic nature of the residues, as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

In some embodiments, the *B. clausii* secretion factor polynucleotides of the present invention are engineered in order to modify the cloning, processing and/or expression of the gene product. For example, mutations may be introduced using techniques which are well known in the art (e.g., site-directed mutagenesis to insert new restriction sites, alter glycosylation patterns, and/or to change codon preference).

Transformation of *Bacillus* Host Cells

In some embodiments of the present invention, nucleic acid encoding at least one polypeptide of interest is introduced into a host cell via an expression vector capable of replicating within the host cell. Suitable replicating and integrating plasmids for *Bacillus* known in the art (See e.g., Harwood and Cutting (eds), *Molecular Biological Methods for Bacillus*, John Wiley & Sons, [1990], in particular, chapter 3; suitable replicating plasmids for *B. subtilis* include those listed on page 92). Although there are technical hurdles, those of skill in the art know that there are several strategies for the direct cloning of DNA in *Bacillus*.

Methods known in the art to transform *Bacillus*, include such methods as plasmid marker rescue transformation, involves the uptake of a donor plasmid by competent cells carrying a partially homologous resident plasmid (Contente et al., Plasmid 2:555–571 [1979]; Haima et al., Mol. Gen. Genet., 223:185–191 [1990]; Weinrauch et al., J. Bacteriol., 154:1077–1087 [1983]; and Weinrauch et al., J. Bacteriol., 169:1205–1211 [1987]). In this method, the incoming donor plasmid recombines with the homologous region of the resident "helper" plasmid in a process that mimics chromosomal transformation.

Another method involving transformation by protoplast transformation is known in the art (See, Chang and Cohen, Mol. Gen. Genet., 168:111–115 [1979], for *B. subtilis*; Vorobjeva et al., FEMS Microbiol. Lett., 7:261–263 [1980], for *B. megaterium*; Smith et al., Appl. Env. Microbiol., 51:634 [1986], for *B. amyloliquefaciens*; Fisher et al., Arch. Microbiol., 139:213–217 [1981], for *B. thuringiensis*; McDonald [1984] J. Gen. Microbiol., 130:203 [1984], for *B. sphaericus*; and Bakhiet et al., 49:577 [1985] *B. larvae*). In addition, Mann et al., (Mann et al., Curr. Microbiol., 13:131–135 [1986]) describe transformation of *Bacillus* protoplasts, and Holubova (Holubova, Microbiol., 30:97 [1985]) describe methods for introducing DNA into protoplasts using DNA-containing liposomes. In some preferred embodiments, marker genes are used in order to indicate whether or not the gene of interest is present in the host cell.

In addition to these methods, in other embodiments, host cells are directly transformed. In "direct transformation," an intermediate cell is not used to amplify, or otherwise process, the DNA construct Prior to introduction into the host (i.e., *Bacillus*) cell. Introduction of the DNA construct into the host cell includes those physical and chemical methods known in the art to introduce DNA into a host cell without insertion into a plasmid or vector. Such methods include but are not limited to the use of competent cells, as well as the use of "artificial means" such as calcium chloride precipitation, electroporation, etc. to introduce DNA into cells. Thus, the present invention finds use with naked DNA, liposomes and the like. In yet other embodiments, the DNA constructs are co-transformed with a plasmid without being inserted into the plasmid.

Vectors/Plasmids

For expression, production and/or secretion of protein(s) of interest in a cell, an expression vector comprising at least one copy of a nucleic acid encoding the heterologous and/or homologous protein(s), and preferably comprising multiple copies, is transformed into the cell under conditions suitable for expression of the protein(s). In some particularly preferred embodiments, the sequences encoding the protein of interest (as well as other sequences included in the vector) are integrated into the genome of the host cell, while in other embodiments, the plasmids remain as autonomous extrachromosomal elements within the cell. Thus, the present invention provides both extrachromosomal elements as well as incoming sequences that are integrated into the host cell genome.

In some embodiments of the present invention, any one or more of the inventive secretion factors are introduced into the host cell on the same vector as the protein of interest. Alternatively, in other embodiments, any one or more of the inventive secretion factors are introduced into the host cell on a separate vector. In some embodiments in which the secretion factor is on a separate vector, the vectors are used to transform the host cell at the same time as the vector possessing the protein of interest. In alternative embodiments, the host cell is transformed sequentially (i.e., with one vector then followed with the second vector).

In preferred embodiments, expression vectors used in expressing the secretion factors of the present invention in Gram-positive microorganisms comprise at least one promoter associated with a Gram-positive secretion factor, which promoter is functional in the host cell. In one embodiment of the present invention, the promoter is the wild-type promoter for the selected secretion factor and in another embodiment of the present invention, the promoter is heterologous to the secretion factor, but still functional in the host cell.

Additional promoters associated with heterologous nucleic acid encoding desired proteins or polypeptides introduced via recombinant DNA methods find use in the present invention. In one embodiment of the present invention, the host cell is capable of overexpressing a heterologous protein or polypeptide and nucleic acid encoding one or more secretion factor(s) is(are) recombinantly introduced. In one preferred embodiment of the present invention, nucleic acid encoding a *B. clausii* secretion-associated protein is stably integrated into the microorganism genome. In another embodiment, the host cell is engineered to overexpress a secretion factor of the present invention and nucleic acid encoding the heterologous protein or polypeptide is introduced via recombinant DNA techniques. The present invention encompasses Gram-positive host cells that are capable of overexpressing other secretion factors known to those of skill in the art, and/or other secretion factors known to those of skill in the art or identified in the future.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers (e.g., antimicrobial markers such as erythromycin, actinomycin, chloramphenicol, and tetracycline). In yet another embodiment, a multicopy replicating plasmid is for integration of the plasmid into the *Bacillus* genomic DNA using methods known in the art.

Culturing Host Cells for Expression and Identification of Transformants

Although the presence/absence of marker gene expression suggests that the gene of interest is also present, its presence and expression should be confirmed. For example, in some embodiments in which the nucleic acid encoding a secretion-associated protein is inserted within a marker gene sequence, recombinant cells containing the insert are identified by the absence of marker gene function. Alternatively, a marker gene can be placed in tandem with nucleic acid encoding the secretion factor under the control of a single promoter. Expression of the marker gene in response to induction or selection usually indicates expression of the secretion factor as well.

Alternatively, host cells which contain the coding sequence for a secretion factor and/or express the protein of interest may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the secretion-associated protein polynucleotide sequence can be detected by DNA-DNA or DNA-RNA hybridization or amplification using probes, portions or fragments derived from the *B. clausii* polynucleotide encoding any one of the secretion-associated proteins.

Measuring Gene Product

There are various assays known to those of skill in the art for detecting and measuring activity of secreted polypeptides. In particular, for proteases, there are assays based upon the release of acid-soluble peptides from casein or hemoglobin measured as absorbance at 280 nm or calorimetrically using the Folin method (See, Bergmeyer et al., *Methods of Enzymatic Analysis*, vol. 5, “Peptidases, Proteinases and their Inhibitors,” Verlag Chemie, Weinheim [1984]). Other assays known in the art include the solubilization of chromogenic substrates (Ward, in *Microbial Enzymes and Biotechnology* (Fogarty, ed.), Applied Science, London, [1983], pp. 251–317).

Means for determining the levels of secretion of a heterologous or homologous protein in a host cell and detecting secreted proteins include, include methods that use either polyclonal or monoclonal antibodies specific for the protein. Examples include enzyme-linked immunosorbent assay (ELISA), radioimmunoassay (RIA), fluorescent immunoassay (FIA), and fluorescent activated cell sorting (FACS). These and other assays are well known in the art (See e.g., Maddox et al., J. Exp. Med., 158:1211 [1983]). In one preferred embodiment of the present invention, secretion is higher using the methods and compositions provided herein than when using the same methods or compositions, but where a peptide transport protein or gene product of a peptide transport operon has not been introduced.

Protein Purification

In preferred embodiments, the cells transformed with polynucleotide sequences encoding heterologous or homologous protein or endogenously having said protein are cultured under conditions suitable for the expression and recovery of the encoded protein from the cell culture medium. In some embodiments, other recombinant constructions may join the heterologous or homologous polynucleotide sequences to nucleotide sequence encoding a polypeptide domain which will facilitate purification of soluble protein (e.g., tags of various sorts) (Kroll et al., DNA Cell. Biol., 12:441–53 [1993]).

Such purification facilitating domains include, but are not limited to, metal chelating peptides such as histidine-tryptophan modules that allow purification on immobilized metals (Porath, Prot. Expr. Purif., 3:263–281 [1992]), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego, Calif.) between the purification domain and the heterologous protein can be used to facilitate purification.

From the above, it is clear that the present invention provides genetically engineered Gram-positive host microorganisms comprising preferably non-revertable mutations, including gene replacement, in at least one gene encoding a secretion-associated protein. In some embodiments, the host microorganism contains additional protease deletions, such as deletions of the mature subtilisin protease and/or mature neutral protease (See e.g., U.S. Pat. No. 5,264,366). In some preferred embodiments, the microorganism is also genetically engineered to produce a desired protein or polypeptide. In a preferred embodiment the gram positive microorganism is a member of the genus *Bacillus*.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as should not be unduly limited to such specific embodiments. Indeed, various modifications of the described modes for carrying out the invention that are obvious to those skilled in the art and/or related fields are intended to be within the scope of the present invention.

The invention claimed is:

1. An isolated nucleic acid molecule comprising a nucleotide sequence comprising a *Bacillus clausii* secretion factor, wherein said secretion factor is SecA, and wherein said nucleotide sequence comprises the sequence set forth in SEQ ID NO:10.

2. A vector comprising the isolated nucleotide sequence of claim 1.

3. An expression cassette comprising the vector of claim 2.

4. An isolated host cell of the genus *Bacillus* comprising the expression cassette of claim 3.

5. The secretion factor SecA of claim 1, wherein said secretion factor comprises the amino acid sequence set forth in SEQ ID NO:9.

6. An isolated nucleic acid molecule comprising a nucleotide sequence comprising a *Bacillus clausii* secretion factor, wherein the secretion factor is selected from the group consisting of DegS (SEQ ID NO:4), SegU (SEQ ID NO:30) and Bc12627 (SEQ ID NO:32).

7. A vector comprising the isolated nucleotide sequence of claim 6.

8. An expression cassette comprising the vector of claim 7.

9. An isolated host cell of the genus *Bacillus* comprising the expression cassette of claim 8.

* * * * *